US009976134B2

(12) United States Patent
Estell et al.

(10) Patent No.: US 9,976,134 B2
(45) Date of Patent: May 22, 2018

(54) THERMOLYSIN VARIANTS

(71) Applicant: Danisco US Inc., Palo Alto, CA (US)

(72) Inventors: David A. Estell, San Francisco, CA (US); Ronaldus W. J. Hommes, Haarlem (NL); Amy D. Liu, Sunnyvale, CA (US); Andrew Shaw, San Francisco, CA (US)

(73) Assignee: DANISCO US INC., Palo Alto, CA (US)

(*) Notice: Subject to any disclaimer, the term of this patent is extended or adjusted under 35 U.S.C. 154(b) by 0 days. days.

(21) Appl. No.: 14/794,687

(22) Filed: Jul. 8, 2015

(65) Prior Publication Data
US 2016/0032266 A1  Feb. 4, 2016

Related U.S. Application Data

(62) Division of application No. 14/035,441, filed on Sep. 24, 2013, now abandoned, which is a division of application No. 12/740,782, filed as application No. PCT/US2008/012276 on Oct. 28, 2008, now Pat. No. 8,569,034.

(60) Provisional application No. 60/984,664, filed on Nov. 1, 2007.

(51) Int. Cl.
*C12N 9/54* (2006.01)
*C11D 3/386* (2006.01)

(52) U.S. Cl.
CPC ............ *C12N 9/54* (2013.01); *C11D 3/386* (2013.01); *C11D 3/38618* (2013.01); *C11D 3/38636* (2013.01); *C12Y 304/24027* (2013.01)

(58) Field of Classification Search
None
See application file for complete search history.

(56) References Cited

U.S. PATENT DOCUMENTS

| | | |
|---|---|---|
| 4,430,243 A | 2/1984 | Bragg |
| 4,515,705 A | 5/1985 | Moeddel .................. 252/174.12 |
| 4,515,707 A | 5/1985 | Brooks ........................ 252/368 |
| 4,537,706 A | 8/1985 | Severson, Jr. ............... 252/545 |
| 4,550,862 A | 11/1985 | Barker et al. ................ 222/109 |
| 4,561,998 A | 12/1985 | Wertz et al. ................. 252/547 |
| 4,597,898 A | 7/1986 | Vander Meer ............... 252/529 |
| 4,683,195 A | 7/1987 | Mullis et al. .................... 435/6 |
| 4,683,202 A | 7/1987 | Mullis ........................... 435/91 |
| 4,965,188 A | 10/1990 | Mullis et al. .................... 435/6 |
| 4,968,451 A | 11/1990 | Scheibel et al. ............. 252/549 |
| 4,977,252 A | 12/1990 | Chiu ............................ 536/102 |
| 5,322,770 A | 6/1994 | Gelfand ........................... 435/6 |
| 5,354,559 A | 10/1994 | Morehouse .................. 424/488 |
| 5,486,303 A | 1/1996 | Capeci et al. ................ 252/89.1 |
| 5,489,392 A | 2/1996 | Capeci et al. ................ 252/89.1 |
| 5,516,448 A | 5/1996 | Capeci et al. ................ 252/89.1 |
| 5,565,145 A | 10/1996 | Watson et al. ............... 510/350 |
| 5,565,422 A | 10/1996 | Del Greco et al. .......... 510/443 |
| 5,569,645 A | 10/1996 | Dinniwell et al. ........... 510/276 |
| 5,574,005 A | 11/1996 | Welch et al. ................. 510/444 |
| 5,576,282 A | 11/1996 | Miracle et al. ............... 510/276 |
| 5,595,967 A | 1/1997 | Miracle et al. |
| 5,597,936 A | 1/1997 | Perkins et al. ............... 556/148 |
| 5,691,297 A | 11/1997 | Nassano et al. ............. 510/444 |
| 5,700,676 A * | 12/1997 | Bott ....................... C11D 3/386 435/220 |
| 5,728,544 A | 3/1998 | Tanaka et al. |
| 5,879,584 A | 3/1999 | Bianchetti et al. ....... 252/186.23 |
| 5,929,022 A | 7/1999 | Velazquez ..................... 510/499 |
| 5,935,826 A | 8/1999 | Blue et al. ...................... 435/96 |
| 6,225,464 B1 | 5/2001 | Hiler, II et al. .............. 540/450 |
| 6,294,514 B1 | 9/2001 | Welling ........................ 510/503 |
| 6,306,812 B1 | 10/2001 | Perkins et al. ............... 510/310 |
| 6,326,348 B1 | 12/2001 | Vinson et al. ................ 510/428 |
| 6,376,445 B1 | 4/2002 | Bettiol et al. ................ 510/320 |
| 6,376,450 B1 | 4/2002 | Ghosh et al. ................ 510/392 |
| 6,582,914 B1 | 6/2003 | Caldwell et al. ................ 435/6 |
| 6,605,458 B1 | 8/2003 | Hansen et al. ............... 435/220 |

FOREIGN PATENT DOCUMENTS

| | | |
|---|---|---|
| JP | H5-199872 | 8/1993 |
| JP | H5-199873 | 8/1993 |
| JP | H6-46850 | 2/1994 |
| JP | H9-255 | 1/1997 |
| WO | WO 97/11151 | 3/1997 |
| WO | WO 98/44127 | 10/1998 |
| WO | WO 99/34011 | 7/1999 |
| WO | WO 99/67370 | 12/1999 |
| WO | WO 00/32601 | 6/2000 |

(Continued)

OTHER PUBLICATIONS

Hardy et al, Stabilization of Bacillus stearothermophilus neutral introduction of prolines. FEBS letts vol. 317, No. 1,2, 89-92 (1993).*
Nishiya et al, 1990 Cloning and Nucleotide Sequences of the Bacillus stearothermophilus Neutral Protease Gene and Its Transcriptional Activator Gene. Journal of Bacteriology, Sep. 1990, p. 4861-4869.*
UniProt Acc# P23384 from Van den Burg et al, Bacteriol. 173:4107-4115(1991). Alignment with SEQ ID No. 3.*
Mansfeld, J., et al., "The Stability of Engineered Thermostable Neutral Proteases From *Bacillus Stearothermophilus*in Organic Solvents and Detergents." *Biotechnol Bioeng.* 97(4): 672-679, 2007.

(Continued)

*Primary Examiner* — Sheridan Swope

(57) ABSTRACT

The present invention provides methods and compositions comprising at least one thermolysin-like neutral protease enzyme with improved storage stability and/or catalytic activity. In some embodiments, the thermolysin finds use in cleaning and other applications comprising detergent. In some particularly preferred embodiments, the present invention provides methods and compositions comprising thermolysin formulated and/or engineered to resist detergent-induced inactivation.

12 Claims, 8 Drawing Sheets

(56) References Cited

FOREIGN PATENT DOCUMENTS

| WO | WO2002/14490 | 2/2002 |
| WO | WO 04/113521 | 12/2004 |

OTHER PUBLICATIONS

Van Solingen, P., et al. "Cloning and expression of an endocellulase gene from a novel streptomycete isolated from an East African soda lake." *Extremophiles* 5:333-341, 2001.

Grobelny, D., et al., "Inhibition of Human Skin Fibroblast Collagenase, Thermolysin and Pseudomonas aeruginosa elastase by Peptide Hydroxamic Acids." Biochemistry 31: 7152-7154, 1992.

NCB I database Acc#720316 Jul. 10, 1992 from Titani et al, Amino-acid sequence of thermolysin. Nature New Bioi. 238 (80), 35-37 (1972). Alignment with SEQ ID No. 3.

UniProt Acc# P23384 from Van den Burg et al, Bacterial. 173:4107-4115 (1991).

Hardy et al, Stabilization of *Bacillus stearothermophilus* neutral introduction of pralines. FEBS letts vol. 317, No. 1, 2, 89-92 (1993).

Nishiya et al, 1990 Cloning and Nucleotide Sequences of the *Bacillus stearothermophilus* Neutral Protease Gene and Its Transcriptional Activator Gene. Journal of Bacteriology, Sep. 1990, p. 4861-4869.

Altschul, S.F., et al., "Basic Local Alignment Search Tool." *J Mol Biol*, 215: 403-410, 1990.

Altschul, S.F., et al., "Local Alignment Statistics." *Meth Enzymol*, 266: 460-480, 1996.

Chamberlin, M., et al., "New RNA Polymerase from *Escherichia coli* infected with Bacteriophage T7." *Nature* 228: 227-231, 1970.

Chen, X.-G., et al., "Thermoactive extracellular proteases of *Geobacillus caldoproteolyticus*, sp, nov., from sewage sludge." *Extremophiles* 8(6): 489-498, 2004.

Del Mar, E.G., et al., "A Sensitive New Substrate for Chymotrypsin." *Anal. Biochem.* 99: 316-320, 1979.

Devereux J., et al., "A comprehensive set of sequence analysis programs for the VAX." *Nucl. Acid Res.* 1291: 387-395, 1984.

Dynan, W.S., et al., "Control of eukaryotic messenger RNA synthesis by sequence-specific DNA-binding proteins." *Nature* 316: 774-778, 1985.

Feng, D.-F., et al., "Progressive Sequence Alignment as a Prerequisite to Correct Phylogenetic Trees." *J Mol. Evol.* 25: 351-360, 1987.

Ferrari, E., et al., "Genetics." In Hardwood 1989 et al, (eds.), *Bacillus* Plenum Publishing Corp., pp. 57-72, 1989.

Galante, Y.M., et al., "Enzyme Applications in Detergency and in Manufacturing Industries." *Current Organic Chemistry*, 7: 1399-1422, 2003.

Galardy, R.E., "Galardin™. Antiinflammatory Protease Inhibitor." *Drugs of the Future* 18(12): 1109-1111, 1993.

Guerot-Fleury, A.-M., et al., "Antibiotic-resistance cassettes for *Bacillus subtilis*." Gene, 167: 335-336, 1995.

Higgins, D.G., et al., "Fast and sensitive multiple sequence alignments on a microcomputer." *CABIOS Communications* 5(2): 151-153, 1989.

Ho, S.N., et al., "Site-directed mutagenesis by overlap extension using the polymerase chain reaction." *Gene* 77(15): 51-59, 1989.

Kacian, D.L., et al., "A Replicating RNA Molecule Suitable for a Detailed Analysis of Extracellular Evolution and Replication." *Proc Natl Acad Sci USA* 69(1): 3038-3042, 1972.

Kalisz, H. M., "Microbial Proteinases." *In: Advances in Biochemical Engineering / Biotechnology*, A. Fiechter (ed.), 36: 1-65, Springer-Verlag Berlin Heidelberg 1988.

Karlin S., et al., "Applications and statistics for multiple high-scoring segments in molecular sequences." *Proc Natl Acad Sci USA*, 90: 5873-5787, 1993.

Komiyama T., et al., "Studies on inhibitory effect of phosphoramidon and its analogs on thermolysin." *Archives of Biochemistry and Biophysics*, 171(2): 727-731, 1975.

Needleman, S.B., et al. "A General Method Applicable to the Search for Similarities in the Amino Acid Sequence of Two Proteins." *J. Mol. Biol.* 48: 443-453, 1970.

Neidhardt F.C., et al., "Culture Medium for Enterobacteria." *J Bacteriol*, 119(3): 736-747, 1974.

O'Donohue, M.J., et al., "Cloning and expression in *Bacillus subtilis* of the npr gene from *Bacillus thermoproteolyticus* Rokko coding for the thermostable metalloprotease thermolysin." *Biochem J*, 300: 599-603, 1994.

Palmeros B., et al., "A family of removable cassettes designed to obtain antibiotic-resistance-free genomic modifications of *Escherichia coli* and other bacteria." *Gene* 247: 255-264, 2000.

Pearson, W.R., "Improved tools for biological sequence comparison." *Proc Natl Acad Sci USA*, 85: 2444-2448, 1988.

Smith, T.F., et al., "Comparison of Biosequences." *Adv Appl Math*, 2: 482-489, 1981.

Trieu-Cuot, P., et al., "Nucleotide sequence of the *Steptococcus faecalis* plasmid gene encoding the 3'5"-aminoglycoside phosphotransferase type III." *Gene*, 23: 331-341, 1983.

Wishart et al., "A single mutation converts a novel phosphotyrosine binding domain into a dual-specificity phosphatase," *J Biol Chem.* Nov. 10, 1995:270(45): 26782-26785.

Whisstock et al. "Prediction of protein function from protein sequence and structure," *Q Rev Biophys*. Aug. 2003: 36(3): 307-40 Review.

Wu, D.Y., et al., "The Ligation Amplification Reaction (LAR)—Amplification of Specific DNA Sequences Using Sequential Rounds of Template-Dependent Ligation." *Genomics* 4: 560-569, 1989.

Yasukawa, K., et al., "Improving the activity and stability of thermolysin by site-directed mutagenesis." *Biochimica et Biophysica Acta*, 1774: 1281-1288, 2007.

International Search Report and the Written Opinion of the International Searching Authority for International Application No. PCT/US2008/012276, dated Nov. 3, 2009.

\* cited by examiner

**Mature Form of *G. caldoproteolyticus* Thermolysin (SEQ ID NO:3)**

```
         10         20         30         40         50         60
ITGTSTVGVG RGVLGDQKNI NTTYSTYYYL QDNTRGNGIF TYDAKYRTTL PGSLWADADN
         70         80         90        100        110        120
QFFASYDAPA VDAHYYAGVT YDYYKNVHNR LSYDGNNAAI RSSVHYSQGY NNAFWNGSQM
        130        140        150        160        170        180
VYGDGDGQTF IPLSGGIDVV AHELTHAVTD YTAGLIYQNE SGAINEAISD IFGTLVEFYA
        190        200        210        220        230        240
NKNPDWEIGE DVYTPGISGD SLRSMSDPAK YGDPDHYSKR YTGTQDNGGV HINSGIINKA
        250        260        270        280        290        300
AYLISQGGTH YGVSVVGIGR DKLGKIFYRA LTQYLTPTSN FSQLRAAAVQ SATDLYGSTS
        310
QEVASVKQAF DAVGVK
```

*FIG. 1*

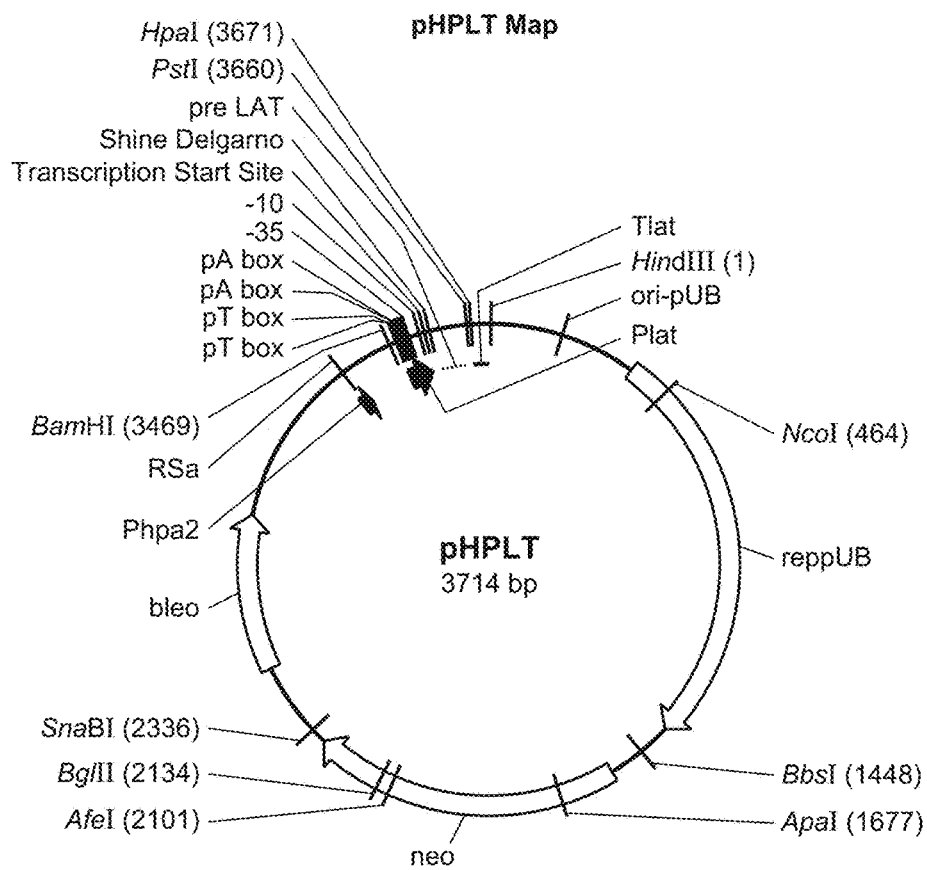

*FIG. 2* pHPLT-thermolysin DNA sequence (SEQ ID NO:8)

FIG. 4A

```
gattcaccggtttgtacaggtgcggagtcgttgctgttattgctgttggtactgctagttgccgcattgaagtagaggaatt
gatgaattatatcaacatattaagccttggcattttgcaccccaatacatcattaaaagatcagtggtggat
gaacgagactttgcagtttcagtccgcgacactggcgattgctgaatatgcttttttgatactctttttatt
ttattaatctgttctgttcgttccgttacactggcaaaaataaaaaaattttaaaagtgccagatctgccttcgg
ttgagtggtttttgtccgttacactggcaaaaataaaaaaattttaaagtggcaaaaccccctttgctgaggtggcagaggc
taagctagacaaaacgtccctgtctgattttctcgtaaaaaaaatataaagttctttaaaggttttatactttactttgagttcaaac
aaatactaccttgtcttttttctcgtgattttctcgtaaaaaaaatataaagttctttaaaggttttatactttactttgagttcaaac
agttttttttgtttctttctcgtgattttctcgtaaaaaaaatataaagttctttaaaggttttatactttactttgagttcaaac
acagcctcgcagaaatgcctcacactttgtgccaatcggcgcttttcacattgaaagggaggaattgaaatcgttcttgtcttgcagcaggac
agagcgaaaatcagggggatcctaatatcatatgtttcacattgaaagggaggaattgaaatcgttcttgtcttgcagcaggac
aaaaagtgaaatcagggggatcctaatatcatatgtttcacattgaaagggaggaattgaaatcgttcttgtcttgcagcaggac
aaattcggaatatattataaggagaggaattttaaccttgatctgcttgaaagtgaacgctaaggcacatcccaagaataaattgaaagaacctgtctacaattcaaa
tttagtctagcaaagtatttttaccttgatctgcttgaaagtgaacgctaaggcacatcccaagaataaattgaaagaacctgtctacaattcaaa
tagcggcccaattcatctccggtgatctgcttgaaagtgaacgctaaggcacatcccaagaataaattgaaagaacctgtctacaattcaaa
ccccctcaattcatctccggtgatctgcttgaaagtgaacgctaaggcacatcccaagaataaattgaaagaacctgtctacaattcaaa
aaaaaaacgaaaaacaagtttaaatttcatgaaaacgctaaggataactctacaattgaaagaacgaaaagaaaaatgata
acctgggttttacgttttatgcgctgacggcgcttatcaggggacactgctgaaaaagattttaagtggcagaggcttcttttagcgtacg
acgtgaaagatggcacgctgacgctgagtgagaacaggggaaaagacaccgagtttgttgttattatgtcaatggcgtgtatatgtcgtgataacagaacatcaactgtcggag
gcggaagaagattgagtgagaacaggggaaaagacaccgagtttgttgttattatgtcaatggcgtgtatatgtcgtgataacagaacatcaactgtcggag
taccggaattgaacacttttttaacttgacgcgcaaaaaatgatgctccaagcggttgatgtcttcattattacgctgtgttgacatatgactact
ttgtcaatttaaaatttaaccaacttgtgatcacgtatgatgctccaagcggttgatgtcttcattattacgctgtgttgacatatgactact
tgggaagaggagtactttgatcacgtatgatgctccaagcggttgatgtcttcattattacgctgtgttgacatatgactact
cgcgtggaaatgggattttttgcgagctattgacacggttcgcacatgagttaacgcatgcggttaacgcttttggaacgttaacgttcgaatttcaggggatcgcgtaacgttcgaatttcagggg
ataaccaatttttttgcgagctattgacacggttcgcacatgagttaacgcatgcggttaacgcttttggaacgttaacgttcgaatttcaggggatcgcgtaacgttcgaatttcagggg
ataaaaatgttcataacgcatttggaacggttcgcacatgagttaacgcatgcggttaacgcttttggaacgttaacgttcgaatttcaggggatcgcgtaacgttcgaatttcagggg
ctgttggtattgatggttgctgcacatgagttcgcacatgagttaacgcatgcggttaacgcttttggaacgttaacgttcgaatttcaggggatcgcgtaacgttcgaatttcagggg
acgaatctggtgcaattaatgaggcatgagtgtatgtatattccaaagcgctatacaggcggtattagcaaggcacgcaagataaaatggcgtgaagtcgtggttcgaatggcggaatacgaaaatggcggaatatc
cagattgggaaattggagaggatgtcactattgtatacagtaatggcggaatatcagaaggcaagatattccaaagcgctataaggcacgcaagataaaatggcggtgagtgttgtcgaatggcggaatatcgaaaatggcggaat
caaagtatgtggattcaacagatccgcttattttgattagcgtgcattagcaaggcggcattagcaaggcacgcaagataaaatggcggtgagtgttgtcgaatggcggaatatcgaaaatggcgg
gcgaattatcaacaaattgggaaaatttctatcagcactgtacgactttgtcgacaagcaggaagtccagaaagtccaacttctgtgaagcagg
gacgcgataaatttgggaaaatttctatcagcactgtacgactttgtcgacaagcaggaagtccagaaagtccaacttctgtgaagcagg
tcgtgctgccgctgttcaatcagcactgtacgactttgtcgacaagcaggaagtccagaaagtccaacttctgtgaagcagg
ccttgatgcggtaggggtgaaataagaattcctgcagttaacagaggacgagttccttcctgaaggaatccgttt
tttattta
```

| FIG. 9A | FIG. 9B |
|---------|---------|

FIG. 9

| 021 | 022 | 023 | 024 | 025 | 026 | 027 | 028 | 029 | 030 | 031 | 032 | 033 | 034 | 035 |
|---|---|---|---|---|---|---|---|---|---|---|---|---|---|---|
| N | T | T | Y | S | T | Y | Y | Y | L | Q | D | N | T | R |
| N | I | I | S | E | G | K | Y | V | L | R | D | L | S | K |

| 053 | 054 | 055 | 056 | 057 | 058 | 059 | 060 | 061 | 062 | 063 | 064 | 065 | 066 | 067 | 068 |
|---|---|---|---|---|---|---|---|---|---|---|---|---|---|---|---|
| S | L | W | A | A | A | D | N | Q | F | F | A | S | Y | D | A |
| T | L | V | S | S | T | I | N | Q | L | T | T | S | Q | Q | R |

| 089 | 090 | 091 | 092 | 093 | 094 | 095 | 096 | 097 | 098 | 099 | 100 | 101 | 102 | 103 | 104 |
|---|---|---|---|---|---|---|---|---|---|---|---|---|---|---|---|
| N | R | L | S | Y | D | G | N | N | A | A | I | R | S | S | V |
| N | R | N | S | Y | D | N | K | G | G | K | I | V | S | S | V |

| 125 | 126 | 127 | 128 | 129 | 130 | 131 | 132 | 133 | 134 | 135 | 136 | 137 | 138 | 139 | 140 |
|---|---|---|---|---|---|---|---|---|---|---|---|---|---|---|---|
| G | D | G | Q | T | F | I | P | L | S | G | G | I | D | V | V |
| G | D | G | S | F | F | S | L | L | S | G | S | I | D | V | T |

| 161 | 162 | 163 | 164 | 165 | 166 | 167 | 168 | 169 | 170 | 171 | 172 | 173 | 174 | 175 | 176 |
|---|---|---|---|---|---|---|---|---|---|---|---|---|---|---|---|
| S | G | A | L | N | E | A | I | S | D | I | F | G | T | L | V |
| P | G | A | L | N | E | A | F | S | D | V | F | G | Y | F | N |

| 197 | 198 | 199 | 200 | 201 | 202 | 203 | 204 | 205 | 206 | 207 | 208 | 209 | 210 | 211 | 212 |
|---|---|---|---|---|---|---|---|---|---|---|---|---|---|---|---|
| I | S | G | Q | S | L | R | M | S | S | D | P | A | K | Y | G |
| V | S | Q | P | A | L | R | L | P | S | N | P | T | K | Y | G |

| 229 | 230 | 231 | 232 | 233 | 234 | 235 | 236 | 237 | 238 | 239 | 240 | 241 | 242 | 243 | 244 |
|---|---|---|---|---|---|---|---|---|---|---|---|---|---|---|---|
| G | G | H | T | N | S | G | I | P | K | D | K | A | A | L | T |
| G | V | H | I | N | S | G | I | I | N | K | K | A | Y | N | T |

| 265 | 266 | 267 | 268 | 269 | 270 | 271 | 272 | 273 | 274 | 275 | 276 | 277 | 278 | 279 | 280 |
|---|---|---|---|---|---|---|---|---|---|---|---|---|---|---|---|
| K | I | F | Y | R | A | L | T | Q | L | L | T | P | T | S | N |
| Q | I | Y | R | R | A | L | L | V | Y | L | P | P | S | S | T |

| 301 | 302 | 303 | 304 | 305 | 306 | 307 | 308 | 309 | 310 | 311 | 312 | 313 | 314 | 315 | 316 |
|---|---|---|---|---|---|---|---|---|---|---|---|---|---|---|---|
| Q | E | A | A | S | V | K | Q | A | F | D | A | A | G | V | K |
| Q | D | A | A | S | V | E | A | A | W | N | A | V | G | L | - |

FIG. 9B

THERMOLYSIN VARIANTS

CROSS REFERENCE TO RELATED APPLICATIONS

The present application is a Divisional of U.S. application Ser. No. 14/035,441, filed on Sep. 24, 2013, which is a Divisional of U.S. application Ser. No. 12/740,782, filed Dec. 22, 2010, now U.S. Pat. No. 8,569,034, which is a 371 National Phase application of PCT/US2008/012276, filed Oct. 28, 2008, which claims the benefit of U.S. Provisional App. No. 60/984,664, filed on Nov. 1, 2007, the disclosure of which application is incorporated herein in its entirety.

SEQUENCE LISTING

The sequence listing submitted via EFS, in compliance with 37 C.F.R. § 1.52(e), is incorporated herein by reference. The sequence listing text file submitted via EFS contains the file "31056US_seqlist.txt", created on Jul. 8, 2015, which is 20,480 bytes in size.

FIELD OF THE INVENTION

The present invention provides methods and compositions comprising at least one thermolysin-like neutral protease enzyme with improved storage stability and/or catalytic activity. In some embodiments, the thermolysin finds use in cleaning and other applications comprising detergent. In some particularly preferred embodiments, the present invention provides methods and compositions comprising thermolysin formulated and/or engineered to resist detergent-induced inactivation.

BACKGROUND OF THE INVENTION

Bacilli are gram-positive bacteria that secrete a number of industrially useful enzymes, which can be produced cheaply in high volume by fermentation. Examples of secreted *Bacillus* enzymes are the subtilisin serine proteases, zinc containing neutral proteases, alpha-amylases, and cellulases. *Bacillus* proteases are widely used in the textile, laundry and household industries (Galante, Current Organic Chemistry, 7:1399-1422, 2003; and Showell, Handbook of Detergents, Part D: Formulation, Hubbard (ed.), NY: Taylor and Francis Group, 2006). Highly efficient color and stain removal from laundry require proteases. However, liquid preparations of cleaning and washing reagents typically contain builders, surfactants, and metal chelators, which have a destabilizing effect on most proteases.

Detergent and other cleaning compositions typically include a complex combination of active ingredients. For example, most cleaning products include a surfactant system, enzymes for cleaning, bleaching agents, builders, suds suppressors, soil-suspending agents, soil-release agents, optical brighteners, softening agents, dispersants, dye transfer inhibition compounds, abrasives, bactericides, and perfumes. Despite the complexity of current detergents, there are many stains that are difficult to completely remove. Furthermore, there is often residue build-up, which results in discoloration (e.g., yellowing) and diminished aesthetics due to incomplete cleaning. These problems are compounded by the increased use of low (e.g., cold water) wash temperatures and shorter washing cycles. Moreover, many stains are composed of complex mixtures of fibrous material, mainly incorporating carbohydrates and carbohydrate derivatives, fiber, and cell wall components (e.g., plant material, wood, mud/clay based soil, and fruit). These stains present difficult challenges to the formulation and use of cleaning compositions.

In addition, colored garments tend to wear and show appearance losses. A portion of this color loss is due to abrasion in the laundering process, particularly in automated washing and drying machines. Moreover, tensile strength loss of fabric appears to be an unavoidable result of mechanical and chemical action due to use, wearing, and/or washing and drying. Thus, a means to efficiently and effectively wash colored garments so that these appearance losses are minimized is needed.

In sum, despite improvements in the capabilities of cleaning compositions, there remains a need in the art for detergents that remove stains, maintain fabric color and appearance, and prevent dye transfer. In addition, there remains a need for detergent and/or fabric care compositions that provide and/or restore tensile strength, as well as provide anti-wrinkle, anti-bobbling, and/or anti-shrinkage properties to fabrics, as well as provide static control, fabric softness, maintain the desired color appearance, and fabric anti-wear properties and benefits. In particular, there remains a need for the inclusion of compositions that are capable of removing the colored components of stains, which often remain attached to the fabric being laundered. In addition, there remains a need for improved methods and compositions suitable for textile bleaching.

SUMMARY OF THE INVENTION

The present invention provides methods and compositions comprising at least one thermolysin-like neutral protease enzyme with improved storage stability and/or catalytic activity. In some embodiments, the thermolysin finds use in cleaning and other applications comprising detergent. In some particularly preferred embodiments, the present invention provides methods and compositions comprising thermolysin formulated and/or engineered to resist detergent-induced inactivation.

The present invention provides compositions comprising an isolated thermolysin and a neutral metalloprotease inhibitor, wherein the thermolysin is a *Geobacillus* thermolysin or a *Bacillus* thermolysin. In some embodiments, the compositions of the invention comprise an isolated thermolysin and a neutral metalloprotease inhibitor chosen from phosphoramidon and galardin. In some embodiments, the thermolysin of the compositions of the invention is a *G. caldoproteolyticus* or a *G. stearothermophilus*, thermolysin, while in other embodiments, the thermolysin of the compositions of the invention is a *B. thermoproteolyticus* thermolysin. In some particular embodiments, the compositions of the invention comprise a thermolysin has at least 50% (50 to 100%, preferably at least 55%, 60%, 65%, 70%, 75%, 80%, 85%, 90%, 95%, 96%, 97%, 98%, or 99%) amino acid identity with the thermolysin comprising the amino acid sequence set forth in SEQ ID NO:3. In some other embodiments, the compositions of the invention comprise a thermolysin that comprises the amino acid sequence set forth in SEQ ID NO:3. In yet other embodiments, the compositions of the invention comprise a thermolysin of SEQ ID NO:3.

In addition the present invention provides an isolated thermolysin variant having improved stability and/or performance. In some preferred embodiments, the thermolysin variant is a *Geobacillus* thermolysin variant having an amino acid sequence comprising one or more substitutions at positions chosen from positions equivalent to positions 6, 7, 49, 56, 58, 61, 63, 65, 75, 128, 151, 156, 196, 273, 278, and 280 of the amino acid sequence set forth as SEQ ID NO:3. In a subset of these embodiments, the one or more substitutions comprise one, two, three, four or five substitutions at positions chosen from positions equivalent to positions 6, 7, 49, 56, 58, 61, 63, 65, 75, 128, 151, 156, 196, 273, 278, and 280 of the amino acid sequence set forth as SEQ ID NO:3. In further embodiments, the invention provides an isolated *Geobacillus* thermolysin variant having an amino acid sequence comprising one or more substitutions at positions chosen from positions equivalent to positions 4, 6, 7, 36, 49, 53, 56, 58, 61, 63, 65, 75, 85, 108, 128, 129, 151, 156, 194, 195, 196, 261, 265, 273, 278, 280 and 297 of the amino acid sequence set forth as SEQ ID NO:3, and having improved stability and/or performance. In a subset of these embodiments, the one or more substitutions comprise one, two, three, four or five substitutions at positions chosen from positions equivalent to positions 4, 6, 7, 36, 49, 53, 56, 58, 61, 63, 65, 75, 85, 108, 128, 129, 151, 156, 194, 195, 196, 261, 265, 273, 278, 280 and 297 of the amino acid sequence set forth as SEQ ID NO:3.

In some other embodiments, the invention provides a thermolysin variant that comprises one or more substitutions chosen from the group of the substitutions T006G, T006H, T006I, T006K, T006M, T006N, T006P, T006Q, T006R, T006V, T006W, T006Y, V007F, V007H, V007K, V007L, V007M, V007P, V007Q, V007R, V007T, V007Y, T049G, T049H, T049I, T049K, T049L, T049N, T049P, T049Q, T049W, A058I, A058P, A058R, F063I, F063L, F063P, S065K, S065Y, Y075G, Y075M, Y075T, Q128H, Q128I, Q128L, Q128M, Q128V, Q128Y, Y151D, Y151E, Y151H, Y151K, Y151M, Y151N, Y151Q, Y151R, Y151T, Y151V, Y151W, I156M, I156R, I156T, I156W, G196R, Q273I, Q273P, Q273Y, T278K, T278M, T278P, N280K, N280R, T006A, T006C, T049D, T049I, T049L, T049M, T049N, T049S, A056C, A056R, A056Y, A058S, S065C, S065E, S065I, S065T, S065V, S065Y, Q128C, Q128I, Q128M, Q128T, Q128V, Q128Y, Y151A, Y151C, Y151D, Y151E, Y151H, Y151M, Y151N, Y151Q, Y151R, Y151S, Y151T, Y151V, Y151W, I156E, I156H, I156K, I156M, I156R, I156T, I156W, G196D, G196H, Q273A, Q273N, Q273T, Q273W, Q273Y, T278C, T278H, T278M, T278N, T278S, T278Y, N280E, N280I, N280L, N280M, N280S, T006C, T049D, T049N, T049Q, T049S, A056C, A056E, A058C, A058E, A058E, Q061E, Q061M, S065C, S065D, S065E, S065P, S065V, S065W, S065Y, Q128C, Q128I, Q128M, Q128T, Q128V, Q128Y, Y151A, Y151C, Y151N, Y151S, Y151T, and I156E, as listed in Table 7-1, Table 8-1 and Table 8-2, and that has improved stability and/or performance. In a subset of these embodiments, the one or more substitutions comprise one, two, three, four or five substitutions chosen from the group of substitutions T006G, T006H, T006I, T006K, T006M, T006N, T006P, T006Q, T006R, T006V, T006W, T006Y, V007F, V007H, V007K, V007L, V007M, V007P, V007Q, V007R, V007T, V007Y, T049G, T049H, T049I, T049K, T049L, T049N, T049P, T049Q, T049W, A058I, A058P, A058R, F063I, F063L, F063P, S065K, S065Y, Y075G, Y075M, Y075T, Q128H, Q128I, Q128L, Q128M, Q128V, Q128Y, Y151D, Y151E, Y151H, Y151K, Y151M, Y151N, Y151Q, Y151R, Y151T, Y151V, Y151W, I156M, I156R, I156T, I156W, G196R, Q273I, Q273P, Q273Y, T278K, T278M, T278P, N280K, N280R, T006A, T006C, T049D, T049I, T049L, T049M, T049N, T049S, A056C, A056R, A056Y, A058S, S065C, S065E, S065I, S065T, S065V, S065Y, Q128C, Q128I, Q128M, Q128T, Q128V, Q128Y, Y151A, Y151C, Y151D, Y151E, Y151H, Y151M, Y151N, Y151Q, Y151R, Y151S, Y151T, Y151V, Y151W, I156E, I156H, I156K, I156M, I156R, I156T, I156W, G196D, G196H, Q273A, Q273N, Q273T, Q273W, Q273Y, T278C, T278H, T278M, T278N, T278S, T278Y, N280E, N280I, N280L, N280M, N280S, T006C, T049D, T049N, T049Q, T049S, A056C, A056E, A058C, A058E, A058E, Q061E, Q061M, S065C, S065D, S065E, S065P, S065V, S065W, S065Y, Q128C, Q128I, Q128M, Q128T, Q128V, Q128Y, Y151A, Y151C, Y151N, Y151S, Y151T, and I156E, as listed in Table 7-1, Table 8-1 and Table 8-2.

Moreover the present invention provides an isolated thermolysin variant having improved stability and/or performance as compared to wild-type *Geobacillus* sp. thermolysin (e.g., thermolysin comprising the amino acid sequence set forth as SEQ ID NO:3). In some embodiments, the invention provides an isolated thermolysin variant having improvements that comprise one or more of improved thermostability, improved performance under lower or higher pH conditions, and improved autolytic stability.

In some embodiments, the invention provides a *Bacillus* sp. host cell transformed with a polynucleotide encoding a thermolysin variant having 50 to 99% (at least 55%, 60%, 65%, 70%, 75%, 80%, 85%, 90%, 95%, 96%, 97%, 98%, or 99%) amino acid identity with the amino acid sequence of SEQ ID NO:3.

Also provided by the present invention are methods for producing an enzyme having thermolysin activity, comprising: i) transforming a host cell with an expression vector comprising a polynucleotide encoding a thermolysin variant having 50 to 99% identity (at least 55%, 60%, 65%, 70%, 75%, 80%, 85%, 90%, 95%, 96%, 97%, 98%, or 99%) amino acid identity with the thermolysin comprising the amino acid sequence set forth in SEQ ID NO:3, and ii) cultivating the transformed host cell under conditions suitable for the production of the thermolysin. Optionally, the method of the invention further comprises harvesting the produced thermolysin. In some embodiments, the invention provides for methods for producing an enzyme having thermolysin activity, comprising: i) transforming a host cell with an expression vector comprising a polynucleotide encoding a thermolysin variant having polynucleotide encoding the thermolysin variant has at least 55%, 60%, 65%, 70%, 75%, 80%, 85%, 90%, 95%, 96%, 97%, 98%, or 99% amino acid identity with the thermolysin comprising the amino acid sequence set forth in SEQ ID NO:3, and ii) cultivating the transformed host cell under conditions suitable for the production of the thermolysin. Optionally, the methods further comprise the step of harvesting the produced thermolysin. In some other embodiments, the invention provides a method for producing an enzyme having thermolysin activity, comprising: i) transforming a *Bacillus* species (e.g., *B subtilis*) host cell with an expression vector comprising a polynucleotide encoding a thermolysin variant having 50 to 99% identity (at least 55%, 60%, 65%, 70%, 75%, 80%, 85%, 90%, 95%, 96%, 97%, 98%, or 99%) amino acid identity with the thermolysin comprising the amino acid sequence set forth in SEQ ID NO:3, and ii) cultivating the transformed host cell under conditions suitable for the production of the thermolysin. Optionally, the methods further comprise the step of harvesting the produced thermolysin.

In some embodiments, the present invention provides compositions comprising at least one thermolysin variant obtained from the recombinant *Bacillus* sp. host cell of the present invention. In some embodiments, the composition comprising at least one thermolysin variant further comprises at least one calcium ion and/or zinc ion. In some alternative embodiments, the composition comprising at least one thermolysin variant further comprises at least one stabilizer. In a subset of these embodiments, the stabilizer is chosen from borax, glycerol, zinc ions, calcium ions, and calcium formate. In some embodiments, the stabilizer is at least one competitive inhibitor that stabilizes the thermolysin in the presence of an anionic surfactant. Alternatively, the compositions comprising at least one thermolysin variant, comprise at least one calcium ion and/or zinc ion, in combination with at least one stabilizer. Any one of the stabilizers recited above may be combined with the at least one calcium ion and/or zinc ion to provide the compositions comprising at least one thermolysin variant. In a subset of these embodiments, the stabilizer is chosen from borax, glycerol, zinc ions, calcium ions, and calcium formate. In some other embodiments, the stabilizer is at least one competitive inhibitor that stabilizes the thermolysin in the presence of an anionic surfactant.

In other embodiments, the invention provides a composition comprising at least one thermolysin variant obtained from the recombinant *Bacillus* sp. host cell of the present invention, in combination with at least one additional enzyme or enzyme derivative chosen from proteases, amylases, lipases, mannanases, pectinases, cutinases, oxidoreductases, hemicellulases, and cellulases. In some embodiments, the composition comprising at least one thermolysin variant and at least one additional enzyme or enzyme derivative chosen from proteases, amylases, lipases, mannanases, pectinases, cutinases, oxidoreductases, hemicellulases, and cellulases further comprises at least one stabilizer. In a subset of these embodiments, the stabilizer is chosen from borax, glycerol, zinc ions, calcium ions, and calcium formate. In some embodiments, the stabilizer is at least one competitive inhibitor that stabilizes the thermolysin in the presence of an anionic surfactant. Alternatively, the compositions comprising at least one thermolysin variant, comprise at least one calcium ion and/or zinc ion, in combination with at least one stabilizer. Any one of the stabilizers recited above may be combined with the at least one calcium ion and/or zinc ion to provide the compositions comprising at least one thermolysin variant. In a subset of these embodiments, the stabilizer is chosen from borax, glycerol, zinc ions, calcium ions, and calcium formate. In some other embodiments, the stabilizer is at least one competitive inhibitor that stabilizes the thermolysin in the presence of an anionic surfactant.

In some embodiments, present invention provides a cleaning composition comprising at least one thermolysin variant obtained from the recombinant *Bacillus* sp. host cell of the present invention. In some embodiments, the cleaning composition comprising at least one thermolysin variant, further comprises at least one calcium ion and/or zinc ion. In some alternative embodiments, the cleaning composition comprising at least one thermolysin variant, further comprises at least one stabilizer. In a subset of these embodiments, the stabilizer is chosen from borax, glycerol, zinc ions, calcium ions, and calcium formate. In some embodiments, the stabilizer is at least one competitive inhibitor that stabilizes the thermolysin in the presence of an anionic surfactant. Alternatively, the cleaning compositions comprising at least one thermolysin variant, comprise at least one calcium ion and/or zinc ion, in combination with at least one stabilizer. Any one of the stabilizers recited above may be combined with the at least one calcium ion and/or zinc ion to provide the compositions comprising at least one thermolysin variant. In some embodiments, the stabilizer is at least one competitive inhibitor that stabilizes the thermolysin in the presence of an anionic surfactant.

In other embodiments, the invention provides a cleaning composition comprising at least one thermolysin variant obtained from the recombinant *Bacillus* sp. host cell of the present invention, in combination with at least one additional enzyme or enzyme derivative chosen from proteases, amylases, lipases, mannanases, pectinases, cutinases, oxidoreductases, hemicellulases, and cellulases. In some embodiments, the cleaning compsiton comprising at least one thermolysin variant and at least one additional enzyme or enzyme derivative chosen from proteases, amylases, lipases, mannanases, pectinases, cutinases, oxidoreductases, hemicellulases, and cellulases further comprises at least one stabilizer. In a subset of these embodiments, the stabilizer is chosen from borax, glycerol, zinc ions, calcium ions, and calcium formate. In some embodiments, the stabilizer is at least one competitive inhibitor that stabilizes the thermolysin in the presence of an anionic surfactant. Alternatively, the cleaning compositions comprising at least one thermolysin variant, comprise at least one calcium ion and/or zinc ion, in combination with at least one stabilizer. Any one of the stabilizers recited above may be combined with the at least one calcium ion and/or zinc ion to provide the compositions comprising at least one thermolysin variant. In a subset of these embodiments, the stabilizer is chosen from borax, glycerol, zinc ions, calcium ions, and calcium formate. In some other embodiments, the stabilizer is at least one competitive inhibitor that stabilizes the thermolysin in the presence of an anionic surfactant.

In some embodiments, the present invention provides compositions comprising an isolated thermolysin variant having improved stability and/or performance. In some embodiments, the composition comprising the isolated thermolysin variant having improved stability and/or performance, further comprises at least one calcium ion and/or zinc ion. In some alternative embodiments, the composition comprising the isolated thermolysin variants having improved stability and/or performance, further comprises at least one stabilizer. In a subset of these embodiments, the stabilizer is chosen from borax, glycerol, zinc ions, calcium ions, and calcium formate. In some embodiments, the stabilizer is at least one competitive inhibitor that stabilizes the thermolysin in the presence of an anionic surfactant. Alternatively, the compositions comprising the isolated thermolysin variant having improved stability and/or performance, comprise at least one calcium ion and/or zinc ion, in combination with at least one stabilizer. Any one of the stabilizers recited above may be combined with the at least one calcium ion and/or zinc ion to provide the compositions comprising at least one thermolysin variant. In a subset of these embodiments, the stabilizer is chosen from borax, glycerol, zinc ions, calcium ions, and calcium formate. In some other embodiments, the stabilizer is at least one competitive inhibitor that stabilizes the thermolysin in the presence of an anionic surfactant. In some embodiments, the thermolysin variant having improved stability and/or performance is a *Geobacillus* thermolysin variant having an amino acid sequence comprising one or more substitutions at positions chosen from positions equivalent to positions 6, 7, 49, 56, 58, 61, 63, 65, 75, 128, 151, 156, 196, 273, 278, and 280 of the amino acid sequence set forth as SEQ ID NO:3. In a subset of these embodiments, the one or more substitutions comprise one, two, three, four or five substitutions at positions chosen from positions equivalent to positions 6, 7, 49, 56, 58, 61, 63, 65, 75, 128, 151, 156, 196, 273, 278, and 280 of the amino acid sequence set forth as SEQ ID NO:3. In further embodiments, the invention provides an isolated *Geobacillus* thermolysin variant having an amino acid sequence comprising one or more substitutions at positions chosen from positions equivalent to positions 4, 6, 7, 36, 49, 53, 56, 58, 61, 63, 65, 75, 85, 108, 128, 129, 151, 156, 194, 195, 196, 261, 265, 273, 278, 280 and 297 of the amino acid sequence set forth as SEQ ID NO:3, and having improved stability and/or performance. In a subset of these embodiments, the one or more substitutions comprise one, two, three, four or five substitutions at positions chosen from positions equivalent to positions 4, 6, 7, 36, 49, 53, 56, 58, 61, 63, 65, 75, 85, 108, 128, 129, 151, 156, 194, 195, 196, 261, 265, 273, 278, 280 and 297 of the amino acid sequence set forth as SEQ ID NO:3. In some other embodiments, the thermolysin variant having improved stability and/or performance comprises one or more substitutions chosen from the group of the substitutions T006G, T006H, T006I, T006K, T006M, T006N, T006P, T006Q, T006R, T006V, T006W, T006Y, V007F, V007H, V007K, V007L, V007M, V007P, V007Q, V007R, V007T, V007Y, T049G, T049H, T049I, T049K, T049L, T049N, T049P, T049Q, T049W, A058I, A058P, A058R, F063I, F063L, F063P, S065K, S065Y, Y075G, Y075M, Y075T, Q128H, Q128I, Q128L, Q128M, Q128V, Q128Y, Y151D, Y151E, Y151H, Y151K, Y151M, Y151N, Y151Q, Y151R, Y151T, Y151V, Y151W, I156M, I156R, I156T, I156W, G196R, Q273I, Q273P, Q273Y, T278K, T278M, T278P, N280K, N280R, T006A, T006C, T049D, T049I, T049L, T049M, T049N, T049S, A056C, A056R, A056Y, A058S, S065C, S065E, S065I, S065T, S065V, S065Y, Q128C, Q128I, Q128M, Q128T, Q128V, Q128Y, Y151A, Y151C, Y151D, Y151E, Y151H, Y151M, Y151N, Y151Q, Y151R, Y151S, Y151T, Y151V, Y151W, I156E, I156H, I156K, I156M, I156R, I156T, I156W, G196D, G196H, Q273A, Q273N, Q273T, Q273W, Q273Y, T278C, T278H, T278M, T278N, T278S, T278Y, N280E, N280I, N280L, N280M, N280S, T006C, T049D, T049N, T049Q, T049S, A056C, A056E, A058C, A058E, Q061E, Q061M, S065C, S065D, S065E, S065P, S065V, S065W, S065Y, Q128C, Q128I, Q128M, Q128T, Q128V, Q128Y, Y151A, Y151C, Y151N, Y151S, Y151T, and I156E, as listed in Table 7-1, Table 8-1 and Table 8-2. In a subset of these embodiments, the one or more substitutions comprise one, two, three, four or five substitutions chosen from the group of substitutions T006G, T006H, T006I, T006K, T006M, T006N, T006P, T006Q, T006R, T006V, T006W, T006Y, V007F, V007H, V007K, V007L, V007M, V007P, V007Q, V007R, V007T, V007Y, T049G, T049H, T049I, T049K, T049L, T049N, T049P, T049Q, T049W, A058I, A058P, A058R, F063I, F063L, F063P, S065K, S065Y, Y075G, Y075M, Y075T, Q128H, Q128I, Q128L, Q128M, Q128V, Q128Y, Y151D, Y151E, Y151H, Y151K, Y151M, Y151N, Y151Q, Y151R, Y151T, Y151V, Y151W, I156M, I156R, I156T, I156W, G196R, Q273I, Q273P, Q273Y, T278K, T278M, T278P, N280K, N280R, T006A, T006C, T049D, T049I, T049L, T049M, T049N, T049S, A056C, A056R, A056Y, A058S, S065C, S065E, S065I, S065T, S065V, S065Y, Q128C, Q128I, Q128M, Q128T, Q128V, Q128Y, Y151A, Y151C, Y151D, Y151E, Y151H, Y151M, Y151N, Y151Q, Y151R, Y151S, Y151T, Y151V, Y151W, I156E, I156H, I156K, I156M, I156R, I156T, I156W, G196D, G196H, Q273A, Q273N, Q273T, Q273W, Q273Y, T278C, T278H, T278M, T278N, T278S, T278Y, N280E, N280I, N280L, N280M, N280S, T006C, T049D, T049N, T049Q, T049S, A056C, A056E, A058C, A058E, Q061E, Q061M, S065C, S065D, S065E, S065P, S065V, S065W, S065Y, Q128C, Q128I, Q128M, Q128T, Q128V, Q128Y, Y151A, Y151C, Y151N, Y151S, Y151T, and I156E, as listed in Table 7-1, Table 8-1 and Table 8-2.

In other embodiments, the invention provides a composition comprising an isolated thermolysin variant having improved stability and/or performance, in combination with at least one additional enzyme or enzyme derivative chosen from proteases, amylases, lipases, mannanases, pectinases, cutinases, oxidoreductases, hemicellulases, and cellulases. In some embodiments, the composition comprising the isolated thermolysin variant having improved stability and/or performance, and at least one additional enzyme or enzyme derivative chosen from proteases, amylases, lipases, mannanases, pectinases, cutinases, oxidoreductases, hemicellulases, and cellulases, further comprises at least one stabilizer. In a subset of these embodiments, the stabilizer is chosen from borax, glycerol, zinc ions, calcium ions, and calcium formate. In some embodiments, the stabilizer is at least one competitive inhibitor that stabilizes the thermolysin in the presence of an anionic surfactant. Alternatively, the compositions comprising isolated thermolysin variants having improved stability and/or performance, comprise at least one calcium ion and/or zinc ion, in combination with at least one stabilizer. Any one of the stabilizers recited above may be combined with the at least one calcium ion and/or zinc ion to provide the compositions comprising at least one thermolysin variant. In a subset of these embodiments, the stabilizer is chosen from borax, glycerol, zinc ions, calcium ions, and calcium formate. In some other embodiments, the stabilizer is at least one competitive inhibitor that stabilizes the thermolysin in the presence of an anionic surfactant. In some embodiments, the thermolysin variant having improved stability and/or performance is a *Geobacillus* thermolysin variant having an amino acid sequence comprising one or more substitutions at positions chosen from positions equivalent to positions 6, 7, 49, 56, 58, 61, 63, 65, 75, 128, 151, 156, 196, 273, 278, and 280 of the amino acid sequence set forth as SEQ ID NO:3. In a subset of these embodiments, the one or more substitutions comprise one, two, three, four or five substitutions at positions chosen from positions equivalent to positions 6, 7, 49, 56, 58, 61, 63, 65, 75, 128, 151, 156, 196, 273, 278, and 280 of the amino acid sequence set forth as SEQ ID NO:3. In further embodiments, the invention provides an isolated *Geobacillus* thermolysin variant having an amino acid sequence comprising one or more substitutions at positions chosen from positions equivalent to positions 4, 6, 7, 36, 49, 53, 56, 58, 61, 63, 65, 75, 85, 108, 128, 129, 151, 156, 194, 195, 196, 261, 265, 273, 278, 280 and 297 of the amino acid sequence set forth as SEQ ID NO:3, and having improved stability and/or performance. In a subset of these embodiments, the one or more substitutions comprise one, two, three, four or five substitutions at positions chosen from positions equivalent to positions 4, 6, 7, 36, 49, 53, 56, 58, 61, 63, 65, 75, 85, 108, 128, 129, 151, 156, 194, 195, 196, 261, 265, 273, 278, 280 and 297 of the amino acid sequence set forth as SEQ ID NO:3. In some other embodiments, the thermolysin variant having improved stability and/or performance comprises one or more substitutions chosen from the group of the substitutions T006G, T006H, T006I, T006K, T006M, T006N, T006P, T006Q, T006R, T006V, T006W, T006Y, V007F, V007H, V007K, V007L, V007M, V007P, V007Q, V007R, V007T, V007Y, T049G, T049H, T049I, T049K, T049L, T049N, T049P, T049Q, T049W, A058I, A058P, A058R, F063I, F063L, F063P, S065K, S065Y, Y075G, Y075M, Y075T, Q128H, Q128I, Q128L, Q128M, Q128V, Q128Y, Y151D, Y151E, Y151H, Y151K, Y151M, Y151N, Y151Q, Y151R, Y151T, Y151V, Y151W, I156M, I156R, I156T, I156W, G196R, Q273I, Q273P, Q273Y, T278K, T278M, T278P, N280K, N280R, T006A, T006C, T049D, T049I, T049L, T049M, T049N, T049S, A056C, A056R, A056Y, A058S, S065C, S065E, S065I, S065T, S065V, S065Y, Q128C, Q128I, Q128M, Q128T, Q128V, Q128Y, Y151A, Y151C, Y151D, Y151E, Y151H, Y151M, Y151N, Y151Q, Y151R, Y151S, Y151T, Y151V, Y151W, I156E, I156H, I156K, I156M, I156R, I156T, I156W, G196D, G196H, Q273A, Q273N, Q273T, Q273W, Q273Y, T278C, T278H, T278M, T278N, T278S, T278Y, N280E, N280I, N280L, N280M, N280S, T006C, T049D, T049N, T049Q, T049S, A056C, A056E, A058C, A058E, Q061E, Q061M, S065C, S065D, S065E, S065P, S065V, S065W, S065Y, Q128C, Q128I, Q128M, Q128T, Q128V, Q128Y, Y151A, Y151C, Y151N, Y151S, Y151T, and I156E, as listed in Table 7-1, Table 8-1 and Table 8-2. In a subset of these embodiments, the one or more substitutions comprise one, two, three, four or five substitutions chosen from the group of substitutions T006G, T006H, T006I, T006K, T006M, T006N, T006P, T006Q, T006R, T006V, T006W, T006Y, V007F, V007H, V007K, V007L, V007M, V007P, V007Q, V007R, V007T, V007Y, T049G, T049H, T049I, T049K, T049L, T049N, T049P, T049Q, T049W, A058I, A058P, A058R, F063I, F063L, F063P, S065K, S065Y, Y075G, Y075M, Y075T, Q128H, Q128I, Q128L, Q128M, Q128V, Q128Y, Y151D, Y151E, Y151H, Y151K, Y151M, Y151N, Y151Q, Y151R, Y151T, Y151V, Y151W, I156M, I156R, I156T, I156W, G196R, Q273I, Q273P, Q273Y, T278K, T278M, T278P, N280K, N280R, T006A, T006C, T049D, T049I, T049L, T049M, T049N, T049S, A056C, A056R, A056Y, A058S, S065C, S065E, S065I, S065T, S065V, S065Y, Q128C, Q128I, Q128M, Q128T, Q128V, Q128Y, Y151A, Y151C, Y151D, Y151E, Y151H, Y151M, Y151N, Y151Q, Y151R, Y151S, Y151T, Y151V, Y151W, I156E, I156H, I156K, I156M, I156R, I156T, I156W, G196D, G196H, Q273A, Q273N, Q273T, Q273W, Q273Y, T278C, T278H, T278M, T278N, T278S, T278Y, N280E, N280I, N280L, N280M, N280S, T006C, T049D, T049N, T049Q, T049S, A056C, A056E, A058C, A058E, Q061E, Q061M, S065C, S065D, S065E, S065P, S065V, S065W, S065Y, Q128C, Q128I, Q128M, Q128T, Q128V, Q128Y, Y151A, Y151C, Y151N, Y151S, Y151T, and I156E, as listed in Table 7-1, Table 8-1 and Table 8-2.

In some embodiments, the present invention provides cleaning compositions comprising an isolated thermolysin variant having improved stability and/or performance. In some embodiments, the cleaning composition comprising the isolated thermolysin variant having improved stability and/or performance, further comprises at least one calcium ion and/or zinc ion. In some alternative embodiments, the cleaning composition comprising the isolated thermolysin variant having improved stability and/or performance, further comprises at least one stabilizer. In a subset of these embodiments, the stabilizer is chosen from borax, glycerol, zinc ions, calcium ions, and calcium formate. In some embodiments, the stabilizer is at least one competitive inhibitor that stabilizes the thermolysin in the presence of an anionic surfactant. Alternatively, the cleaning composition comprising the isolated thermolysin variant having improved stability and/or performance, comprises at least one calcium ion and/or zinc ion, in combination with at least one stabilizer. Any one of the stabilizers recited above may be combined with the at least one calcium ion and/or zinc ion to provide the compositions comprising at least one thermolysin variant. In a subset of these embodiments, the stabilizer is chosen from borax, glycerol, zinc ions, calcium ions, and calcium formate. In some other embodiments, the stabilizer is at least one competitive inhibitor that stabilizes the thermolysin in the presence of an anionic surfactant. In some embodiments, the thermolysin variant comprised in the cleaning compositions and having improved stability and/or performance is a *Geobacillus* thermolysin variant having an amino acid sequence comprising one or more substitutions at positions chosen from positions equivalent to positions 6, 7, 49, 56, 58, 61, 63, 65, 75, 128, 151, 156, 196, 273, 278, and 280 of the amino acid sequence set forth as SEQ ID NO:3. In a subset of these embodiments, the one or more substitutions comprise one, two, three, four or five substitutions at positions chosen from positions equivalent to positions 6, 7, 49, 56, 58, 61, 63, 65, 75, 128, 151, 156, 196, 273, 278, and 280 of the amino acid sequence set forth as SEQ ID NO:3. In further embodiments, the thermolysin variant comprised in the cleaning compositions and having improved stability and/or performance is a *Geobacillus* thermolysin variant having an amino acid sequence comprising one or more substitutions at positions chosen from positions equivalent to positions 4, 6, 7, 36, 49, 53, 56, 58, 61, 63, 65, 75, 85, 108, 128, 129, 151, 156, 194, 195, 196, 261, 265, 273, 278, 280 and 297 of the amino acid sequence set forth as SEQ ID NO:3, and having improved stability and/or performance. In a subset of these embodiments, the one or more substitutions comprise one, two, three, four or five substitutions at positions chosen from positions equivalent to positions 4, 6, 7, 36, 49, 53, 56, 58, 61, 63, 65, 75, 85, 108, 128, 129, 151, 156, 194, 195, 196, 261, 265, 273, 278, 280 and 297 of the amino acid sequence set forth as SEQ ID NO:3. In some other embodiments, the thermolysin variant comprised in the cleaning compositions and having improved stability and/or performance is a *Geobacillus* thermolysin variant having an amino acid sequence comprising one or more substitutions chosen from the group of the substitutions T006G, T006H, T006I, T006K, T006M, T006N, T006P, T006Q, T006R, T006V, T006W, T006Y, V007F, V007H, V007K, V007L, V007M, V007P, V007Q, V007R, V007T, V007Y, T049G, T049H, T049I, T049K, T049L, T049N, T049P, T049Q, T049W, A058I, A058P, A058R, F063I, F063L, F063P, S065K, S065Y, Y075G, Y075M, Y075T, Q128H, Q128I, Q128L, Q128M, Q128V, Q128Y, Y151D, Y151E, Y151H, Y151K, Y151M, Y151N, Y151Q, Y151R, Y151T, Y151V, Y151W, I156M, I156R, I156T, I156W, G196R, Q273I, Q273P, Q273Y, T278K, T278M, T278P, N280K, N280R, T006A, T006C, T049D, T049I, T049L, T049M, T049N, T049S, A056C, A056R, A056Y, A058S, S065C, S065E, S065I, S065T, S065V, S065Y, Q128C, Q128I, Q128M, Q128T, Q128V, Q128Y, Y151A, Y151C, Y151D, Y151E, Y151H, Y151M, Y151N, Y151Q, Y151R, Y151S, Y151T, Y151V, Y151W, I156E, I156H, I156K, I156M, I156R, I156T, I156W, G196D, G196H, Q273A, Q273N, Q273T, Q273W, Q273Y, T278C, T278H, T278M, T278N, T278S, T278Y, N280E, N280I, N280L, N280M, N280S, T006C, T049D, T049N, T049Q, T049S, A056C, A056E, A058C, A058E, Q061E, Q061M, S065C, S065D, S065E, S065P, S065V, S065W, S065Y, Q128C, Q128I, Q128M, Q128T, Q128V, Q128Y, Y151A, Y151C, Y151N, Y151S, Y151T, and I156E, as listed in Table 7-1, Table 8-1 and Table 8-2. In a subset of these embodiments, the one or more substitutions comprise one, two, three, four or five substitutions chosen from the group of substitutions T006G, T006H, T006I, T006K, T006M, T006N, T006P, T006Q, T006R, T006V, T006W, T006Y, V007F, V007H, V007K, V007L, V007M, V007P, V007Q, V007R, V007T, V007Y, T049G, T049H, T049I, T049K, T049L, T049N, T049P, T049Q, T049W, A058I, A058P, A058R, F063I, F063L, F063P, S065K, S065Y, Y075G, Y075M, Y075T, Q128H, Q128I, Q128L, Q128M, Q128V, Q128Y, Y151D, Y151E, Y151H, Y151K, Y151M, Y151N, Y151Q, Y151R, Y151T, Y151V, Y151W, I156M, I156R, I156T, I156W, G196R, Q273I, Q273P, Q273Y, T278K, T278M, T278P, N280K, N280R, T006A, T006C, T049D, T049I, T049L, T049M, T049N, T049S, A056C, A056R, A056Y, A058S, S065C, S065E, S065I, S065T, S065V, S065Y, Q128C, Q128I, Q128M, Q128T, Q128V, Q128Y, Y151A, Y151C, Y151D, Y151E, Y151H, Y151M, Y151N, Y151Q, Y151R, Y151S, Y151T, Y151V, Y151W, I156E, I156H, I156K, I156M, I156R, I156T, I156W, G196D, G196H, Q273A, Q273N, Q273T, Q273W, Q273Y, T278C, T278H, T278M, T278N, T278S, T278Y, N280E, N280I, N280L, N280M, N280S, T006C, T049D, T049N, T049Q, T049S, A056C, A056E, A058C, A058E, Q061E, Q061M, S065C, S065D, S065E, S065P, S065V, S065W, S065Y, Q128C, Q128I, Q128M, Q128T, Q128V, Q128Y, Y151A, Y151C, Y151N, Y151S, Y151T, and I156E, as listed in Table 7-1, Table 8-1 and Table 8-2.

In other embodiments, the invention provides a cleaning composition comprising an isolated thermolysin variant having improved stability and/or performance, in combination with at least one additional enzyme or enzyme derivative chosen from proteases, amylases, lipases, mannanases, pectinases, cutinases, oxidoreductases, hemicellulases, and cellulases. In some embodiments, the cleaning composition comprises the isolated thermolysin variant having improved stability and/or performance, and at least one additional enzyme or enzyme derivative chosen from proteases, amylases, lipases, mannanases, pectinases, cutinases, oxidoreductases, hemicellulases, and cellulases further comprises at least one stabilizer. In a subset of these embodiments, the stabilizer is chosen from borax, glycerol, zinc ions, calcium ions, and calcium formate. In some embodiments, the stabilizer is at least one competitive inhibitor that stabilizes the thermolysin in the presence of an anionic surfactant. Alternatively, the cleaning compositions comprising the isolated thermolysin variant having improved stability and/or performance, comprise at least one calcium ion and/or zinc ion, in combination with at least one stabilizer. Any one of the stabilizers recited above may be combined with the at least one calcium ion and/or zinc ion to provide the compositions comprising at least one thermolysin variant. In a subset of these embodiments, the stabilizer is chosen from borax, glycerol, zinc ions, calcium ions, and calcium formate. In some other embodiments, the stabilizer is at least one competitive inhibitor that stabilizes the thermolysin in the presence of an anionic surfactant. In some embodiments, the thermolysin variant comprised in the cleaning compositions and having improved stability and/or performance is a Geobacillus thermolysin variant having an amino acid sequence comprising one or more substitutions at positions chosen from positions equivalent to positions 6, 7, 49, 56, 58, 61, 63, 65, 75, 128, 151, 156, 196, 273, 278, and 280 of the amino acid sequence set forth as SEQ ID NO:3. 9 In a subset of these embodiments, the one or more substitutions comprise one, two, three, four or five substitutions at positions equivalent to positions 6, 7, 49, 56, 58, 61, 63, 65, 75, 128, 151, 156, 196, 273, 278, and 280 of the amino acid sequence set forth as SEQ ID NO:3. In further embodiments, the thermolysin variant comprised in the cleaning compositions and having improved stability and/or performance is a Geobacillus thermolysin variant having an amino acid sequence comprising one or more substitutions at positions chosen from positions equivalent to positions 4, 6, 7, 36, 49, 53, 56, 58, 61, 63, 65, 75, 85, 108, 128, 129, 151, 156, 194, 195, 196, 261, 265, 273, 278, 280 and 297 of the amino acid sequence set forth as SEQ ID NO:3, and having improved stability and/or performance. In a subset of these embodiments, the one or more substitutions comprise one, two, three, four or five substitutions at positions chosen from positions equivalent to positions 4, 6, 7, 36, 49, 53, 56, 58, 61, 63, 65, 75, 85, 108, 128, 129, 151, 156, 194, 195, 196, 261, 265, 273, 278, 280 and 297 of the amino acid sequence set forth as SEQ ID NO:3. In some other embodiments, the thermolysin variant comprised in the cleaning compositions and having improved stability and/or performance is a Geobacillus thermolysin variant having an amino acid sequence comprising one or more substitutions chosen from the group of the substitutions T006G, T006H, T006I, T006K, T006M, T006N, T006P, T006Q, T006R, T006V, T006W, T006Y, V007F, V007H, V007K, V007L, V007M, V007P, V007Q, V007R, V007T, V007Y, T049G, T049H, T049I, T049K, T049L, T049N, T049P, T049Q, T049W, A058I, A058P, A058R, F063I, F063L, F063P, S065K, S065Y, Y075G, Y075M, Y075T, Q128H, Q128I, Q128L, Q128M, Q128V, Q128Y, Y151D, Y151E, Y151H, Y151K, Y151M, Y151N, Y151Q, Y151R, Y151T, Y151V, Y151W, I156M, I156R, I156T, I156W, G196R, Q273I, Q273P, Q273Y, T278K, T278M, T278P, N280K, N280R, T006A, T006C, T049D, T049I, T049L, T049M, T049N, T049S, A056C, A056R, A056Y, A058S, S065C, S065E, S065I, S065T, S065V, S065Y, Q128C, Q128I, Q128M, Q128T, Q128V, Q128Y, Y151A, Y151C, Y151D, Y151E, Y151H, Y151M, Y151N, Y151Q, Y151R, Y151S, Y151T, Y151V, Y151W, I156E, I156H, I156K, I156M, I156R, I156T, I156W, G196D, G196H, Q273A, Q273N, Q273T, Q273W, Q273Y, T278C, T278H, T278M, T278N, T278S, T278Y, N280E, N280I, N280L, N280M, N280S, T006C, T049D, T049N, T049Q, T049S, A056C, A056E, A058C, A058E, Q061E, Q061M, S065C, S065D, S065E, S065P, S065V, S065W, S065Y, Q128C, Q128I, Q128M, Q128T, Q128V, Q128Y, Y151A, Y151C, Y151N, Y151S, Y151T, and I156E, as listed in Table 7-1, Table 8-1 and Table 8-2. In a subset of these embodiments, the one or more substitutions comprise one, two, three, four or five substitutions chosen from the group of substitutions T006G, T006H, T006I, T006K, T006M, T006N, T006P, T006Q, T006R, T006V, T006W, T006Y, V007F, V007H, V007K, V007L, V007M, V007P, V007Q, V007R, V007T, V007Y, T049G, T049H, T049I, T049K, T049L, T049N, T049P, T049Q, T049W, A058I, A058P, A058R, F063I, F063L, F063P, S065K, S065Y, Y075G, Y075M, Y075T, Q128H, Q128I, Q128L, Q128M, Q128V, Q128Y, Y151D, Y151E, Y151H, Y151K, Y151M, Y151N, Y151Q, Y151R, Y151T, Y151V, Y151W, I156M, I156R, I156T, I156W, G196R, Q273I, Q273P, Q273Y, T278K, T278M, T278P, N280K, N280R, T006A, T006C, T049D, T049I, T049L, T049M, T049N, T049S, A056C, A056R, A056Y, A058S, S065C, S065E, S065I, S065T, S065V, S065Y, Q128C, Q128I, Q128M, Q128T, Q128V, Q128Y, Y151A, Y151C, Y151D, Y151E, Y151H, Y151M, Y151N, Y151Q, Y151R, Y151S, Y151T, Y151V, Y151W, I156E, I156H, I156K, I156M, I156R, I156T, I156W, G196D, G196H, Q273A, Q273N, Q273T, Q273W, Q273Y, T278C, T278H, T278M, T278N, T278S, T278Y, N280E, N280I, N280L, N280M, N280S, T006C, T049D, T049N, T049Q, T049S, A056C, A056E, A058C, A058E, Q061E, Q061M, S065C, S065D, S065E, S065P, S065V, S065W, S065Y, Q128C, Q128I, Q128M, Q128T, Q128V, Q128Y, Y151A, Y151C, Y151N, Y151S, Y151T, and I156E, as listed in Table 7-1, Table 8-1 and Table 8-2.

In some embodiments, any one of the cleaning compositions comprising a thermolysin variant having improved stability and/or performance as recited herein, is a detergent.

In some embodiments, the compositions are detergent compositions. In other embodiments, the compositions are liquid.

In some embodiments, the present invention provides a composition comprising a thermolysin variant having improved stability and/or performance e.g. a cleaning composition, comprising at least about 0.0001 weight percent of the thermolysin variant; or from about 0.001 to about 0.5 weight percent of the same thermolysin variant. Optionally, the composition of the present invention, which comprises a thermolysin variant having improved stability and/or performance e.g a cleaning composition, further comprises at least one adjunct ingredient. Alternatively, in some other embodiments, the composition e.g. a cleaning composition, further comprises a sufficient amount of a pH modifier to provide the composition with a neat pH of from about 3 to about 5, the composition being essentially free of materials that hydrolyze at a pH of from about pH 3 to about pH 5. In some embodiments, the materials that hydrolyze at a pH of from about pH 3 to about pH 5 comprise at least one surfactant. In some preferred embodiments, the surfactant is a sodium alkyl sulfate surfactant comprising an ethylene oxide moiety. In some embodiments, the composition comprising a thermolysin variant having improved stability and/or performance e.g. a cleaning composition, is a detergent.

In addition, the present invention provides animal feed compositions comprising an isolated thermolysin variant having improved stability and/or performance. In further embodiments textile processing compositions are provided comprising an isolated thermolysin variant having improved stability and/or performance. In still further embodiments leather processing compositions are provided comprising an isolated thermolysin variant having improved stability and/or performance.

Moreover, the present invention provides methods of cleaning, comprising the step of contacting a surface and/or an article comprising a fabric with a cleaning composition comprising an isolated thermolysin variant having improved stability and/or performance. In some embodiments, the methods of cleaning further comprise the step of rinsing the surface and/or material after contacting the surface or material with the cleaning composition.

BRIEF DESCRIPTION OF THE DRAWINGS

FIG. 1 provides the amino acid sequence (SEQ ID NO:3) of the mature form of *Geobacillus* caldoproteolyticus thermolysin-like neutral metalloprotease enzyme (also referred to herein as thermolysin, Proteinase-T or PrT).

FIG. 2 provides a map of the pHPLT plasmid.

Figure 4A:
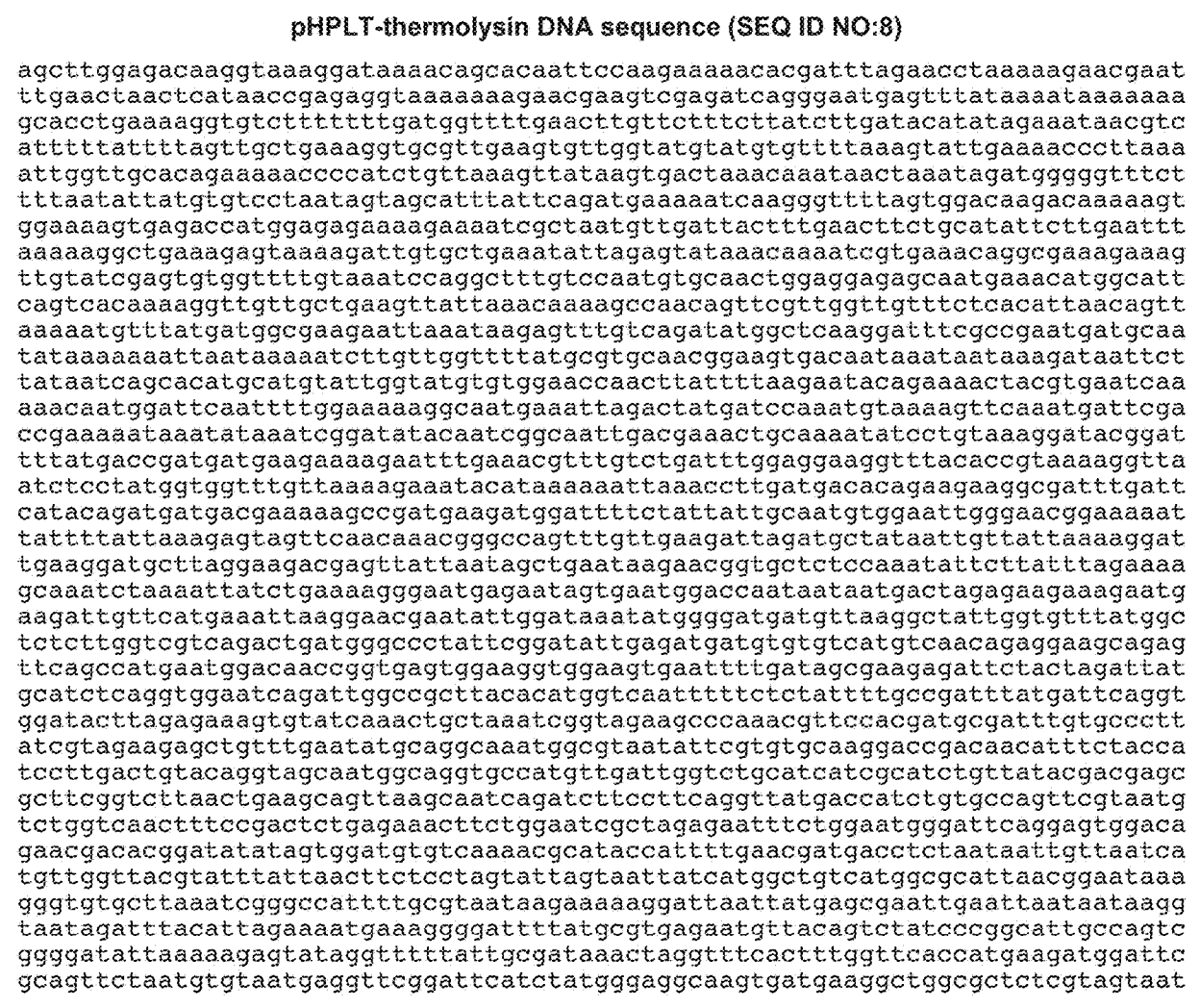

FIG. 4A-B provides the nucleic acid sequence (SEQ ID NO:8) of the pHPLT-thermolysin expression vector.

Figures 9, 9A:
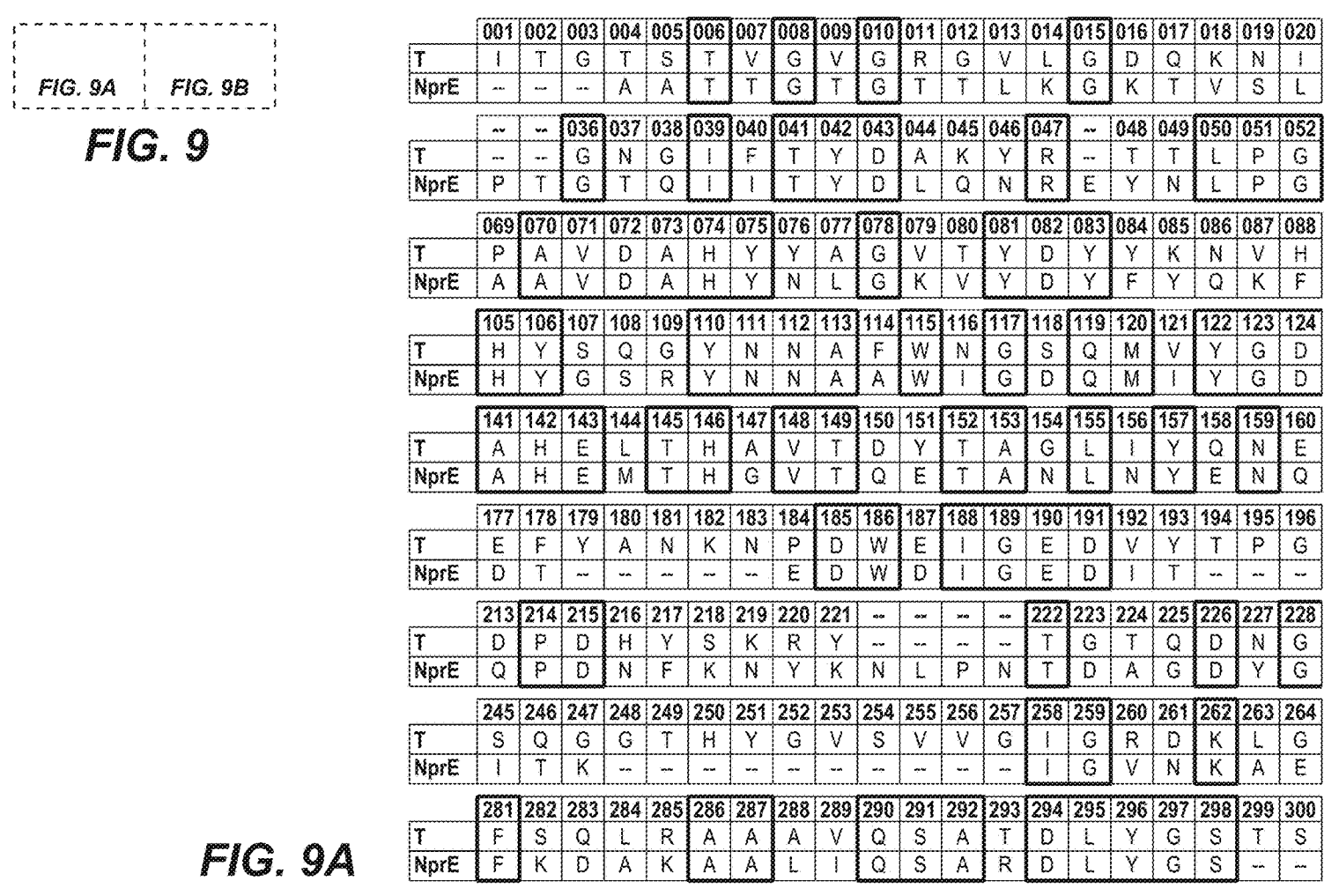

FIGS. 9A-B provide an alignment of the thermolysin (T) and NprE amino acid sequences. The thermolysin sequence is set forth as SEQ ID NO:3, while the NprE sequence is set forth as SEQ ID NO:9.

GENERAL DESCRIPTION OF THE INVENTION

Figure 3:
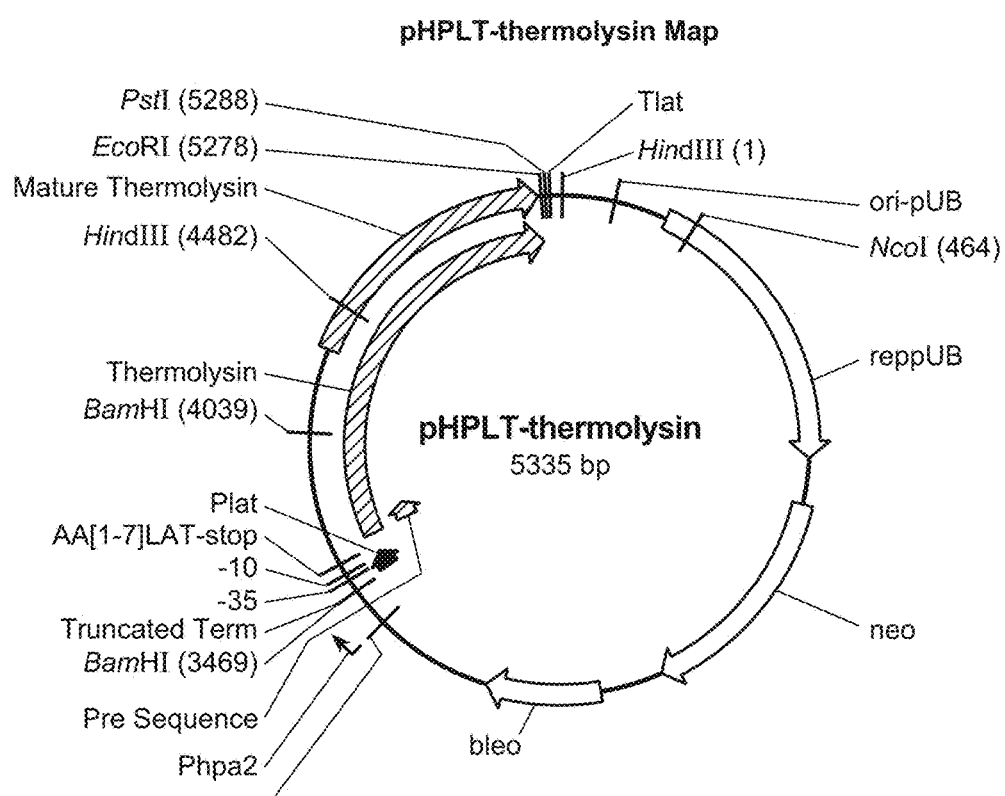
FIG. 3 provides a map of the pHPLT-thermolysin expression vector.

The present invention provides methods and compositions comprising at least one thermolysin-like neutral protease enzyme with improved storage stability and/or catalytic activity. In some embodiments, the thermolysin finds use in cleaning and other applications comprising detergent. In some particularly preferred embodiments, the present invention provides methods and compositions comprising thermolysin formulated and/or engineered to resist detergent-induced inactivation.

Unless otherwise indicated, the practice of the present invention involves conventional techniques commonly used in molecular biology, microbiology, and recombinant DNA, which are within the skill of the art. Such techniques are known to those of skill in the art and are described in numerous texts and reference works (See e.g., Sambrook et al., "Molecular Cloning: A Laboratory Manual," Second Edition, Cold Spring Harbor, 1989; and Ausubel et al., "Current Protocols in Molecular Biology," 1987). All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art to which this invention pertains. For example, Singleton and Sainsbury, *Dictionary of Microbiology and Molecular Biology,* 2d Ed., John Wiley and Sons, NY (1994); and Hale and Marham, *The Harper Collins Dictionary of Biology,* Harper Perennial, N.Y. (1991) provide those of skill in the art with a general dictionaries of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole.

Also, as used herein, the singular "a", "an" and "the" includes the plural reference unless the context clearly indicates otherwise. Numeric ranges are inclusive of the numbers defining the range. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

Furthermore, the headings provided herein are not limitations of the various aspects or embodiments of the invention, which can be had by reference to the specification as a whole. Accordingly, the terms defined immediately below are more fully defined by reference to the specification as a whole. Nonetheless, in order to facilitate understanding of the invention, a number of terms are defined below.

Definitions

Unless defined otherwise herein, all technical and scientific terms used herein have the same meaning as commonly understood by one of ordinary skill in the art to which this invention pertains. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular terms "a," "an," and "the" include the plural reference unless the context clearly indicates otherwise. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited are, in relevant part, incorporated herein by reference; the citation of any document is not to be construed as an admission that it is prior art with respect to the present invention.

As used herein, the terms "protease," and "proteolytic activity" refer to a protein or peptide exhibiting the ability to hydrolyze peptides or substrates having peptide linkages. Many well known procedures exist for measuring proteolytic activity (Kalisz, "Microbial Proteinases," In: Fiechter (ed.), *Advances in Biochemical Engineering/Biotechnology*, 1988). For example, proteolytic activity may be ascertained by comparative assays, which analyze the respective protease's ability to hydrolyze a commercial substrate. Exemplary substrates useful in such analysis of protease or proteolytic activity, include, but are not limited to di-methyl casein (Sigma C-9801), bovine collagen (Sigma C-9879), bovine elastin (Sigma E-1625), and bovine keratin (ICN Biomedical 902111). Colorimetric assays utilizing these substrates are well known in the art (See e.g., WO 99/34011; and U.S. Pat. No. 6,376,450, both of which are incorporated herein by reference. The pNA assay (See e.g., Del Mar et al., Anal Biochem, 99:316-320, 1979) also finds use in determining the active enzyme concentration for fractions collected during gradient elution. This assay measures the rate at which p-nitroaniline is released as the enzyme hydrolyzes the soluble synthetic substrate, succinyl-alanine-alanine-proline-phenylalanine-p-nitroanilide (sAAPF-pNA). The rate of production of yellow color from the hydrolysis reaction is measured at 410 nm on a spectrophotometer and is proportional to the active enzyme concentration. In addition, absorbance measurements at 280 nm can be used to determine the total protein concentration. The active enzyme/total-protein ratio gives the enzyme purity.

As used herein, the terms "NprE protease," and "NprE," refer to the neutral metalloproteases described herein. In some preferred embodiments, the NprE protease is the protease designated herein as purified MULTIFECT® Neutral or PMN obtained from *Bacillus amyloliquefaciens*. Thus, in some embodiments, the term "PMN protease" refers to a naturally occurring mature protease derived from *Bacillus amyloliquefaciens*. In alternative embodiments, the present invention provides portions of the NprE protease.

The term "*Bacillus* protease homologues" refers to naturally occurring proteases having substantially identical amino acid sequences to the mature protease derived from *Bacillus thermoproteolyticus* thermolysin or polynucleotide sequences which encode for such naturally occurring proteases, and which proteases retain the functional characteristics of a neutral metalloprotease encoded by such nucleic acids.

As used herein, the term "thermolysin variant," is used in reference to proteases that are similar to the wild-type thermolysin, particularly in their function, but have mutations in their amino acid sequence that make them different in sequence from the wild-type protease.

As used herein, "*Bacillus* ssp." refers to all of the species within the genus "*Bacillus*," which are Gram-positive bacteria classified as members of the Family Bacillaceae, Order Bacillales, Class Bacilli. The genus "*Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

Related (and derivative) proteins comprise "variant proteins." In some preferred embodiments, variant proteins differ from a parent protein and one another by a small number of amino acid residues. The number of differing amino acid residues may be one or more, preferably 1, 2, 3, 4, 5, 10, 15, 20, 30, 40, 50, or more amino acid residues. In some preferred embodiments, the number of different amino acids between variants is between 1 and 10. In some particularly preferred embodiments, related proteins and particularly variant proteins comprise at least 35%, 40%, 45%, 50%, 55%, 60%, 65%, 70%, 75%, 80%, 85%, 90%, 95%, 97%, 98%, or 99% amino acid sequence identity. Additionally, a related protein or a variant protein as used herein, refers to a protein that differs from another related protein or a parent protein in the number of prominent regions. For example, in some embodiments, variant proteins have 1, 2, 3, 4, 5, or 10 corresponding prominent regions that differ from the parent protein.

Several methods are known in the art that are suitable for generating variants of the enzymes of the present invention, including but not limited to site-saturation mutagenesis, scanning mutagenesis, insertional mutagenesis, random mutagenesis, site-directed mutagenesis, and directed-evolution, as well as various other recombinatorial approaches.

Characterization of wild-type and mutant proteins is accomplished via any means or "test" suitable and is preferably based on the assessment of properties of interest. For example, pH and/or temperature, as well as detergent and/or oxidative stability is/are determined in some embodiments of the present invention. Indeed, it is contemplated that enzymes having various degrees of stability in one or more of these characteristics (pH, temperature, proteolytic stability, detergent stability, and/or oxidative stability) will find use.

The terms "polynucleotide" and "nucleic acid", used interchangeably herein, refer to a polymeric form of nucleotides of any length, either ribonucleotides or deoxyribonucleotides. These terms include, but are not limited to, a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The following are non-limiting examples of polynucleotides: genes, gene fragments, chromosomal fragments, ESTs, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. In some embodiments, polynucleotides comprise modified nucleotides, such as methylated nucleotides and nucleotide analogs, uracil, other sugars and linking groups such as fluororibose and thioate, and nucleotide branches. In alternative embodiments, the sequence of nucleotides is interrupted by non-nucleotide components.

As used herein, the terms "DNA construct" and "transforming DNA" are used interchangeably to refer to DNA used to introduce sequences into a host cell or organism. The DNA may be generated in vitro by PCR or any other suitable technique(s) known to those in the art. In particularly preferred embodiments, the DNA construct comprises a sequence of interest (e.g., as an incoming sequence). In some embodiments, the sequence is operably linked to additional elements such as control elements (e.g., promoters, etc.). The DNA construct may further comprise a selectable marker. It may further comprise an incoming sequence flanked by homology boxes. In a further embodiment, the transforming DNA comprises other non-homologous sequences, added to the ends (e.g., stuffer sequences or flanks). In some embodiments, the ends of the incoming sequence are closed such that the transforming DNA forms a closed circle. The transforming sequences may be wild-type, mutant or modified. In some embodiments, the DNA construct comprises sequences homologous to the host cell chromosome. In other embodiments, the DNA construct comprises non-homologous sequences. Once the DNA construct is assembled in vitro it may be used to: 1) insert heterologous sequences into a desired target sequence of a host cell, and/or 2) mutagenize a region of the host cell chromosome (i.e., replace an endogenous sequence with a heterologous sequence), 3) delete target genes; and/or introduce a replicating plasmid into the host.

As used herein, the terms "expression cassette" and "expression vector" refer to nucleic acid constructs generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In preferred embodiments, expression vectors have the ability to incorporate and express heterologous DNA fragments in a host cell. Many prokaryotic and eukaryotic expression vectors are commercially available. Selection of appropriate expression vectors is within the knowledge of those of skill in the art. The term "expression cassette" is used interchangeably herein with "DNA construct," and their grammatical equivalents. Selection of appropriate expression vectors is within the knowledge of those of skill in the art.

As used herein, the term "vector" refers to a polynucleotide construct designed to introduce nucleic acids into one or more cell types. Vectors include cloning vectors, expression vectors, shuttle vectors, plasmids, cassettes and the like. In some embodiments, the polynucleotide construct comprises a DNA sequence encoding the protease (e.g., precursor or mature protease) that is operably linked to a suitable prosequence (e.g., secretory, etc.) capable of effecting the expression of the DNA in a suitable host.

As used herein, the term "plasmid" refers to a circular double-stranded (ds) DNA construct used as a cloning vector, and which forms an extrachromosomal self-replicating genetic element in some eukaryotes or prokaryotes, or integrates into the host chromosome.

As used herein in the context of introducing a nucleic acid sequence into a cell, the term "introduced" refers to any method suitable for transferring the nucleic acid sequence into the cell. Such methods for introduction include but are not limited to protoplast fusion, transfection, transformation, conjugation, and transduction (See e.g., Ferrari et al., "Genetics," in Hardwood et al, (eds.), *Bacillus*, Plenum Publishing Corp., pages 57-72, 1989).

As used herein, the terms "transformed" and "stably transformed" refers to a cell that has a non-native (heterologous) polynucleotide sequence integrated into its genome or as an episomal plasmid that is maintained for at least two generations.

As used herein, the term "selectable marker-encoding nucleotide sequence" refers to a nucleotide sequence, which is capable of expression in the host cells and where expression of the selectable marker confers to cells containing the expressed gene the ability to grow in the presence of a corresponding selective agent or lack of an essential nutrient.

As used herein, the terms "selectable marker" and "selective marker" refer to a nucleic acid (e.g., a gene) capable of expression in host cell, which allows for ease of selection of those hosts containing the vector. Examples of such selectable markers include but are not limited to antimicrobials. Thus, the term "selectable marker" refers to genes that provide an indication that a host cell has taken up an incoming DNA of interest or some other reaction has occurred. Typically, selectable markers are genes that confer antimicrobial resistance or a metabolic advantage on the host cell to allow cells containing the exogenous DNA to be distinguished from cells that have not received any exogenous sequence during the transformation. A "residing selectable marker" is one that is located on the chromosome of the microorganism to be transformed. A residing selectable marker encodes a gene that is different from the selectable marker on the transforming DNA construct. Selective markers are well known to those of skill in the art. As indicated above, preferably the marker is an antimicrobial resistant marker (e.g., $amp^R$; $phleo^R$; $spec^R$; $kan^R$; $ery^R$; $tet^R$; $cmp^R$; and $neo^R$ (See e.g., Guerot-Fleury, Gene, 167: 335-337, 1995; Palmeros et al., Gene 247:255-264, 2000; and Trieu-Cuot et al., Gene, 23:331-341, 1983). Other markers useful in accordance with the invention include, but are not limited to auxotrophic markers, such as tryptophan; and detection markers, such as β-galactosidase.

As used herein, the term "promoter" refers to a nucleic acid sequence that functions to direct transcription of a downstream gene. In preferred embodiments, the promoter is appropriate to the host cell in which the target gene is being expressed. The promoter, together with other transcriptional and translational regulatory nucleic acid sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

A nucleic acid is "operably linked" when it is placed into a functional relationship with another nucleic acid sequence. For example, DNA encoding a secretory leader (i.e., a signal peptide), is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein the term "gene" refers to a polynucleotide (e.g., a DNA segment) that encodes a polypeptide and includes regions preceding and following the coding regions as well as intervening sequences (introns) between individual coding segments (exons).

As used herein, "homologous genes" refers to a pair of genes from different, but usually related species, which correspond to each other and which are identical or very similar to each other. The term encompasses genes that are separated by speciation (i.e., the development of new species) (e.g., orthologous genes), as well as genes that have been separated by genetic duplication (e.g., paralogous genes).

As used herein, "ortholog" and "orthologous genes" refer to genes in different species that have evolved from a common ancestral gene (i.e., a homologous gene) by speciation. Typically, orthologs retain the same function during the course of evolution. Identification of orthologs finds use in the reliable prediction of gene function in newly sequenced genomes.

As used herein, "paralog" and "paralogous genes" refer to genes that are related by duplication within a genome. While orthologs retain the same function through the course of evolution, paralogs evolve new functions, even though some functions are often related to the original one. Examples of paralogous genes include, but are not limited to genes encoding trypsin, chymotrypsin, elastase, and thrombin, which are all serine proteinases and occur together within the same species.

As used herein, "homology" refers to sequence similarity or identity, with identity being preferred. This homology is determined using standard techniques known in the art (See e.g., Smith and Waterman, Adv Appl Math, 2:482, 1981; Needleman and Wunsch, J Mol Biol, 48:443, 1970; Pearson and Lipman, Proc Natl Acad Sci USA, 85:2444, 1988; programs such as GAP, BESTFIT, FASTA, and TFASTA in the Wisconsin Genetics Software Package, Genetics Computer Group, Madison, Wis.; and Devereux et al., Nucl Acid Res, 12:387-395, 1984).

As used herein, an "analogous sequence" is one wherein the function of the gene is essentially the same as the gene based on the *Geobacillus caldoproteolyticus* thermolysin. Additionally, analogous genes include at least 45%, 50%, 55%, 60%, 65%, 70%, 75%, 80%, 85%, 90%, 95%, 97%, 98%, 99% or 100% sequence identity with the sequence of the *Geobacillus caldoproteolyticus* thermolysin. In additional embodiments more than one of the above properties applies to the sequence. Analogous sequences are determined by known methods of sequence alignment. A commonly used alignment method is BLAST, although as indicated above and below, there are other methods that also find use in aligning sequences.

One example of a useful algorithm is PILEUP. PILEUP creates a multiple sequence alignment from a group of related sequences using progressive, pair-wise alignments. It can also plot a tree showing the clustering relationships used to create the alignment. PILEUP uses a simplification of the progressive alignment method of Feng and Doolittle (Feng and Doolittle, J Mol Evol, 35:351-360, 1987). The method is similar to that described by Higgins and Sharp (Higgins and Sharp, CABIOS 5:151-153, 1989). Useful PILEUP parameters including a default gap weight of 3.00, a default gap length weight of 0.10, and weighted end gaps.

Another example of a useful algorithm is the BLAST algorithm, described by Altschul et al., (Altschul et al., J Mol Biol, 215:403-410, 1990; and Karlin et al., Proc Natl Acad Sci USA, 90:5873-5787, 1993). A particularly useful BLAST program is the WU-BLAST-2 program (See, Altschul et al., Meth Enzymol, 266:460-480, 1996). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched. However, the values may be adjusted to increase sensitivity. A % amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

Thus, "percent (%) nucleic acid sequence identity" is defined as the percentage of nucleotide residues in a candidate sequence that are identical to the nucleotide residues of the starting sequence (i.e., the sequence of interest). A preferred method utilizes the BLASTN module of WU-BLAST-2 set to the default parameters, with overlap span and overlap fraction set to 1 and 0.125, respectively.

As used herein, the term "hybridization" refers to the process by which a strand of nucleic acid joins with a complementary strand through base pairing, as known in the art.

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° C. below the Tm; "intermediate stringency" at about 10-20° C. below the Tm of the probe; and "low stringency" at about 20-25° C. below the Tm. Functionally, maximum stringency conditions may be used to identify sequences having strict identity or near-strict identity with the hybridization probe; while intermediate or low stringency hybridization can be used to identify or detect polynucleotide sequence homologs.

Moderate and high stringency hybridization conditions are well known in the art. An example of high stringency conditions includes hybridization at about 42° C. in 50% formamide, 5×SSC, 5×Denhardt's solution, 0.5% SDS and 100 µg/ml denatured carrier DNA followed by washing two times in 2×SSC and 0.5% SDS at room temperature and two additional times in 0.1×SSC and 0.5% SDS at 42° C. An example of moderate stringent conditions include an overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/ml denatured sheared salmon sperm DNA, followed by washing the filters in 1×SSC at about 37-50° C. Those of skill in the art know how to adjust the temperature, ionic strength, etc. as necessary to accommodate factors such as probe length and the like.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. "Recombination," "recombining," and generating a "recombined" nucleic acid are generally the assembly of two or more nucleic acid fragments wherein the assembly gives rise to a chimeric gene.

In a preferred embodiment, mutant DNA sequences are generated with site saturation mutagenesis in at least one codon. In another preferred embodiment, site saturation mutagenesis is performed for two or more codons. In a further embodiment, mutant DNA sequences have more than 50%, more than 55%, more than 60%, more than 65%, more than 70%, more than 75%, more than 80%, more than 85%, more than 90%, more than 95%, or more than 98% homology with the wild-type sequence. In alternative embodiments, mutant DNA is generated in vivo using any known mutagenic procedure such as, for example, radiation, nitrosoguanidine and the like. The desired DNA sequence is then isolated and used in the methods provided herein.

As used herein, the term "target sequence" refers to a DNA sequence in the host cell that encodes the sequence where it is desired for the incoming sequence to be inserted into the host cell genome. In some embodiments, the target sequence encodes a functional wild-type gene or operon, while in other embodiments the target sequence encodes a functional mutant gene or operon, or a non-functional gene or operon.

As used herein, a "flanking sequence" refers to any sequence that is either upstream or downstream of the sequence being discussed (e.g., for genes A-B-C, gene B is flanked by the A and C gene sequences). In a preferred embodiment, the incoming sequence is flanked by a homology box on each side. In another embodiment, the incoming sequence and the homology boxes comprise a unit that is flanked by stuffer sequence on each side. In some embodiments, a flanking sequence is present on only a single side (either 3' or 5'), but in preferred embodiments, it is on each side of the sequence being flanked. In some embodiments, a flanking sequence is present on only a single side (either 3' or 5'), while in preferred embodiments it is present on each side of the sequence being flanked.

As used herein, the term "stuffer sequence" refers to any extra DNA that flanks homology boxes (typically vector sequences). However, the term encompasses any non-homologous DNA sequence. Not to be limited by any theory, a stuffer sequence provides a noncritical target for a cell to initiate DNA uptake.

As used herein, the terms "amplification" and "gene amplification" refer to a process by which specific DNA sequences are disproportionately replicated such that the amplified gene becomes present in a higher copy number than was initially present in the genome. In some embodiments, selection of cells by growth in the presence of a drug (e.g., an inhibitor of an inhibitable enzyme) results in the amplification of either the endogenous gene encoding the gene product required for growth in the presence of the drug or by amplification of exogenous (i.e., input) sequences encoding this gene product, or both.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "co-amplification" refers to the introduction into a single cell of an amplifiable marker in conjunction with other gene sequences (i.e., comprising one or more non-selectable genes such as those contained within an expression vector) and the application of appropriate selective pressure such that the cell amplifies both the amplifiable marker and the other, non-selectable gene sequences. The amplifiable marker may be physically linked to the other gene sequences or alternatively two separate pieces of DNA, one containing the amplifiable marker and the other containing the non-selectable marker, may be introduced into the same cell.

As used herein, the terms "amplifiable marker," "amplifiable gene," and "amplification vector" refer to a gene or a vector encoding a gene, which permits the amplification of that gene under appropriate growth conditions.

"Template specificity" is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (See e.g., Kacian et al., Proc Natl Acad Sci USA 69:3038, 1972) and other nucleic acids are not replicated by this amplification enzyme. Similarly, in the case of T7 RNA polymerase, this amplification enzyme has a stringent specificity for its own promoters (See, Chamberlin et al., Nature 228:227, 1970). In the case of T4 DNA ligase, the enzyme will not ligate the two oligonucleotides or polynucleotides, where there is a mismatch between the oligonucleotide or polynucleotide substrate and the template at the ligation junction (See, Wu and Wallace, Genomics 4:560, 1989). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences.

As used herein, the term "amplifiable nucleic acid" refers to nucleic acids, which may be amplified by any amplification method. It is contemplated that "amplifiable nucleic acid" will usually comprise "sample template."

As used herein, the term "sample template" refers to nucleic acid originating from a sample, which is analyzed for the presence of "target" (defined below). In contrast, "background template" is used in reference to nucleic acid other than sample template, which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the methods of U.S. Pat. Nos. 4,683,195 4,683,202, and 4,965,188, hereby incorporated by reference, which include methods for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "RT-PCR" refers to the replication and amplification of RNA sequences. In this method, reverse transcription is coupled to PCR, most often using a one enzyme procedure in which a thermostable polymerase is employed, as described in U.S. Pat. No. 5,322,770, herein incorporated by reference. In RT-PCR, the RNA template is converted to cDNA due to the reverse transcriptase activity of the polymerase, and then amplified using the polymerizing activity of the polymerase (i.e., as in other PCR methods).

As used herein, the terms "restriction endonucleases" and "restriction enzymes" refer to bacterial enzymes, each of which cut double-stranded DNA at or near a specific nucleotide sequence.

A "restriction site" refers to a nucleotide sequence recognized and cleaved by a given restriction endonuclease and is frequently the site for insertion of DNA fragments. In certain embodiments of the invention restriction sites are engineered into the selective marker and into 5' and 3' ends of the DNA construct.

As used herein, the term "chromosomal integration" refers to the process whereby an incoming sequence is introduced into the chromosome of a host cell. The homologous regions of the transforming DNA align with homologous regions of the chromosome. Subsequently, the sequence between the homology boxes is replaced by the incoming sequence in a double crossover (i.e., homologous recombination). In some embodiments of the present invention, homologous sections of an inactivating chromosomal segment of a DNA construct align with the flanking homologous regions of the indigenous chromosomal region of the *Bacillus* chromosome. Subsequently, the indigenous chromosomal region is deleted by the DNA construct in a double crossover (i.e., homologous recombination).

"Homologous recombination" means the exchange of DNA fragments between two DNA molecules or paired chromosomes at the site of identical or nearly identical nucleotide sequences. In a preferred embodiment, chromosomal integration is homologous recombination.

"Homologous sequences" as used herein means a nucleic acid or polypeptide sequence having 100%, 99%, 98%, 97%, 96%, 95%, 94%, 93%, 92%, 91%, 90%, 88%, 85%, 80%, 75%, or 70% sequence identity to another nucleic acid or polypeptide sequence when optimally aligned for comparison. In some embodiments, homologous sequences have between 85% and 100% sequence identity, while in other embodiments there is between 90% and 100% sequence identity, and in more preferred embodiments, there is 95% and 100% sequence identity.

As used herein "amino acid" refers to peptide or protein sequences or portions thereof. The terms "protein," "peptide," and "polypeptide" are used interchangeably.

As used herein, the term "heterologous protein" refers to a protein or polypeptide that does not naturally occur in the host cell. Examples of heterologous proteins include enzymes such as hydrolases including proteases. In some embodiments, the gene encoding the proteins are naturally occurring genes, while in other embodiments, mutated and/or synthetic genes are used.

As used herein, "homologous protein" refers to a protein or polypeptide native or naturally occurring in a cell. In preferred embodiments, the cell is a Gram-positive cell, while in particularly preferred embodiments the cell is a *Bacillus* host cell. In alternative embodiments, the homologous protein is a native protein produced by other organisms, including but not limited to *E. coli, Streptomyces, Trichoderma*, and *Aspergillus*. The invention encompasses host cells producing the homologous protein via recombinant DNA technology.

As used herein, an "operon region" comprises a group of contiguous genes that are transcribed as a single transcription unit from a common promoter, and are thereby subject to co-regulation. In some embodiments, the operon includes a regulator gene. In most preferred embodiments, operons that are highly expressed as measured by RNA levels, but have an unknown or unnecessary function are used.

As used herein, an "antimicrobial region" is a region containing at least one gene that encodes an antimicrobial protein.

A polynucleotide is said to "encode" an RNA or a polypeptide if, in its native state or when manipulated by methods known to those of skill in the art, it can be transcribed and/or translated to produce the RNA, the polypeptide or a fragment thereof. The anti-sense strand of such a nucleic acid is also said to encode the sequences.

As is known in the art, a DNA can be transcribed by an RNA polymerase to produce RNA, but an RNA can be reverse transcribed by reverse transcriptase to produce a DNA. Thus a DNA can encode a RNA and vice versa.

The term "regulatory segment" or "regulatory sequence" or "expression control sequence" refers to a polynucleotide sequence of DNA that is operatively linked with a polynucleotide sequence of DNA that encodes the amino acid sequence of a polypeptide chain to effect the expression of the encoded amino acid sequence. The regulatory sequence can inhibit, repress, or promote the expression of the operably linked polynucleotide sequence encoding the amino acid.

"Host strain" or "host cell" refers to a suitable host for an expression vector comprising DNA according to the present invention.

An enzyme is "overexpressed" in a host cell if the enzyme is expressed in the cell at a higher level that the level at which it is expressed in a corresponding wild-type cell.

The terms "protein" and "polypeptide" are used interchangeability herein. The 3-letter code for amino acids as defined in conformity with the IUPAC-IUB Joint Commission on Biochemical Nomenclature (JCBN) is used through out this disclosure. It is also understood that a polypeptide may be coded for by more than one nucleotide sequence due to the degeneracy of the genetic code.

A "prosequence" is an amino acid sequence between the signal sequence and mature protease that is necessary for the secretion of the protease. Cleavage of the pro sequence will result in a mature active protease.

The term "signal sequence" or "signal peptide" refers to any sequence of nucleotides and/or amino acids that participate in the secretion of the mature or precursor forms of the protein. This definition of signal sequence is a functional one, meant to include all those amino acid sequences encoded by the N-terminal portion of the protein gene, which participate in the effectuation of the secretion of protein. They are often, but not universally, bound to the N-terminal portion of a protein or to the N-terminal portion of a precursor protein. The signal sequence may be endogenous or exogenous. The signal sequence may be that normally associated with the protein (e.g., protease), or may be from a gene encoding another secreted protein. One exemplary exogenous signal sequence comprises the first seven amino acid residues of the signal sequence from *Bacillus subtilis* subtilisin fused to the remainder of the signal sequence of the subtilisin from *Bacillus lentus* (ATCC 21536).

The term "hybrid signal sequence" refers to signal sequences in which part of sequence is obtained from the expression host fused to the signal sequence of the gene to be expressed. In some embodiments, synthetic sequences are utilized.

The term "mature" form of a protein or peptide refers to the final functional form of the protein or peptide. To exemplify, a mature form of thermolysin includes the amino acid sequence of SEQ ID NO:3.

The term "precursor" form of a protein or peptide refers to a mature form of the protein having a prosequence operably linked to the amino or carbonyl terminus of the protein. The precursor may also have a "signal" sequence operably linked, to the amino terminus of the prosequence. The precursor may also have additional polynucleotides that are involved in post-translational activity (e.g., polynucleotides cleaved therefrom to leave the mature form of a protein or peptide).

"Naturally occurring enzyme" refers to an enzyme having the unmodified amino acid sequence identical to that found in nature. Naturally occurring enzymes include native enzymes, those enzymes naturally expressed or found in the particular microorganism.

The terms "derived from" and "obtained from" refer to not only a protease produced or producible by a strain of the organism in question, but also a protease encoded by a DNA sequence isolated from such strain and produced in a host organism containing such DNA sequence. Additionally, the term refers to a protease that is encoded by a DNA sequence of synthetic and/or cDNA origin and which has the identifying characteristics of the protease in question. To exemplify, "proteases derived from *Bacillus* sp." refers to those enzymes having proteolytic activity which are naturally-produced by *Bacillus* sp., as well as to neutral metalloproteases like those produced by *Bacillus* sp. sources but which through the use of genetic engineering techniques are produced by non-*Geobacillus caldoproteolyticus* organisms transformed with a nucleic acid encoding said neutral metalloproteases.

A "derivative" within the scope of this definition generally retains the characteristic proteolytic activity observed in the wild-type, native or parent form to the extent that the derivative is useful for similar purposes as the wild-type, native or parent form. Functional derivatives of neutral metalloprotease encompass naturally occurring, synthetically or recombinantly produced peptides or peptide fragments having the general characteristics of the neutral metalloprotease of the present invention.

The term "functional derivative" refers to a derivative of a nucleic acid having the functional characteristics of a nucleic acid encoding a neutral metalloprotease. Functional derivatives of a nucleic acid, which encode neutral metalloprotease of the present invention encompass naturally occurring, synthetically or recombinantly produced nucleic acids or fragments and encode neutral metalloprotease characteristic of the present invention. Wild type nucleic acid encoding neutral metalloprotease according to the invention include naturally occurring alleles and homologues based on the degeneracy of the genetic code known in the art.

The term "identical" in the context of two nucleic acids or polypeptide sequences refers to the residues in the two sequences that are the same when aligned for maximum correspondence, as measured using one of the following sequence comparison or analysis algorithms.

The term "optimal alignment" refers to the alignment giving the highest percent identity score.

"Percent sequence identity," "percent amino acid sequence identity," "percent gene sequence identity," and/or "percent nucleic acid/polynucloetide sequence identity," with respect to two amino acid, polynucleotide and/or gene sequences (as appropriate), refer to the percentage of residues that are identical in the two sequences when the sequences are optimally aligned. Thus, 80% amino acid sequence identity means that 80% of the amino acids in two optimally aligned polypeptide sequences are identical.

The phrase "substantially identical" in the context of two nucleic acids or polypeptides thus refers to a polynucleotide or polypeptide that comprising at least 70% sequence identity, preferably at least 75%, preferably at least 80%, preferably at least 85%, preferably at least 90%, preferably at least 95%, preferably at least 97%, preferably at least 98% and preferably at least 99% sequence identity as compared to a reference sequence using the programs or algorithms (e.g., BLAST, ALIGN, CLUSTAL) using standard parameters. One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another indication that two nucleic acid sequences are substantially identical is that the two molecules hybridize to each other under stringent conditions (e.g., within a range of medium to high stringency).

The term "isolated" or "purified" refers to a material that is removed from its original environment (e.g., the natural environment if it is naturally occurring). For example, the material is said to be "purified" when it is present in a particular composition in a higher or lower concentration than exists in a naturally occurring or wild type organism or in combination with components not normally present upon expression from a naturally occurring or wild type organism. For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector, and/or such polynucleotides or polypeptides could be part of a composition, and still be isolated in that such vector or composition is not part of its natural environment. In preferred embodiments, a nucleic acid or protein is said to be purified, for example, if it gives rise to essentially one band in an electrophoretic gel or blot.

The term "isolated", when used in reference to a DNA sequence, refers to a DNA sequence that has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (See e.g., Dynan and Tijan, Nature 316:774-78, 1985). The term "an isolated DNA sequence" is alternatively referred to as "a cloned DNA sequence".

The term "isolated," when used in reference to a protein, refers to a protein that is found in a condition other than its native environment. In a preferred form, the isolated protein is substantially free of other proteins, particularly other homologous proteins. An isolated protein is more than 10% pure, preferably more than 20% pure, and even more preferably more than 30% pure, as determined by SDS-PAGE. Further aspects of the invention encompass the protein in a highly purified form (i.e., more than 40% pure, more than 60% pure, more than 80% pure, more than 90% pure, more than 95% pure, more than 97% pure, and even more than 99% pure), as determined by SDS-PAGE.

The following cassette mutagenesis method may be used to facilitate the construction of the enzyme variants of the present invention, although other methods may be used. First, as described herein, a naturally-occurring gene encoding the enzyme is obtained and sequenced in whole or in part. Then, the sequence is scanned for a point at which it is desired to make a mutation (deletion, insertion or substitution) of one or more amino acids in the encoded enzyme. The sequences flanking this point are evaluated for the presence of restriction sites for replacing a short segment of the gene with an oligonucleotide pool which when expressed will encode various mutants. Such restriction sites are preferably unique sites within the protein gene so as to facilitate the replacement of the gene segment. However, any convenient restriction site that is not overly redundant in the enzyme gene may be used, provided the gene fragments generated by restriction digestion can be reassembled in proper sequence. If restriction sites are not present at locations within a convenient distance from the selected point (from 10 to 15 nucleotides), such sites are generated by substituting nucleotides in the gene in such a fashion that neither the reading frame nor the amino acids encoded are changed in the final construction. Mutation of the gene in order to change its sequence to conform to the desired sequence is accomplished by M13 primer extension in accord with generally known methods. The task of locating suitable flanking regions and evaluating the needed changes to arrive at two convenient restriction site sequences is made routine by the redundancy of the genetic code, a restriction enzyme map of the gene and the large number of different restriction enzymes. Note that if a convenient flanking restriction site is available, the above method need be used only in connection with the flanking region that does not contain a site.

Once the naturally-occurring DNA and/or synthetic DNA is cloned, the restriction sites flanking the positions to be mutated are digested with the cognate restriction enzymes and a plurality of end termini-complementary oligonucleotide cassettes are ligated into the gene. The mutagenesis is simplified by this method because all of the oligonucleotides can be synthesized so as to have the same restriction sites, and no synthetic linkers are necessary to create the restriction sites.

As used herein, "corresponding to," refers to a residue at the enumerated position in a protein or peptide, or a residue that is analogous, homologous, or equivalent to an enumerated residue in a protein or peptide.

As used herein, "corresponding region," generally refers to an analogous position along related proteins or a parent protein.

As used herein, the term, "combinatorial mutagenesis" refers to methods in which libraries of variants of a starting sequence are generated. In these libraries, the variants contain one or several mutations chosen from a predefined set of mutations. In addition, the methods provide means to introduce random mutations, which were not members of the predefined set of mutations. In some embodiments, the methods include those set forth in U.S. application Ser. No. 09/699,250, filed Oct. 26, 2000, hereby incorporated by reference. In alternative embodiments, combinatorial mutagenesis methods encompass commercially available kits (e.g., QUIKCHANGE® Multisite, Stratagene, San Diego, Calif.).

As used herein, the term "library of mutants" refers to a population of cells which are identical in most of their genome but include different homologues of one or more genes. Such libraries can be used, for example, to identify genes or operons with improved traits.

As used herein, the terms "starting gene" and "parent gene" refer to a gene of interest that encodes a protein of interest that is to be improved and/or changed using the present invention.

As used herein, the terms "multiple sequence alignment" and "MSA" refer to the sequences of multiple homologs of a starting gene that are aligned using an algorithm (e.g., Clustal W).

As used herein, the terms "consensus sequence" and "canonical sequence" refer to an archetypical amino acid sequence against which all variants of a particular protein or sequence of interest are compared. The terms also refer to a sequence that sets forth the nucleotides that are most often present in a DNA sequence of interest. For each position of a gene, the consensus sequence gives the amino acid that is most abundant in that position in the MSA.

As used herein, the term "consensus mutation" refers to a difference in the sequence of a starting gene and a consensus sequence. Consensus mutations are identified by comparing the sequences of the starting gene and the consensus sequence obtained from a MSA. In some embodiments, consensus mutations are introduced into the starting gene such that it becomes more similar to the consensus sequence. Consensus mutations also include amino acid changes that change an amino acid in a starting gene to an amino acid that is more frequently found in an MSA at that position relative to the frequency of that amino acid in the starting gene. Thus, the term consensus mutation comprises all single amino acid changes that replace an amino acid of the starting gene with an amino acid that is more abundant than the amino acid in the MSA.

The terms "modified sequence" and "modified genes" are used interchangeably herein to refer to a sequence that includes a deletion, insertion or interruption of naturally occurring nucleic acid sequence. In some preferred embodiments, the expression product of the modified sequence is a truncated protein (e.g., if the modification is a deletion or interruption of the sequence). In some particularly preferred embodiments, the truncated protein retains biological activity. In alternative embodiments, the expression product of the modified sequence is an elongated protein (e.g., modifications comprising an insertion into the nucleic acid sequence). In some embodiments, an insertion leads to a truncated protein (e.g., when the insertion results in the formation of a stop codon). Thus, an insertion may result in either a truncated protein or an elongated protein as an expression product.

As used herein, the terms "mutant sequence" and "mutant gene" are used interchangeably and refer to a sequence that has an alteration in at least one codon occurring in a host cell's wild-type sequence. The expression product of the mutant sequence is a protein with an altered amino acid sequence relative to the wild-type. The expression product may have an altered functional capacity (e.g., enhanced enzymatic activity).

The terms "mutagenic primer" or "mutagenic oligonucleotide" (used interchangeably herein) are intended to refer to oligonucleotide compositions which correspond to a portion of the template sequence and which are capable of hybridizing thereto. With respect to mutagenic primers, the primer will not precisely match the template nucleic acid, the mismatch or mismatches in the primer being used to introduce the desired mutation into the nucleic acid library. As used herein, "non-mutagenic primer" or "non-mutagenic oligonucleotide" refers to oligonucleotide compositions that match precisely to the template nucleic acid. In one embodiment of the invention, only mutagenic primers are used. In another preferred embodiment of the invention, the primers are designed so that for at least one region at which a mutagenic primer has been included, there is also non-mutagenic primer included in the oligonucleotide mixture. By adding a mixture of mutagenic primers and non-mutagenic primers corresponding to at least one of the mutagenic primers, it is possible to produce a resulting nucleic acid library in which a variety of combinatorial mutational patterns are presented. For example, if it is desired that some of the members of the mutant nucleic acid library retain their parent sequence at certain positions while other members are mutant at such sites, the non-mutagenic primers provide the ability to obtain a specific level of non-mutant members within the nucleic acid library for a given residue. The methods of the invention employ mutagenic and non-mutagenic oligonucleotides which are generally between 10-50 bases in length, more preferably about 15-45 bases in length. However, it may be necessary to use primers that are either shorter than 10 bases or longer than 50 bases to obtain the mutagenesis result desired. With respect to corresponding mutagenic and non-mutagenic primers, it is not necessary that the corresponding oligonucleotides be of identical length, but only that there is overlap in the region corresponding to the mutation to be added.

Primers may be added in a pre-defined ratio according to the present invention. For example, if it is desired that the resulting library have a significant level of a certain specific mutation and a lesser amount of a different mutation at the same or different site, by adjusting the amount of primer added, it is possible to produce the desired biased library. Alternatively, by adding lesser or greater amounts of non-mutagenic primers, it is possible to adjust the frequency with which the corresponding mutation(s) are produced in the mutant nucleic acid library.

The terms "wild-type sequence," or "wild-type gene" are used interchangeably herein, to refer to a sequence that is native or naturally occurring in a host cell. In some embodiments, the wild-type sequence refers to a sequence of interest that is the starting point of a protein-engineering project. The wild-type sequence may encode either a homologous or heterologous protein. A homologous protein is one the host cell would produce without intervention. A heterologous protein is one that the host cell would not produce but for the intervention.

As used herein, the term "equivalent" when used in reference to the position of an amino acid residue in a thermolysin protein refers to the position of an amino acid residue in a thermolysin variant that corresponds in position in the primary sequence of the unmodified precursor e.g. wild-type thermolysin. In order to establish the position of equivalent amino acid positions in a thermolysin, the amino acid sequence of the thermolysin that is modified to generate the thermolysin variant is directly compared to the thermolysin of SEQ ID NO:3. After aligning the residues, allowing for insertions and deletions in order to maintain alignment (i.e. avoiding the elimination of conserved residues through arbitrary deletion or insertion), the residues at positions equivalent to particular amino acid positions in the sequence of the thermolysin of SEQ ID NO:3 are defined.

The term "oxidation stable" refers to proteases of the present invention that retain a specified amount of enzymatic activity over a given period of time under conditions prevailing during the proteolytic, hydrolyzing, cleaning or other process of the invention, for example while exposed to or contacted with bleaching agents or oxidizing agents. In some embodiments, the proteases retain at least 50%, 60%, 70%, 75%, 80%, 85%, 90%, 92%, 95%, 96%, 97%, 98% or 99% proteolytic activity after contact with a bleaching or oxidizing agent over a given time period, for example, at least 1 minute, 3 minutes, 5 minutes, 8 minutes, 12 minutes, 16 minutes, 20 minutes, etc.

The term "chelator stable" refers to proteases of the present invention that retain a specified amount of enzymatic activity over a given period of time under conditions prevailing during the proteolytic, hydrolyzing, cleaning or other process of the invention, for example while exposed to or contacted with chelating agents. In some embodiments, the proteases retain at least 50%, 60%, 70%, 75%, 80%, 85%, 90%, 92%, 95%, 96%, 97%, 98% or 99% proteolytic activity after contact with a chelating agent over a given time period, for example, at least 10 minutes, 20 minutes, 40 minutes, 60 minutes, 100 minutes, etc.

The terms "thermally stable" and "thermostable" refer to proteases of the present invention that retain a specified amount of enzymatic activity after exposure to identified temperatures over a given period of time under conditions prevailing during the proteolytic, hydrolyzing, cleaning or other process of the invention, for example while exposed to altered temperatures. Altered temperatures include increased or decreased temperatures. In some embodiments, the proteases retain at least 50%, 60%, 70%, 75%, 80%, 85%, 90%, 92%, 95%, 96%, 97%, 98% or 99% proteolytic activity after exposure to altered temperatures over a given time period, for example, at least 60 minutes, 120 minutes, 180 minutes, 240 minutes, 300 minutes, etc.

As used herein, the term "chemical stability" refers to the stability of a protein (e.g., an enzyme) towards chemicals that adversely affect its activity. In some embodiments, such chemicals include, but are not limited to hydrogen peroxide, peracids, anionic detergents, cationic detergents, non-ionic detergents, chelants, etc. However, it is not intended that the present invention be limited to any particular chemical stability level nor range of chemical stability. In particular, the terms "detergent stable" and "LAS stable" refer to proteases of the present invention that retain a specified amount of enzymatic activity after exposure to a detergent composition over a given period of time under conditions prevailing during the proteolytic, hydrolyzing, cleaning or other process of the invention. In some embodiments, the proteases retain at least 50%, 60%, 70%, 75%, 80%, 85%, 90%, 92%, 95%, 96%, 97%, 98% or 99% proteolytic activity after exposure to detergent over a given time period, for example, at least 60 minutes, 120 minutes, 180 minutes, 240 minutes, 300 minutes, etc.

The term "enhanced stability" in the context of an oxidation, chelator, thermal and/or pH stable protease refers to a higher retained proteolytic activity over time as compared to other neutral metalloproteases and/or wild-type enzymes.

The term "diminished stability" in the context of an oxidation, chelator, thermal and/or pH stable protease refers to a lower retained proteolytic activity over time as compared to other neutral metalloproteases and/or wild-type enzymes.

As used herein, the term "cleaning composition" includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, car or carpet shampoos, bathroom cleaners; hair shampoos and hair-rinses; shower gels and foam baths and metal cleaners; as well as cleaning auxiliaries such as bleach additives and "stain-stick" or pre-treat types.

Unless otherwise noted, all component or composition levels are in reference to the active level of that component or composition, and are exclusive of impurities, for example, residual solvents or by-products, which may be present in commercially available sources.

Enzyme components weights are based on total active protein. All percentages and ratios are calculated by weight unless otherwise indicated. All percentages and ratios are calculated based on the total composition unless otherwise indicated.

The term "cleaning activity" refers to the cleaning performance achieved by the protease under conditions prevailing during the proteolytic, hydrolyzing, cleaning or other process of the invention. In some embodiments, cleaning performance is determined by the application of various cleaning assays concerning enzyme sensitive stains, for example grass, blood, milk, or egg protein as determined by various chromatographic, spectrophotometric or other quantitative methodologies after subjection of the stains to standard wash conditions. Exemplary assays include, but are not limited to those described in WO 99/34011, and U.S. Pat. No. 6,605,458 (both of which are herein incorporated by reference), as well as those methods included in the Examples.

The term "cleaning effective amount" of a protease refers to the quantity of protease described hereinbefore that achieves a desired level of enzymatic activity in a specific cleaning composition. Such effective amounts are readily ascertained by one of ordinary skill in the art and are based on many factors, such as the particular protease used, the cleaning application, the specific composition of the cleaning composition, and whether a liquid or dry (e.g., granular, bar) composition is required, etc.

The term "cleaning adjunct materials" as used herein, means any liquid, solid or gaseous material selected for the particular type of cleaning composition desired and the form of the product (e.g., liquid, granule, powder, bar, paste, spray, tablet, gel; or foam composition), which materials are also preferably compatible with the protease enzyme used in the composition. In some embodiments, granular compositions are in "compact" form, while in other embodiments, the liquid compositions are in a "concentrated" form.

As used herein, a "low detergent concentration" system includes detergents where less than about 800 ppm of detergent components are present in the wash water. Japanese detergents are typically considered low detergent concentration systems, as they have usually have approximately 667 ppm of detergent components present in the wash water.

As used herein, a "medium detergent concentration" systems includes detergents wherein between about 800 ppm and about 2000 ppm of detergent components are present in the wash water. North American detergents are generally considered to be medium detergent concentration systems as they have usually approximately 975 ppm of detergent components present in the wash water. Brazilian detergents typically have approximately 1500 ppm of detergent components present in the wash water.

As used herein, "high detergent concentration" systems includes detergents wherein greater than about 2000 ppm of detergent components are present in the wash water. European detergents are generally considered to be high detergent concentration systems as they have approximately 3000-8000 ppm of detergent components in the wash water.

As used herein, "fabric cleaning compositions" include hand and machine laundry detergent compositions including laundry additive compositions and compositions suitable for use in the soaking and/or pretreatment of stained fabrics (e.g., clothes, linens, and other textile materials).

As used herein, "non-fabric cleaning compositions" include non-textile (i.e., fabric) surface cleaning compositions, including but not limited to dishwashing detergent compositions, oral cleaning compositions, denture cleaning compositions, and personal cleansing compositions.

The "compact" form of the cleaning compositions herein is best reflected by density and, in terms of composition, by the amount of inorganic filler salt. Inorganic filler salts are conventional ingredients of detergent compositions in powder form. In conventional detergent compositions, the filler salts are present in substantial amounts, typically 17-35% by weight of the total composition. In contrast, in compact compositions, the filler salt is present in amounts not exceeding 15% of the total composition. In some embodiments, the filler salt is present in amounts that do not exceed 10%, or more preferably, 5%, by weight of the composition. In some embodiments, the inorganic filler salts are selected from the alkali and alkaline-earth-metal salts of sulfates and chlorides. A preferred filler salt is sodium sulfate.

DETAILED DESCRIPTION OF THE INVENTION

Neutral metalloendopeptidases (i.e., neutral metalloproteases) (EC 3.4.24.4) belong to a protease class that has an absolute requirement for zinc ions for catalytic activity. These enzymes are optimally active at neutral pH and are in the 30 to 40 kDa size range. Neutral metalloproteases bind between two and four calcium ions that contribute to the structural stability of the protein. The bound metal ion at the active site of metalloproteases is an essential feature that allows the activation of a water molecule. The water molecule then functions as the nucleophile and cleaves the carbonyl group of the peptide bond.

The neutral zinc-binding metalloprotease family includes the bacterial enzyme thermolysin, and thermolysin-like proteases (TLPs), as well as carboxypeptidase A (a digestive enzyme), and the matrix metalloproteases that catalyze the reactions in tissue remodeling and degradation. The only well characterized of these proteases, with respect to stability and function is thermolysin, which hydrolyzes protein bonds on the amino-terminal side of hydrophobic amino acid residues. Thermolysin is a thermostable neutral zinc metalloproteinase first identified in the culture broth of *Bacillus* thermoproteolyticus Rokko. Subsequently, a similar neutral metalloprotease was identified in *Geobacillus caldoprotelyticus*, and this enzyme is also referred to herein as thermolysin. Natural and engineered proteases, such as thermolysin are often expressed in *Bacillus subtilis* (O'Donohue et al., Biochem J, 300:599-603, 1994), and several have been applied in detergent formulations to remove proteinaceous stains. Today, thermolysin is used in industry, especially for the enzymatic synthesis of N-carbobenzoxy 1-Asp-1-Phe methyl ester, a precursor of the artificial sweetener aspartame.

In general however, the serine proteases have been more widely utilized in detergents, at least partially due to the relative ease with which these proteases can be stabilized.

Indeed, metalloproteases are less frequently used in industry, and particularly in the detergent industry for a number of reasons. These enzymes involve more complex protein systems, as the enzymes have the absolute requirement for calcium and zinc ions for stability and function, respectively. Further, the detergent solution as well as the water used in the laundry process often contains components that interfere with the binding of the ions by the enzyme, or chelate these ions, resulting in a decrease or loss of proteolytic function and destabilization of the protease.

Detailed Description of Cleaning and Detergent Formulations of the Present Invention Unless otherwise noted, all component or composition levels provided herein are made in reference to the active level of that component or composition, and are exclusive of impurities, for example, residual solvents or by-products, which may be present in commercially available sources. Enzyme components weights are based on total active protein. All percentages and ratios are calculated by weight unless otherwise indicated. All percentages and ratios are calculated based on the total composition unless otherwise indicated.

In the exemplified detergent compositions, the enzymes levels are expressed by pure enzyme by weight of the total composition and unless otherwise specified, the detergent ingredients are expressed by weight of the total compositions.

Cleaning Compositions Comprising Neutral Metalloprotease

The neutral metalloproteases of the present invention are useful in formulating various detergent compositions. The cleaning composition of the present invention may be advantageously employed for example, in laundry applications, hard surface cleaning, automatic dishwashing applications, as well as cosmetic applications such as dentures, teeth, hair and skin. However, due to the unique advantages of increased effectiveness in lower temperature solutions and the superior color-safety profile, the enzymes of the present invention are ideally suited for laundry applications such as the bleaching of fabrics. Furthermore, the enzymes of the present invention find use in both granular and liquid compositions.

The enzymes of the present invention also find use in cleaning additive products. A cleaning additive product including at least one enzyme of the present invention is ideally suited for inclusion in a wash process when additional bleaching effectiveness is desired. Such instances include, but are not limited to low temperature solution cleaning applications. The additive product may be, in its simplest form, one or more neutral metalloprotease enzyme as provided by the present invention. In some embodiments, the additive is packaged in dosage form for addition to a cleaning process where a source of peroxygen is employed and increased bleaching effectiveness is desired. In some embodiments, the single dosage form comprises a pill, tablet, gelcap or other single dosage unit including pre-measured powders and/or liquids. In some embodiments, filler and/or carrier material(s) are included, in order to increase the volume of such composition. Suitable filler or carrier materials include, but are not limited to, various salts of sulfate, carbonate and silicate as well as talc, clay and the like. In some embodiments filler and/or carrier materials for liquid compositions include water and/or low molecular weight primary and secondary alcohols including polyols and diols. Examples of such alcohols include, but are not limited to, methanol, ethanol, propanol and isopropanol. In some embodiments, the compositions comprise from about 5% to about 90% of such materials. In additional embodiments, acidic fillers are used to reduce the pH of the composition. In some alternative embodiments the cleaning additive includes at least one activated peroxygen source as described below and/or adjunct ingredients as more fully described below.

The cleaning compositions and cleaning additives of the present invention require an effective amount of neutral metalloprotease enzyme as provided in the present invention. In some embodiments, the required level of enzyme is achieved by the addition of one or more species of neutral metalloprotease provided by the present invention. Typically, the cleaning compositions of the present invention comprise at least 0.0001 weight percent, from about 0.0001 to about 1, from about 0.001 to about 0.5, or even from about 0.01 to about 0.1 weight percent of at least one neutral metalloprotease provided by the present invention.

In some preferred embodiments, the cleaning compositions provided herein are typically formulated such that, during use in aqueous cleaning operations, the wash water has a pH of from about 5.0 to about 11.5, or in alternative embodiments, even from about 6.0 to about 10.5. In some preferred embodiments, liquid product formulations are typically formulated to have a neat pH from about 3.0 to about 9.0, while in some alternative embodiments the formulation has a neat pH from about 3 to about 5. In some preferred embodiments, granular laundry products are typically formulated to have a pH from about 8 to about 11. Techniques for controlling pH at recommended usage levels include the use of buffers, alkalis, acids, etc., and are well known to those skilled in the art.

In some particularly preferred embodiments, when at least one neutral metalloprotease is employed in a granular composition or liquid, the neutral metalloprotease is in the form of an encapsulated particle to protect the enzyme from other components of the granular composition during storage. In addition, encapsulation also provides a means of controlling the availability of the neutral metalloprotease(s) during the cleaning process and may enhance performance of the neutral metalloprotease(s). It is contemplated that the encapsulated neutral metalloproteases of the present invention will find use in various settings. It is also intended that the neutral metalloprotease be encapsulated using any suitable encapsulating material(s) and method(s) known in the art.

In some preferred embodiments, the encapsulating material typically encapsulates at least part of the neutral metalloprotease catalyst. In some embodiments, the encapsulating material is water-soluble and/or water-dispersible. In some additional embodiments, the encapsulating material has a glass transition temperature (Tg) of 0° C. or higher (See e.g., WO 97/11151, particularly from page 6, line 25 to page 7, line 2, for more information regarding glass transition temperatures).

In some embodiments, the encapsulating material is chosen from carbohydrates, natural or synthetic gums, chitin and chitosan, cellulose and cellulose derivatives, silicates, phosphates, borates, polyvinyl alcohol, polyethylene glycol, paraffin waxes and combinations thereof. In some embodiments in which the encapsulating material is a carbohydrate, it is chosen from monosaccharides, oligosaccharides, polysaccharides, and combinations thereof. In some preferred embodiments, the encapsulating material is a starch (See e.g., EP 0 922 499; U.S. Pat. No. 4,977,252. U.S. Pat. No. 5,354,559, and U.S. Pat. No. 5,935,826, for descriptions of some exemplary starches).

In additional embodiments, the encapsulating material comprises a microsphere made from plastic (e.g., thermoplastics, acrylonitrile, methacrylonitrile, polyacrylonitrile, polymethacrylonitrile and mixtures thereof; commercially available microspheres that find use include, but are not limited to EXPANCEL® [Casco Products, Stockholm, Sweden], PM 6545, PM 6550, PM 7220, PM 7228, EXTENDOSPHERES®, and Q-CEL® [PQ Corp., Valley Forge, Pa.], LUXSIL® and SPHERICEL® [Potters Industries, Inc., Carlstadt, N.J. and Valley Forge, Pa.]).

Processes of Making and Using of Applicants' Cleaning Composition

In some preferred embodiments compositions of the present invention are formulated into any suitable form and prepared by any process chosen by the formulator, (See e.g., U.S. Pat. No. 5,879,584, U.S. Pat. No. 5,691,297, U.S. Pat.

No. 5,574,005, U.S. Pat. No. 5,569,645, U.S. Pat. No. 5,565,422, U.S. Pat. No. 5,516,448, U.S. Pat. No. 5,489,392, and U.S. Pat. No. 5,486,303, for some non-limiting examples). In some embodiments in which a low pH cleaning composition is desired, the pH of such composition is adjusted via the addition of an acidic material such as HCl.

Adjunct Materials

While not essential for the purposes of the present invention, in some embodiments, the non-limiting list of adjuncts described herein are suitable for use in the cleaning compositions of the present invention. Indeed, in some embodiments, adjuncts are incorporated into the cleaning compositions of the present invention. In some embodiments, adjunct materials assist and/or enhance cleaning performance, treat the substrate to be cleaned, and/or modify the aesthetics of the cleaning composition (e.g., perfumes, colorants, dyes, etc.). It is understood that such adjuncts are in addition to the neutral metalloproteases of the present invention. The precise nature of these additional components, and levels of incorporation thereof, depends on the physical form of the composition and the nature of the cleaning operation for which it is to be used. Suitable adjunct materials include, but are not limited to, surfactants, builders, chelating agents, dye transfer inhibiting agents, deposition aids, dispersants, additional enzymes, and enzyme stabilizers, catalytic materials, bleach activators, bleach boosters, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, processing aids and/or pigments. In addition to those provided explicitly herein, additional examples are known in the art (See e.g., U.S. Pat. Nos. 5,576,282, 6,306,812 B1 and 6,326,348 B1). In some embodiments, the aforementioned adjunct ingredients constitute the balance of the cleaning compositions of the present invention.

Surfactants—

In some embodiments, the cleaning compositions of the present invention comprise at least one surfactant or surfactant system, wherein the surfactant is chosen from nonionic surfactants, anionic surfactants, cationic surfactants, ampholytic surfactants, zwitterionic surfactants, semi-polar nonionic surfactants, and mixtures thereof. In some low pH cleaning composition embodiments (e.g., compositions having a neat pH of from about 3 to about 5), the composition typically does not contain alkyl ethoxylated sulfate, as it is believed that such surfactant may be hydrolyzed in acidic compositions.

In some embodiments, the surfactant is present at a level of from about 0.1% to about 60%, while in alternative embodiments, the level is from about 1% to about 50%, while in still further embodiments, the level is from about 5% to about 40%, by weight of the cleaning composition.

Builders—

In some embodiments, the cleaning compositions of the present invention comprise one or more detergent builders or builder systems. In some embodiments incorporating at least one builder, the cleaning compositions comprise at least about 1%, from about 3% to about 60% or even from about 5% to about 40% builder by weight of the cleaning composition.

Builders include, but are not limited to, the alkali metal, ammonium and alkanolammonium salts of polyphosphates, alkali metal silicates, alkaline earth and alkali metal carbonates, aluminosilicate builders polycarboxylate compounds. ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in various embodiments of the present invention.

Chelating Agents—

In some embodiments, the cleaning compositions of the present invention contain at least one chelating agent. Suitable chelating agents include, but are not limited to copper, iron and/or manganese chelating agents and mixtures thereof. In embodiments in which at least one chelating agent is used, the cleaning compositions of the present invention comprise from about 0.1% to about 15% or even from about 3.0% to about 10% chelating agent by weight of the subject cleaning composition.

Deposition Aid—

In some embodiments, the cleaning compositions of the present invention include at least one deposition aid. Suitable deposition aids include, but are not limited to polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

Dye Transfer Inhibiting Agents—

In some embodiments, the cleaning compositions of the present invention include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof.

In embodiments in which at least one dye transfer inhibiting agent is used, the cleaning compositions of the present invention comprise from about 0.0001% to about 10%, from about 0.01% to about 5%, or even from about 0.1% to about 3% by weight of the cleaning composition.

Dispersants—

In some embodiments, the cleaning compositions of the present invention contains at least one dispersants. Suitable water-soluble organic materials include, but are not limited to the homo- or co-polymeric acids or their salts, in which the polycarboxylic acid comprises at least two carboxyl radicals separated from each other by not more than two carbon atoms.

Enzymes—

In some embodiments, the cleaning compositions of the present invention comprise one or more detergent enzymes, which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. In some embodiments, a combination of enzymes is used (i.e., a "cocktail") comprising conventional applicable enzymes like protease, lipase, cutinase and/or cellulase in conjunction with amylase is used.

Enzyme Stabilizers—

In some embodiments of the present invention, the enzymes used in the detergent formulations of the present invention are stabilized. It is contemplated that various techniques for enzyme stabilization will find use in the present invention. For example, in some embodiments, the enzymes employed herein are stabilized by the presence of water-soluble sources of zinc (II), calcium (II) and/or magnesium (II) ions in the finished compositions that provide such ions to the enzymes, as well as. other metal ions (e.g., barium (II), scandium (II), iron (II), manganese (II), aluminum (III), Tin (II), cobalt (II), copper (II), Nickel (II), and oxovanadium (IV)).

Catalytic Metal Complexes—

In some embodiments, the cleaning compositions of the present invention contain one or more catalytic metal complexes. In some embodiments, a metal-containing bleach catalyst finds use. In some preferred embodiments, the metal bleach catalyst comprises a catalyst system comprising a transition metal cation of defined bleach catalytic activity, (e.g., copper, iron, titanium, ruthenium, tungsten, molybdenum, or manganese cations), an auxiliary metal cation having little or no bleach catalytic activity (e.g., zinc or aluminum cations), and a sequestrate having defined stability constants for the catalytic and auxiliary metal cations, particularly ethylenediaminetetraacetic acid, ethylenediaminetetra (methylenephosphonic acid) and water-soluble salts thereof are used (See e.g., U.S. Pat. No. 4,430,243).

In some embodiments, the cleaning compositions of the present invention are catalyzed by means of a manganese compound. Such compounds and levels of use are well known in the art (See e.g., U.S. Pat. No. 5,576,282).

In additional embodiments, cobalt bleach catalysts find use in the cleaning compositions of the present invention. Various cobalt bleach catalysts are known in the art (See e.g., U.S. Pat. No. 5,597,936, and U.S. Pat. No. 5,595,967). Such cobalt catalysts are readily prepared by known procedures (See e.g., U.S. Pat. No. 5,597,936, and U.S. Pat. No. 5,595,967).

In additional embodiments, the cleaning compositions of the present invention include a transition metal complex of a macropolycyclic rigid ligand ("MRL"). As a practical matter, and not by way of limitation, in some embodiments, the compositions and cleaning processes provided by the present invention are adjusted to provide on the order of at least one part per hundred million of the active MRL species in the aqueous washing medium, and in some preferred embodiments, provide from about 0.005 ppm to about 25 ppm, more preferably from about 0.05 ppm to about 10 ppm, and most preferably from about 0.1 ppm to about 5 ppm, of the MRL in the wash liquor.

Preferred transition-metals in the instant transition-metal bleach catalyst include, but are not limited to manganese, iron and chromium. Preferred MRLs also include, but are not limited to special ultra-rigid ligands that are cross-bridged (e.g., 5,12-diethyl-1,5,8,12-tetraazabicyclo[6.6.2] hexadecane). Suitable transition metal MRLs are readily prepared by known procedures (See e.g., WO 00/32601, and U.S. Pat. No. 6,225,464).

Processes of Making and Using Cleaning Compositions

The cleaning compositions of the present invention are formulated into any suitable form and prepared by any suitable process chosen by the formulator, (See e.g., U.S. Pat. No. 5,879,584, U.S. Pat. No. 5,691,297, U.S. Pat. No. 5,574,005, U.S. Pat. No. 5,569,645, U.S. Pat. No. 5,565,422, U.S. Pat. No. 5,516,448, U.S. Pat. No. 5,489,392, U.S. Pat. No. 5,486,303, U.S. Pat. No. 4,515,705, U.S. Pat. No. 4,537,706, U.S. Pat. No. 4,515,707, U.S. Pat. No. 4,550,862, U.S. Pat. No. 4,561,998, U.S. Pat. No. 4,597,898, U.S. Pat. No. 4,968,451, U.S. Pat. No. 5,565,145, U.S. Pat. No. 5,929,022, U.S. Pat. No. 6,294,514, and U.S. Pat. No. 6,376,445, all of which are incorporated herein by reference for some non-limiting examples).

Method of Use

In preferred embodiments, the cleaning compositions of the present invention find use in cleaning surfaces and/or fabrics. In some embodiments, at least a portion of the surface and/or fabric is contacted with at least one embodiment of the cleaning compositions of the present invention, in neat form or diluted in a wash liquor, and then the surface and/or fabric is optionally washed and/or rinsed. For purposes of the present invention, "washing" includes, but is not limited to, scrubbing, and mechanical agitation. In some embodiments, the fabric comprises any fabric capable of being laundered in normal consumer use conditions. In preferred embodiments, the cleaning compositions of the present invention are used at concentrations of from about 500 ppm to about 15,000 ppm in solution. In some embodiments in which the wash solvent is water, the water temperature typically ranges from about 5° C. to about 90° C. In some preferred embodiments for fabric cleaning, the water to fabric mass ratio is typically from about 1:1 to about 30:1.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: ° C. (degrees Centigrade); rpm (revolutions per minute); $H_2O$ (water); HCl (hydrochloric acid); aa and AA (amino acid); by (base pair); kb (kilobase pair); kD (kilodaltons); gm (grams); µg and ug (micrograms); mg (milligrams); ng (nanograms); µl and ul (microliters); ml (milliliters); mm (millimeters); nm (nanometers); µm and um (micrometer); M (molar); mM (millimolar); µM and uM (micromolar); U (units); V (volts); MW (molecular weight); sec (seconds); min(s) (minute/minutes); hr(s) (hour/hours); $MgCl_2$ (magnesium chloride); NaCl (sodium chloride); $OD_{280}$ (optical density at 280 nm); $OD_{405}$ (optical density at 405 nm); $OD_{600}$ (optical density at 600 nm); PAGE (polyacrylamide gel electrophoresis); EtOH (ethanol); PBS (phosphate buffered saline [150 mM NaCl, 10 mM sodium phosphate buffer, pH 7.2]); LAS (lauryl sodium sulfonate); SDS (sodium dodecyl sulfate); Tris (tris(hydroxymethyl)aminomethane); TAED (N,N,N'N'-tetraacetyl-ethylenediamine); BES (polyesstersulfone); MES (2-morpholinoethanesulfonic acid, monohydrate; f.w. 195.24; Sigma # M-3671); $CaCl_2$ (calcium chloride, anhydrous; f.w. 110.99; Sigma # C-4901); DMF (N,N-dimethylformamide, f.w. 73.09, d=0.95); Abz-AGLA-Nba (2-aminobenzoyl-L-alanyl-glycyl-L-leucyl-L-alanino-4-nitrobenzylamide, f.w. 583.65; Bachem # H-6675, VWR catalog #100040-598); SBG1% (Super Broth with Glucose; 6 g Soytone [Difco], 3 g yeast extract, 6 g NaCl, 6 g glucose); the pH was adjusted to 7.1 with NaOH prior to sterilization using methods known in the art; w/v (weight to volume); v/v (volume to volume); SEQUEST® (SEQUEST database search program, University of Washington); MS (mass spectroscopy); BMI (blood, milk, ink); SRI (Stain Removal Index); Npr and npr (neutral metalloprotease gene); Npr and npr (neutral metalloprotease enzyme); NprE and nprE (*B. amyloliquefaciens* neutral metalloprotease); PrT and prt (proteinase-T enzyme); and TLP (thermolysin-like protease).

The following abbreviations apply to companies whose products or services may have been referred to in the experimental examples: TIGR (The Institute for Genomic Research, Rockville, Md.); AATCC (American Association of Textile and Coloring Chemists); Amersham (Amersham Life Science, Inc. Arlington Heights, Ill.); Corning (Corning International, Corning, N.Y.); ICN (ICN Pharmaceuticals, Inc., Costa Mesa, Calif.); Pierce (Pierce Biotechnology, Rockford, Ill.); Equest (Equest, Warwick International Group, Inc., Flintshire, UK); EMPA (Eidgenossische Material Prufungs and Versuch Anstalt, St. Gallen, Switzerland); CFT (Center for Test Materials, Vlaardingen, The Netherlands); Amicon (Amicon, Inc., Beverly, Mass.); ATCC (American Type Culture Collection, Manassas, Va.); Becton Dickinson (Becton Dickinson Labware, Lincoln Park, N.J.); Perkin-Elmer (Perkin-Elmer, Wellesley, Mass.); Rainin (Rainin Instrument, LLC, Woburn, Mass.); Eppendorf (Eppendorf AG, Hamburg, Germany); Waters (Waters, Inc., Milford, Mass.); Perseptive Biosystems (Perseptive Biosystems, Ramsey, Minn.); Molecular Probes (Molecular Probes, Eugene, Oreg.); BioRad (BioRad, Richmond, Calif.); Clontech (CLONTECH Laboratories, Palo Alto, Calif.); Cargill (Cargill, Inc., Minneapolis, Minn.); Difco (Difco Laboratories, Detroit, Mich.); GIBCO BRL or Gibco BRL (Life Technologies, Inc., Gaithersburg, Md.); New Brunswick (New Brunswick Scientific Company, Inc., Edison, N.J.); Thermoelectron (Thermoelectron Corp., Waltham, Mass.); BMG (BMG Labtech, GmbH, Offenburg, Germany); Greiner (Greiner Bio-One, Kremsmuenster, Austria); Novagen (Novagen, Inc., Madison, Wis.); Novex (Novex, San Diego, Calif.); Finnzymes (Finnzymes OY, Finland) Qiagen (Qiagen, Inc., Valencia, Calif.); Invitrogen (Invitrogen Corp., Carlsbad, Calif.); Sigma (Sigma Chemical Co., St. Louis, Mo.); DuPont Instruments (Asheville, N.Y.); Global Medical Instrumentation or GMI (Global Medical Instrumentation; Ramsey, Minn.); MJ Research (MJ Research, Waltham, Mass.); Infors (Infors AG, Bottmingen, Switzerland); Stratagene (Stratagene Cloning Systems, La Jolla, Calif.); Roche (Hoffmann La Roche, Inc., Nutley, N.J.); Agilent (Agilent Technologies, Palo Alto, Calif.); S-Matrix (S-Matrix Corp., Eureka, Calif.); US Testing (United States Testing Co., Hoboken, N.Y.); West Coast Analytical Services (West Coast Analytical Services, Inc., Santa Fe Springs, Calif.); Ion Beam Analysis Laboratory (Ion Bean Analysis Laboratory, The University of Surrey Ion Beam Centre (Guildford, UK); BaChem (BaChem AG, Bubendorf, Switzerland); Molecular Devices (Molecular Devices, Inc., Sunnyvale, Calif.); MicroCal (Microcal, Inc., Northhampton, Mass.); Chemical Computing (Chemical Computing Corp., Montreal, Canada); NCBI (National Center for Biotechnology Information, Bethesda, Md.); Argo Bioanalytica (Argo Bioanalytica. Inc, New Jersey); Vydac (Grace Vydac, Hesperia, Calif.); Minolta (Konica Minolta, Ramsey, N.J.); Zeiss (Carl Zeiss, Inc., Thornwood, N.Y.); Sloning BioTechnology GmbH (Puchheim, Germany); and Procter and Gamble (Cincinnati, Ohio).

Example 1

Assays

The following assays were used in the examples described below. Any deviations from the protocols provided below are indicated in the examples. In these experiments, a spectrophotometer was used to measure the absorbance of the products formed after the completion of the reactions.

A. Bradford Assay for Protein Content Determination in 96-Well Plates

The Bradford Dye reagent (Quick Start) assay was used to determine the protein concentration in thermolysin samples on a microtiter plate (MTP) scale.

In this assay system, the chemical and reagent solutions used were:

Bradford Quick Start Dye Reagent™ (BIO-RAD Catalogue No. 500-0205)

Dilution Buffer (10 mM NaCl, 0.1 mM $CaCl_2$, 0.005% TWEEN®-80)

The equipment used was a Biomek FX Robot (Beckman Coulter) and a SpectraMAX MTP Reader (type 340; Molecular Devices). MTPs were obtained from Costar (type 9017).

In the test, 200 µl Bradford Dye Reagent was pipetted into each well, followed by the addition of 15 µl dilution buffer. Finally, 10 µl of the thermolysin containing filtered culture supernatants was added to the wells. After thorough mixing, the MTPs were incubated for at least 10 minutes at room temperature. Possible air bubbles were blown away and the absorbance of the wells was read at 595 nm.

To determine the protein concentration, the background reading (i.e., from uninoculated wells) was subtracted from the sample readings. The resulting $OD_{595}$ values provided a relative measure of the protein content in the samples. The Bradford results were linear with respect to thermolysin protein concentrations between 10 to 100 µg protein per ml.

B. Microswatch Assay for Testing Protease Performance

The stain removal performance of thermolysin and variants thereof was determined using microswatches (EMPA 116) on a MTP scale. Thermolysin containing protease samples were obtained from filtered broth of cultures grown in microtiter plates for 3 days at 37° C. with shaking at 280 rpm under humidified aeration.

In this assay system, the chemical and reagent solutions used were:

Thermolysin containing culture supernatants (~100-200 µg protein per ml)

TIDE® 2× (nil enzymes) detergent (P&G)

Dilution Buffer (10 mM NaCl, 0.1 mM $CaCl_2$, 0.005% TWEEN®-80)

The equipment used was a Biomek FX Robot (Beckman Coulter), a SpectraMAX MTP Reader (type 340; Molecular Devices), and an iEMS incubator/shaker (Thermo/Labsystems). MTPs were obtained from Costar (type 9017).

TIDE® 2× Liquid Detergent Preparation (US Conditions):

Milli-Q water was adjusted to 6 gpg water hardness using a (Ca/Mg 3:1) hardness stock solution (282.3 g/L $CaCl_2.2H_2O$, 130.1 g/L $MgCl_2.6H_2O$), 0.78 g/l detergent TIDE® 2× was added, and the detergent solution was stirred vigorously for at least 15 minutes. Then, 5 mM HEPES was added and the pH adjusted to 8.2.

Microswatches:

Microswatches of ¼ inch circular diameter were obtained from CFT (Vlaardingen, The Netherlands). Before cutting the swatches, the fabric (EMPA 116) was pre-washed in de-ionised water for 20 minutes at ambient temperature, and subsequently air-dried.

Two microswatches were placed vertically into each well of a 96-well microtiter plate to expose the whole surface area (i.e., not flat on the bottom of the well).

Test Method:

The incubator was set to 20° C. The filtered culture broth samples were tested at an appropriate concentration by dilution with a mixture of 10 mM NaCl, 0.1 mM CaCl$_2$, 0.005% TWEEN®-80 solution. The detergent solution was prepared as described above. Then, 190 µl of detergent solution were added to each well of the MTP, containing microswatches. To this mixture, 10 µl of diluted enzyme solution were added to each well (to provide a total volume of 200 µl/well). The MTP was covered with a plate seal and placed in an incubator for 30 minutes at 20° C., with agitation at 1400 rpm (iEMS incubator). Following incubation under the appropriate conditions, 100 µl of solution from each well was removed and placed into a new MTP. Subsequently this MTP, containing 100 µl of solution/well, was read at 405 nm in a MTP-Reader. Blank controls, containing 2 microswatches/well and detergent, without the addition of thermolysin containing samples, were also included in the test.

Calculation of the BMI (Blood/Milk/Ink) Performance:

The observed absorbance value was corrected for the blank value (obtained after incubation of microswatches in the absence of added enzyme). The resulting absorbance was a measure for the hydrolytic activity. For each sample (thermolysin or a variant) the performance index (PI) was calculated. The performance index is a comparison of the performance of the variant (actual value) and the standard thermolysin enzyme (theoretical value) at the same protein concentration. In addition, the theoretical values were calculated, using the parameters of the Langmuir equation of the standard enzyme.

A performance index greater than 1 (PI>1) identified a better variant (as compared to the standard [e.g., wild-type]), while a PI of 1 (PI=1) identified a variant that performs the same as the standard, and a PI less than 1 (PI<1) identified a variant that performs worse than the standard. Thus, the PI identified winners, as well as variants that are less desirable for use under certain circumstances.

C. Stability Assay in the Presence of Detergent

The stability of thermolysin and variants thereof was measured after incubation under defined conditions in the presence of 25% TIDE® 2× detergent. The initial and residual activity was determined.

In this assay system, the chemical and reagent solutions used were:
thermolysin containing culture supernatants (~100-200 µg protein per ml)
TIDE® 2× liquid detergent with and without DTPA chelator (P&G)
27.5% TIDE® 2× detergent solution with DTPA in 5.5 mM HEPES buffer, pH 8.2 (TIDE®+solution)
27.5% TIDE® 2× detergent solution w/o DTPA in 5.5 mM HEPES buffer, pH 8.2 (TIDE®−solution)
MES assay buffer (55.5 mM MES/NaOH, 2.6 mM CaCl$_2$, 0.005% TWEEN®-80, pH 6.5)

The equipment used was a Biomek FX Robot (Beckman Coulter), a fluorescence spectrophotometer (FLUOstar Optima; BMG), an iEMS incubator/shaker (Thermo/Labsystems). MTPs were obtained from Costar (type 9017) and from Greiner (black plate, type 655076).

Test Method

Unstressed Conditions:
First, 20 µl thermolysin containing culture supernatant was diluted with 180 µl MES assay buffer. Then, 20 µl diluted supernatant was diluted further with 180 µl MES assay buffer. Subsequently 10 µl of this dilution was transferred into 190 µl AGLA-substrate solution in a pre-warmed plate (Greiner 655076) at 25° C. Any air bubbles present were blown away and the plate was measured according to the AGLA protease assay protocol described below.

Stressed Conditions:
First, 20 µl of culture supernatant was diluted with 180 µl 27.5% TIDE®+detergent solution and placed in the iEMS shaker. The plate covered with a plate seal was incubated for a total of 60 minutes at 32° C. at 900 rpm. In addition, 20 µl of culture supernatant was diluted with 180 µl 27.5% TIDE®−solution and placed in the iEMS shaker. This plate covered with a plate seal was incubated for a total of 180 minutes at 50° C. at 900 rpm.

Subsequently after the respective incubations, 20 µl of either of these solutions were diluted with 180 µl MES assay buffer and 10 µl of this dilution were diluted with 190 µl AGLA-substrate solution in a pre-warmed plate (Greiner 655076) at 25° C.

Any air bubbles present were blown away and the plate was measured according to the AGLA protease assay protocol described below.

Calculations of TIDE® 2× Stability

Fluorescence measurements were taken at excitation of 350 nm and emission of 420 nm. The spectrofluorometer software calculated the reaction rates (=slope) of the increase in fluorescence for each well to a linearly regressed line of (milli-) RFU/min. The ratio of the residual and initial AGLA activity was used to express the 25% TIDE® 2× stability as follows:

Percentage of residual activity=[slope of stressed]* 100/[slope of unstressed]

For each sample (thermolysin and variants thereof) the performance index was calculated by dividing the residual activity of the variant by the residual activity of thermolysin. The performance index compared the stability of the variant and the standard thermolysin enzyme (e.g., wild type or parental enzyme), determined under the same conditions.

A performance index (PI) greater than 1 (PI>1) identified a better variant (as compared to the standard [e.g., wild-type]), while a PI of 1 (PI=1) identified a variant that displayed the same stability as the standard, and a PI less than 1 (PI<1) identified a variant that was less stable as compared to the standard. Thus, the PI identified winners, as well as variants that are less desirable for use under certain circumstances.

D. 2-Aminobenzoyl-L-alanyl-L-glycyl-L-leucyl-L-alanino-4-nitrobenzylamide (Abz-AGLA-Nba) Protease Assay The method described herein provides a degree of technical detail that yields reproducible protease assay data independent of time and place. While the assay can be adapted to a given laboratory condition, any data obtained through a modified procedure must be reconciled with results produced by the original method. Neutral metalloproteases cleave the peptide bond between glycyl- and leucyl- of 2-Aminobenzoyl-L-alanyl-L-glycyl-L-leucyl-L-alanino-4-nitrobenzylamide (Abz-AGLA-Nba). Free 2-Aminobenzoyl-L-alanylglycine (Abz-AG) in solution has a fluorescence emission maximum at 415 nm with an excitation maximum of 340 nm. Fluorescence of Abz-AG is quenched by nitrobenzylamide in the intact Abz-AGLA-Nba molecule.

In these experiments, the liberation of Abz-AG by protease cleavage of Abz-AGLA-Nba was monitored by fluorescence spectrometry (Ex. 350/Em. 420). The rate of appearance of Abz-AG was a measure of proteolytic activity. In this assay system, the chemical and reagent solutions used were:
MES substrate buffer—52.5 mM MES, 2.5 mM CaCl$_2$, 0.005% TWEEN®-80, pH 6.5

MES assay buffer—55.5 mM MES, 2.6 mM CaCl$_2$, 0.005% TWEEN®-80, pH 6.5

Abz-AGLA-Nba stock solution—48 mM Abz-AGLA-Nba in dimethylformamid (28.2 mg/ml DMF)

The equipment used was a Biomek FX Robot (Beckman Coulter), a spectrofluorometer (FLUOstar Optima; BMG), an iEMS incubator/shaker (Thermo/Labsystems) and Innova incubator (Innova-4230; New Brunswick). MTPs were obtained from Costar (type 9017) and from Greiner (black plate, type 655076).

Test Method

The Abz-AGLA-Nba assay solution was prepared by adding 1 ml of the Abz-AGLA-Nba stock to 19 ml MES substrate buffer and mixed well for at least 2 minutes. Subsequently the thermolysin or variants thereof containing culture supernatants were diluted with MES assay buffer to a concentration of 1-6 µg protein per ml.

The assay was performed by adding 10 µl of diluted protease solution to each well, followed by the addition of 190 µl Abz-AGLA-Nba assay solution that was pre-equilibrated for at least 15 minutes at 25° C. The solutions were vigorously mixed, and the liberation of Abz-AG by protease cleavage of Abz-AGLA-Nba was monitored by fluorescence spectrometry at 25° C. in kinetic mode with excitation set at 350 nm and emission set at 420 nm. The rate of appearance of Abz-AG was a measure of proteolytic activity in the samples. The protease activity was expressed as RFU (relative fluorescence units·min$^{-1}$).

Example 2

Thermolysin Production in *B. subtilis*

In this Example, experiments conducted to produce thermolysin in *B. subtilis* are described. The full-length thermolysin of *Geobacillus caldoproteolyticus* is greater than 99% identical to the thermolysin precursor of *Bacillus thermoproteolyticus* Rokko, and to the bacillolysin (NprS) precursor of *Bacillus stearothermophilus*. As such the terms "thermolysin," "bacillolysin," "proteinase-T" and "PrT" are used interchangeably herein to refer to the neutral metalloprotease enzyme of *G. caldoproteolyticus*. The DNA sequence (thermolysin leader, thermolysin pro and thermolysin mature from *Geobacillus caldoproteolyticus*) provided below, encodes the thermolysin precursor protein:

(SEQ ID NO: 1)
ATGAAAATGAAAATGAAATTAGCATCGTTTGGTCTTGCAGCAGGACTAG

CGGCCCAAGTATTTTTACCTTACAATGCGCTGGCTTCAACGGAACACGT

TACATGGAACCAACAATTTCAAACCCCTCAATTCATCTCCGGTGATCTG

CTGAAAGTGAATGGCACATCCCCAGAAGAACTCGTCTATCAATATGTTG

AAAAAAACGAAAACAAGTTTAAATTTCATGAAAACGCTAAGGATACTCT

ACAATTGAAAGAAAAGAAAAATGATAACCTTGGTTTTACGTTTATGCGC

TTCCAACAAACGTATAAAGGGATTCCTGTGTTTGGAGCAGTAGTAACTG

CGCACGTGAAAGATGGCACGCTGACGGCGCTATCAGGGACACTGATTCC

GAATTTGGACACGAAAGGATCCTTAAAAAGCGGGAAGAAATTGAGTGAG

AAACAAGCGCGTGACATTGCTGAAAAAGATTTAGTGGCAAATGTAACAA

AGGAAGTACCGGAATATGAACAGGGAAAAGACACCGAGTTTGTTGTTTA

TGTCAATGGGGACGAGGCTTCTTTAGCGTACGTTGTCAATTTAAACTTT

TTAACTCCTGAACCAGGAAACTGGCTGTATATCATTGATGCCGTAGACG

GAAAAATTTTAAATAAATTTAACCAACTTGACGCCGCAAAACCAGGTGA

TGTGAAGTCGATAACAGGAACATCAACTGTCGGAGTGGGAAGAGGAGTA

CTTGGTGATCAAAAAAATATTAATACAACCTACTCTACGTACTACTATT

TACAAGATAATACGCGTGGAAATGGGATTTTCACGTATGATGCGAAATA

CCGTACGACATTGCCGGGAAGCTTATGGGCAGATGCAGATAACCAATTT

TTTGCGAGCTATGATGCTCCAGCGGTTGATGCTCATTATTACGCTGGTG

TGACATATGACTACTATAAAAATGTTCATAACCGTCTCAGTTACGACGG

AAATAATGCAGCTATTAGATCATCCGTTCATTATAGCCAAGGCTATAAT

AACGCATTTTGGAACGGTTCGCAAATGGTGTATGGCGATGGTGATGGTC

AAACATTTATTCCACTTTCTGGTGGTATTGATGTGGTCGCACATGAGTT

AACGCATGCGGTAACCGATTATACAGCCGGACTCATTTATCAAAACGAA

TCTGGTGCAATTAATGAGGCAATATCTGATATTTTTGGAACGTTAGTCG

AATTTTACGCTAACAAAAATCCAGATTGGGAAATTGGAGAGGATGTGTA

TACACCTGGTATTTCAGGGGATTCGCTCCGTTCGATGTCCGATCCGGCA

AAGTATGGTGATCCAGATCACTATTCAAAGCGCTATACAGGCACGCAAG

ATAATGGCGGGGTTCATATCAATAGCGGAATTATCAACAAAGCCGCTTA

TTTGATTAGCCAAGGCGGTACGCATTACGGTGTGAGTGTTGTCGGAATC

GGACGCGATAAATTGGGGAAAATTTTCTATCGTGCATTAACGCAATATT

TAACACCAACGTCCAACTTTAGCCAACTTCGTGCTGCCGCTGTTCAATC

AGCCACTGACTTGTACGGTTCGACAAGCCAGGAAGTCGCTTCTGTGAAG

CAGGCCTTTGATGCGGTAGGGGTGAAATAA

In the above sequence, bold indicates the DNA encoding the mature thermolysin protease, standard font indicates the DNA encoding the leader sequence (thermolysin leader), and underlined text indicates DNA encoding the pro sequence (thermolysin pro). The amino acid sequence (thermolysin leader, thermolysin pro and thermolysin mature DNA sequence) provided below (SEQ ID NO:2), corresponds to the full length thermolysin precursor protein. In this sequence, underlined indicates the pro sequence and bold indicates the mature thermolysin protease.

(SEQ ID NO: 2)
MKMKMKLASFGLAAGLAAQVFLPYNALASTEHVTWNQQFQTPQFISGD

LLKVNGTSPEELVYQYVEKNENKFKFHENAKDTLQLKEKKNDNLGFTF

MRFQQTYKGIPVFGAVVTAHVKDGTLTALSGTLIPNLDTKGSLKSGKK

LSEKQARDIAEKDLVANVTKEVPEYEQGKDTEFVVYVNGDEASLAYVV

NLNFLTPEPGNWLYIIDAVDGKILNKFNQLDAAKPGDVKSITGTSTVG

VGRGVLGDQKNINTTYSTYYYLQDNTRGNGIFTYDAKYRTTLPGSLWA

DADNQFFASYDAPAVDAHYYAGVTYDYYKNVHNRLSYDGNNAAIRSSV

HYSQGYNNAFWNGSQMVYGDGDGQTFIPLSGGIDVVAHELTHAVTDYT

AGLIYQNESGAINEAISDIFGTLVEFYANKNPDWEIGEDVYTPGISGD

SLRSMSDPAKYGDPDHYSKRYTGTQDNGGVHINSGIINKAAYLISQGG

-continued

THYGVSVVGIGRDKLGKIFYRALTQYLTPTSNFSQLRAAAVQSATDLY

GSTSQEVASVKQAFDAVGVK

The mature thermolysin sequence is set forth as SEQ ID NO:3 and shown in FIG. 1. This sequence was used as the basis for making the variant libraries describe herein.

(SEQ ID NO: 3)
ITGTSTVGVGRGVLGDQKNINTTYSTYYYLQDNTRGNGIFTYDAKYRT

TLPGSLWADADNQFFASYDAPAVDAHYYAGVTYDYYKNVHNRLSYDGN

NAAIRSSVHYSQGYNNAFWNGSQMVYGDGDGQTFIPLSGGIDVVAHE

LTHAVTDYTAGLIYQNESGAINEAISDIFGTLVEFYANKNPDWEIGED

VYTPGISGDSLRSMSDPAKYGDPDHYSKRYTGTQDNGGVHINSGIINK

AAYLISQGGTHYGVSVVGIGRDKLGKIFYRALTQYLTPTSNFSQLRAA

AVQSATDLYGSTSQEVASVKQAFDAVGVK

The pHPLT-thermolysin expression vector was constructed by amplifying the thermolysin gene from genomic DNA of *Geobacillus caldoproteolyticus* (Chen et al., Extremophiles, 8:489-498, 2004) and from pHPLT plasmid DNA (van Solingen et al., Extremophiles, 5:333-341, 2001). A map for the pHPLT plasmid is provided in FIG. 2. This plasmid contains the thermostable amylase LAT promoter ($P_{LAT}$) of *Bacillus licheniformis* to drive expression of thermolysin. The thermolysin gene was amplified from the genomic DNA using Finnzymes (Finnzymes OY, Espoo, Finland) Phusion High-Fidelity DNA Polymerase (Catalog No. F-530L) and the following primers:

pHPLT-ProT-FW:
(SEQ ID NO: 4)
GAGAGGGTAAAGAATGAAAATGAAAATGAAATTAGCATC proT-EcoRI-RV:
(SEQ ID NO: 5)
GTTAACCTGCAGGAATTCTTATTTCACCCCTACCGCATCAAAGGCC The pHPLT fragment was amplified from the plasmid pHPLT using Finnzymes Phusion High-Fidelity DNA Polymerase and the following primers:

pHPLT-ProT-RV:
(SEQ ID NO: 6)
CATTTTCATTTTCATTCTTTACCCTCTCCTTTTGCTAGAC proT-EcoRI-FW:
(SEQ ID NO: 7)
CCATAAGAATTCCTGCAGGTTAACAGAGGACGGATTTCCTGAAGG The following PCR conditions were used to amplify both pieces:
98° C. for 30 sec, 30×(98° C. for 10 sec, 55° C. for 20 sec, and 72° C. for 45 sec (thermolysin) or 72° C. for 80 sec (pHPLT)), followed by 72° C. for 5 min. The resulting PCR products were run on an E-gel (Invitrogen), excised, and purified with a gel extraction kit (Qiagen). In addition, a PCR overlap extension fusion (Ho, Gene, 15:51-59, 1989) was used to fuse the above gene fragments with High fidelity platinum Taq DNA polymerase (Invitrogen) using the following primers:

proT-EcoRI-FW:
(SEQ ID NO: 7)
CCATAAGAATTCCTGCAGGTTAACAGAGGACGGATTTCCTGAAGG proT-EcoRI-RV:
(SEQ ID NO: 5)
GTTAACCTGCAGGAATTCTTATTTCACCCCTACCGCATCAAAGGCC The following conditions were used for these reactions:
94° C. for 2 min, 25×(94° C. for 30 sec, 55° C. for 30 sec, and 68° C. for 5 min) followed by 68° C. for 5 min. The resulting PCR fusion product was run on an E-gel (Invitrogen), excised, and purified with a gel extraction kit (Qiagen). The purified fusion product was cut (PstI) and self-ligated (T4 DNA Ligase, Invitrogen). A map of the pHPLT-thermolysin expression vector is provided in FIG. 3, while the DNA sequence of the pHPLT-thermolysin expression vector (SEQ ID NO:8) is provided in FIG. 4.

The ligation mixture was used to transform *B. subtilis* SC6.1 (phenotype: ΔaprE, ΔnprE, oppA, ΔspoIIE, degUHy32, ΔamyE::(xylR,pxylA-comK). Transformation of *B. subtilis* SC6.1 strain was performed as described in WO 02/14490, incorporated herein by reference. Selective growth of *B. subtilis* transformants containing the pHPLT-thermolysin vector was done in shake flasks containing, 25 ml MBD medium (a MOPS based defined medium), with 20 mg/L neomycin. Culturing resulted in the production of secreted mature thermolysin enzyme having proteolytic activity. Gel analysis was performed using NuPage Novex 10% Bis-Tris gels (Invitrogen, Catalog No. NP0301BOX). To prepare samples for analysis, 2 volumes of supernatant were mixed with 1 volume 1M HCl, 1 volume 4×LDS sample buffer (Invitrogen, Catalog No. NP0007), and 1% PMSF (20 mg/ml), and subsequently heated for 10 minutes at 70° C. Then, 25 μL of each sample was loaded onto the gel, adjacent to 10 μL of SeeBlue plus 2 pre-stained protein standards (Invitrogen, Catalog No. LC5925). The results clearly demonstrated that the thermolysin cloning strategy described in this example is suitable for production of active recombinant thermolysin in *B. subtilis*.

Example 3

Generation of Thermolysin Site Evaluation Libraries (SELs)

In this Example, methods used in the construction of thermolysin SELs are described. As previously indicated, the terms "thermolysin," "bacillolysin," "proteinase-T" and "PrT" are used interchangeably throughout to refer to the neutral metalloprotease enzyme of *G. caldoproteolyticus*. The pHPLT-thermolysin vector (FIG. 3) contains the thermolysin expression cassette, which served as a template DNA for the site evaluation libraries. Every thermolysin site evaluation library contains a collection of *B. subtilis* clones, all expressing a specific thermolysin variant. Each library contains *B. subtilis* clones, maximally including 20 different variants. For example, thermolysin SEL 27 contains variants in which the DNA triplet coding for tyrosine at position 27 of the mature thermolysin enzyme is replaced by another DNA triplet encoding: Alanine, Aspartic acid, Cysteine, Glutamic acid, Phenylalanine, Glycine, Histidine, Isoleucine, Lysine, Leucine, Methionine, Asparagine, Proline, Glutamine, Arginine, Serine, Threonine, Valine, Tryptophan or Tyrosine.

Briefly, DNA triplets of specific positions in the DNA coding strand of the mature thermolysin are replaced. The mutated thermolysin fragments are subsequently ligated to pHPLT. The pHPLT-thermolysin variant plasmids are used to transform *B. subtilis* SC6.1 The production of prt variants was done using the gene synthesis products and services of Sloning BioTechnology GmbH (Puchheim, Germany). The specific mutation of each variant was confirmed by DNA sequencing.

Example 4

Preparation of Crude Thermolysin Samples

The thermolysin (also referred to as Proteinase-T or PrT) variant proteins were produced by culturing the *B. subtilis* transformants in 96 well MTP at 37° C. for 68 hours in MBD medium (a MOPS based defined medium) including 10 mg/L neomycin. MBD medium was made essentially as known in the art (See, Neidhardt et al., J Bacteriol, 119: 736-747, 1974), except that $NH_4Cl$, $FeSO_4$, and $CaCl_2$ were omitted from the base medium, 3 mM $K_2HPO_4$ was used, and the base medium was supplemented with 60 mM urea, 75 g/L glucose, and 1% soytone. Also, the micronutrients were made up as a 100× stock containing in one liter, 400 mg $FeSO_4.7H_2O$, 100 mg $MnSO_4.H_2O$, 100 mg $ZnSO_4.7H_2O$, 50 mg $CuCl_2.2H_2O$, 100 mg $CoCl_2.6H_2O$, 100 mg $NaMoO_4.2H_2O$, 100 mg $Na_2B_4O_7.10H_2O$, 10 ml of 1M $CaCl_2$, and 10 ml of 0.5 M sodium citrate.

Example 5

Stability of Thermolysin in Heavy Duty Liquid (HDL) Detergent

Unilever detergent ALL Small and Mighty, P&G TIDE® Fresh Breeze, P&G TIDE® 2× Fresh Breeze were purchased from Walmart. The commercially available detergents were heated at 90° C. for 1 hour and then cooled to room temperature, to inactivate the proteases in these cleaning compositions. Thermolysin (also referred to as Proteinase-T or PrT) in lyophilized powder was purchased from Sigma, and dissolved in 100 mM Tris pH 7 and 50% propylene glycol at 20 mg/ml. NprE was purified from *Bacillus* sp. supernatant through ion-exchange chromatography. To 1 ml of heat-treated detergent in an eppendorf tube, 800 μg of thermolysin or NprE was added. The tube was mixed well on a rocker for 15 min at room temperature, and then incubated at 25° C. or 32° C. At different time points, remaining proteinase activity was measured using an AGLA assay as described above in Example 1. Briefly, 10 μl of sample was diluted 441 fold in AGLA buffer (50 mM MES, pH 6.5, 0.005% Tween 80, 2.5 mM $CaCl_2$), then 10 μl of diluted sample was added into 200 μl of AGLA substrate (2.4 mM Abz-AGLA-Nba in AGLA buffer). Excitation at 350 nm and emission at 415 nm was monitored for the first 100 seconds, and the initial slope was recorded as enzyme activity. The enzyme activity was plotted against time, and curves were fitted with exponential decay.

Figure 5:
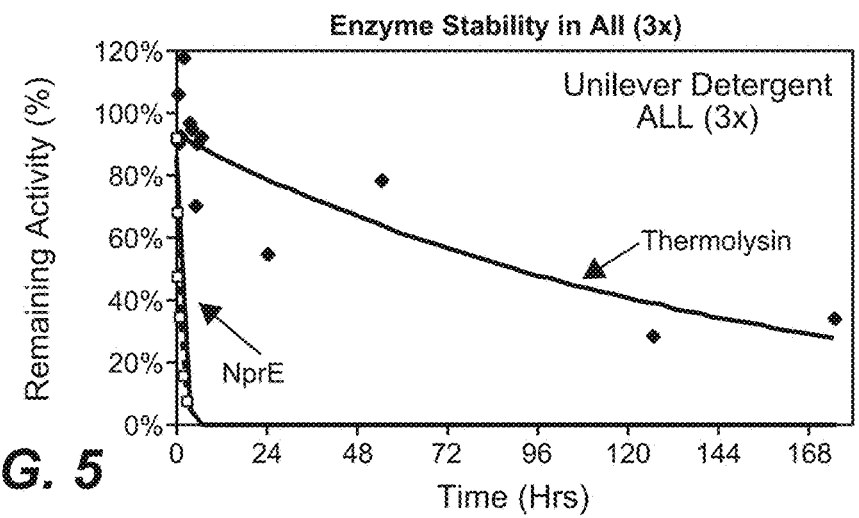
FIG. 5 provides a graph comparing protease activity of thermolysin and NprE after incubation at room temperature in Unilever ALL Small and Mighty 3× detergent.
Figure 6:
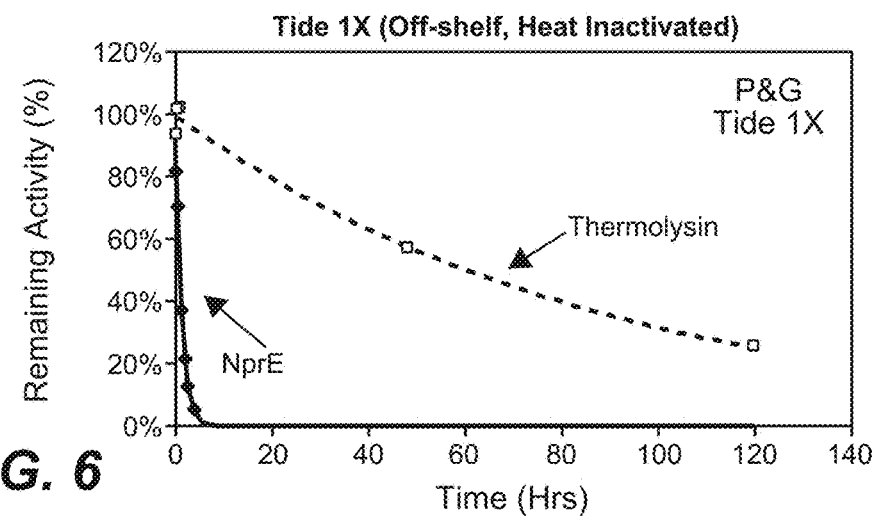
FIG. 6 provides a graph comparing protease activity of thermolysin and NprE after incubation at room temperature in Proctor & Gamble TIDE® Fresh Breeze 1× detergent.
Figure 7:
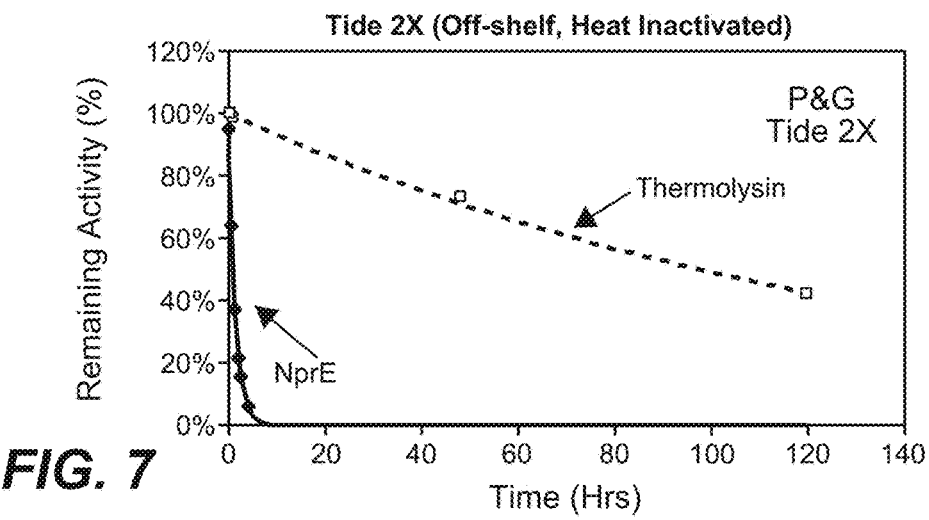
FIG. 7 provides a graph comparing protease activity of thermolysin and NprE after incubation at room temperature in Proctor & Gamble TIDE® Fresh Breeze 2× detergent.

As shown in FIG. 5, thermolysin is 140 fold more stable than NprE in Unilever All Small & Mighty at room temperature. Similarly as shown in FIG. 6, thermolysin is 68 fold more stable than NprE in P&G TIDE® at 32° C., while FIG. 7 shows that thermolysin is 98 fold more stable than NprE in P&G TIDE® 2× at 32° C. Thus, thermolysin is much more stable than NprE in Unilever detergent ALL (3×), P&G TIDE® 1× Fresh Breeze and P&G TIDE® 2× Fresh Breeze.

Example 6

Figure 8:
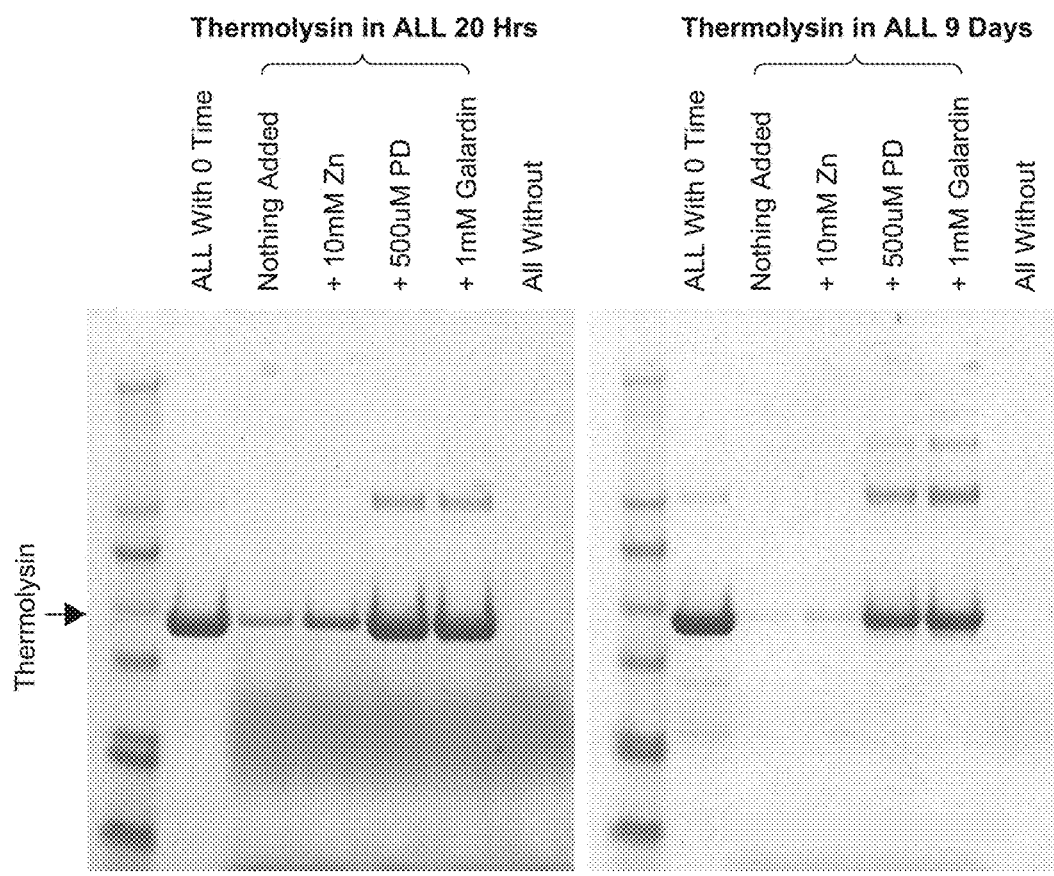
FIG. 8 shows an SDS-PAGE analysis of thermolysin stability after prolonged incubation in Unilever ALL small and mighty detergent in the presence and absence of known metalloproteinase inhibitors.

Metalloproteinase Inhibitors can Improve Thermolysin Stability in Heavy Duty Liquid (HDL) Detergent Zinc Chloride, Phosphoramidon, Galardin are known metalloproteinase inhibitors. They were purchased from Sigma and dissolved in water or DMSO. Different concentrations of the inhibitors were premixed with thermolysin (also referred to as Proteinase-T or PrT) for 10 min at room temperature. Then the inhibitors were added into Unilever detergent ALL Small and Mighty so that the final concentration of thermolysin was 800 μg/ml in a total volume of 1 ml. At different time points, samples were taken and precipitated with TCA. Briefly, 10 μl sample of detergent with enzyme was added into 500 μl of 0.2 N HCl on ice, and then 500 μl of 20% TCA was added. The tubes were mixed and incubated on ice for 20 min. The pellet was collected and washed with 90% ice-cold acetone. The pellet was dissolved in sample loading buffer (Invitrogen) for SDS-PAGE analysis. As shown in FIG. 8, both 500 μM Phosphoramidon (PD) and 1 mM Galardin significantly stabilize thermolysin in detergent.

Example 7

Stain Removal Performance of Thermolysin Variants in a TIDE® 2× Microswatch Assay In this example, experiments were conducted to determine the stain removal performance of various singly substituted thermolysin (also referred to herein as Proteinase-T or PrT) variants. As described in Example 1, the stain cleaning performance of thermolysin variants was done utilizing a blood/milk/ink (BMI) microswatch assay. Briefly the cleaning performance of chosen single-substitution thermolysin variants was assessed in a TIDE® 2× microswatch assay. Table 7-1 provides performance indices for the tested variants (e.g., showing improved performance as compared to wild-type thermolysin enzyme). Those variants with a performance index greater than 1 (PI>1) have improved performance. As indicated by these results, numerous variants having single amino acid substitutions performed better than wild-type enzyme in this assay system.

TABLE 7-1

Stain Removal For Variants With PI > 1

| Variant | PI | Variant | PI |
|---|---|---|---|
| T006G | 1.13 | F063P | 1.20 |
| T006H | 1.01 | S065K | 1.29 |
| T006I | 1.27 | S065Y | 1.05 |
| T006K | 1.76 | Y075G | 1.04 |
| T006M | 1.05 | Y075M | 1.14 |
| T006N | 1.23 | Y075T | 1.01 |
| T006P | 1.05 | Q128H | 1.39 |
| T006Q | 1.19 | Q128I | 1.34 |
| T006R | 1.58 | Q128L | 1.04 |
| T006V | 1.04 | Q128M | 1.10 |
| T006W | 1.14 | Q128V | 1.07 |
| T006Y | 1.06 | Q128Y | 1.13 |
| V007F | 1.08 | Y151D | 1.08 |
| V007K | 1.32 | Y151E | 1.11 |
| V007K | 1.60 | Y151H | 1.17 |
| V007L | 1.16 | Y151K | 1.03 |
| V007M | 1.01 | Y151M | 1.06 |
| V007P | 1.27 | Y151N | 1.19 |

TABLE 7-1-continued

Stain Removal For Variants With PI > 1

| Variant | PI | Variant | PI |
|---|---|---|---|
| V007Q | 1.20 | Y151Q | 1.29 |
| V007R | 1.53 | Y151R | 1.75 |
| V007T | 1.23 | Y151T | 1.13 |
| V007Y | 1.11 | Y151V | 1.25 |
| T049G | 1.01 | Y151W | 1.22 |
| T049H | 1.25 | I156M | 1.11 |
| T049I | 1.24 | I156R | 1.22 |
| T049K | 1.01 | I156T | 1.03 |
| T049L | 1.25 | I156W | 1.16 |
| T049N | 1.10 | G196R | 1.13 |
| T049P | 1.24 | Q273I | 1.18 |
| T049Q | 1.30 | Q273P | 1.13 |
| T049W | 1.10 | Q273Y | 1.09 |
| A058I | 1.04 | T278K | 1.09 |
| A058P | 1.10 | T278M | 1.02 |
| A058R | 1.04 | T278P | 1.07 |
| F063I | 1.11 | N280K | 1.02 |
| F063L | 1.03 | N280R | 1.04 |

Example 8

Stability of Thermolysin Variants in TIDE® 2× Liquid Detergent

In this example, experiments were conducted to assess the stability of various singly substituted thermolysin (also referred to herein as Proteinase-T or PrT) variants in the presence of liquid detergent. As described in Example 1, the stability of thermolysin variants was measured by determining the AGLA activity before and after incubation in the presence of TIDE® 2× heavy duty liquid (HDL) detergent at an elevated temperature. The tables contain the relative stability values compared to wild-type thermolysin, which is the quotient of the variant residual activity divided by the wild-type residual activity. A value greater than one indicates higher stability in the presence of detergent. In Table 8-1 and Table 8-2, data are provided showing the relative stability of single-substitution variants of thermolysin relative to the stability of wild-type thermolysin in HDL detergent in the presence and absence of DTPA.

TABLE 8-1

Stability Of Variants In 25% TIDE ® 2X With DTPA

| Variant | PI | Variant | PI |
|---|---|---|---|
| T006A | 1.01 | Y151Q | 1.03 |
| T006C | 1.03 | Y151R | 1.26 |
| T049D | 1.05 | Y151S | 1.23 |
| T049I | 1.01 | Y151T | 1.18 |
| T049L | 1.02 | Y151V | 1.11 |
| T049M | 1.02 | Y151W | 1.02 |
| T049N | 1.03 | I156E | 1.58 |
| T049S | 1.08 | I156H | 1.21 |
| A056C | 1.01 | I156K | 1.07 |

TABLE 8-1-continued

Stability Of Variants In 25% TIDE ® 2X With DTPA

| Variant | PI | Variant | PI |
|---|---|---|---|
| A056R | 1.10 | I156M | 1.19 |
| A056Y | 1.05 | I156R | 1.15 |
| A058S | 1.02 | I156T | 1.08 |
| S065C | 1.05 | I156W | 1.12 |
| S065E | 1.08 | G196D | 1.02 |
| S065I | 1.05 | G196H | 1.19 |
| S065T | 1.04 | Q273A | 1.03 |
| S065V | 1.08 | Q273N | 1.25 |
| S065Y | 1.05 | Q273T | 1.08 |
| Q128C | 1.01 | Q273W | 1.05 |
| Q128I | 1.32 | Q273Y | 1.05 |
| Q128M | 1.06 | T278C | 1.05 |
| Q128T | 1.18 | T278H | 1.07 |
| Q128V | 1.45 | T278M | 1.09 |
| Q128Y | 1.09 | T278N | 1.07 |
| Y151A | 1.15 | T278S | 1.08 |
| Y151C | 1.25 | T278Y | 1.05 |
| Y151D | 1.12 | N280E | 1.13 |
| Y151E | 1.10 | N280I | 1.16 |
| Y151H | 1.11 | N280L | 1.21 |
| Y151M | 1.09 | N280M | 1.16 |
| Y151N | 1.25 | N280S | 1.19 |

TABLE 8-2

Stability Of Variants In 25% TIDE ® 2X Without DTPA

| Variant | PI | Variant | PI |
|---|---|---|---|
| T006C | 1.07 | S065V | 1.08 |
| T049D | 1.28 | S065W | 1.09 |
| T049N | 1.07 | S065Y | 1.05 |
| T049Q | 1.07 | Q128C | 1.05 |
| T049S | 1.26 | Q128I | 1.19 |
| A056C | 1.19 | Q128M | 1.09 |
| A056E | 1.07 | Q128T | 1.15 |
| A058C | 1.01 | Q128V | 1.20 |
| A058E | 1.24 | Q128Y | 1.05 |
| Q061E | 1.05 | Y151A | 1.24 |
| Q061M | 1.01 | Y151C | 1.09 |
| S065C | 1.14 | Y151N | 1.05 |
| S065D | 1.20 | Y151S | 1.17 |
| S065E | 1.34 | Y151T | 1.10 |
| S065P | 1.18 | I156E | 1.09 |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in the relevant fields are intended to be within the scope of the following claims.

We claim:

1. An isolated thermolysin variant, wherein said thermolysin variant has at least 95% amino acid identity with the amino acid sequence set forth in SEQ ID NO: 3 and comprises a substitution at position 65 of the amino acid sequence set forth as SEQ ID NO: 3, wherein said substitution is selected from the group consisting of S065I, S065T, S065C, S065D, S065E, S065V, S065W, and S065Y.

2. The isolated thermolysin variant of claim 1, wherein said variant has an improvement in thermostability as compared to wild-type *Geobacillus caldoproteolyticus* thermolysin set forth in SEQ ID NO:3, wherein said improvement in stability is determined by the stability assay set forth in Example 1C.

3. A cleaning composition comprising the isolated thermolysin variant of claim 1 and a detergent.

4. The composition of claim 3, wherein said composition further comprises at least one calcium ion and/or zinc ion.

5. The composition of claim 3, wherein said composition further comprises at least one stabilizer.

6. The composition of claim 5, wherein said stabilizer is chosen from borax, glycerol, zinc ions, calcium ions, and calcium formate.

7. The composition of claim 5, wherein said stabilizer is at least one competitive inhibitor that stabilizes the at least one thermolysin in the presence of an anionic surfactant.

8. The composition of claim 3, further comprising at least one additional enzyme or enzyme derivative chosen from proteases, amylases, lipases, mannanases, pectinases, cutinases, oxidoreductases, hemicellulases, and cellulases.

9. The composition of claim 3, wherein said composition comprises at least about 0.0001 weight percent of said thermolysin variant.

10. The composition of claim 3, wherein said composition comprises from about 0.001 to about 0.5 weight percent of said thermolysin variant.

11. The composition of claim 3, wherein said composition is a liquid.

12. A method of cleaning, comprising the step of contacting a surface and/or an article comprising a fabric with a cleaning composition comprising the isolated thermolysin variant of claim 3.

* * * * *

SEQUENCE LISTING

<160> NUMBER OF SEQ ID NOS: 10

<210> SEQ ID NO 1
<211> LENGTH: 1647
<212> TYPE: DNA
<213> ORGANISM: Geobacillus caldoproteolyticus

<400> SEQUENCE: 1

```
atgaaaatga aaatgaaatt agcatcgttt ggtcttgcag caggactagc ggcccaagta      60
ttttaccttt acaatgcgct ggcttcaacg gaacacgtta catggaacca acaatttcaa     120
accctcaat tcatctccgg tgatctgctg aaagtgaatg gcacatcccc agaagaactc     180
gtctatcaat atgttgaaaa aacgaaaac aagtttaaat tcatgaaaa cgctaaggat     240
actctacaat tgaaagaaaa gaaaaatgat aaccttggtt ttacgtttat gcgcttccaa     300
caaacgtata aagggattcc tgtgtttgga gcagtagtaa ctgcgcacgt gaaagatggc     360
acgctgacgg cgctatcagg gacactgatt ccgaatttgg acacgaaagg atccttaaaa     420
agcgggaaga aattgagtga aaacaagcg cgtgacattg ctgaaaaaga tttagtggca     480
aatgtaacaa aggaagtacc ggaatatgaa cagggaaaag acaccgagtt tgttgtttat     540
gtcaatgggg acgaggcttc tttagcgtac gttgtcaatt taaacttttt aactcctgaa     600
ccaggaaact ggctgtatat cattgatgcc gtagacggaa aaatttaa taaatttaac     660
caacttgacg ccgcaaaacc aggtgatgtg aagtcgataa caggaacatc aactgtcgga     720
gtgggaagag gagtacttgg tgatcaaaaa aatattaata caacctactc tacgtactac     780
tatttacaag ataatacgcg tggaaatggg attttcacgt atgatgcgaa ataccgtacg     840
acattgccgg gaagcttatg ggcagatgca gataaccaat ttttgcgag ctatgatgct     900
ccagcggttg atgctcatta ttacgctggt gtgacatatg actactataa aaatgttcat     960
aaccgtctca gttacgacgg aaataatgca gctattagat catccgttca ttatagccaa    1020
ggctataata acgcattttg aacggttcg caaatggtgt atggcgatgg tgatggtcaa    1080
acatttattc cactttctgg tggtattgat gtggtcgcac atgagttaac gcatgcggta    1140
accgattata cagccggact catttatcaa acgaatctg gtgcaattaa tgaggcaata    1200
tctgatattt ttggaacgtt agtcgaattt tacgctaaca aaaatccaga ttgggaaatt    1260
ggagaggatg tgtatacacc tggtatttca ggggattcgc tccgttcgat gtccgatccg    1320
gcaaagtatg tgatccaga tcactattca aagcgctata caggcacgca agataatggc    1380
ggggttcata tcaatagcgg aattatcaac aaagccgctt atttgattag ccaaggcgg    1440
acgcattacg gtgtgagtgt tgtcggaatc ggacgcgata aattggggaa aattttctat    1500
cgtgcattaa cgcaatattt aacaccaacg tccaactta gccaacttcg tgctgccgct    1560
gttcaatcag ccactgactt gtacggttcg acaagccagg aagtcgcttc tgtgaagcag    1620
gcctttgatg cggtagggt gaaataa                                         1647
```

<210> SEQ ID NO 2
<211> LENGTH: 548
<212> TYPE: PRT
<213> ORGANISM: Geobacillus caldoproteolyticus

<400> SEQUENCE: 2

```
Met Lys Met Lys Met Lys Leu Ala Ser Phe Gly Leu Ala Ala Gly Leu
1               5                   10                  15

Ala Ala Gln Val Phe Leu Pro Tyr Asn Ala Leu Ala Ser Thr Glu His
            20                  25                  30

Val Thr Trp Asn Gln Gln Phe Gln Thr Pro Gln Phe Ile Ser Gly Asp
        35                  40                  45

Leu Leu Lys Val Asn Gly Thr Ser Pro Glu Glu Leu Val Tyr Gln Tyr
    50                  55                  60
```

-continued

```
Val Glu Lys Asn Glu Asn Lys Phe Lys Phe His Glu Asn Ala Lys Asp
 65                  70                  75                  80

Thr Leu Gln Leu Lys Glu Lys Lys Asn Asp Asn Leu Gly Phe Thr Phe
                 85                  90                  95

Met Arg Phe Gln Gln Thr Tyr Lys Gly Ile Pro Val Phe Gly Ala Val
            100                 105                 110

Val Thr Ala His Val Lys Asp Gly Thr Leu Thr Ala Leu Ser Gly Thr
        115                 120                 125

Leu Ile Pro Asn Leu Asp Thr Lys Gly Ser Leu Lys Ser Gly Lys Lys
130                 135                 140

Leu Ser Glu Lys Gln Ala Arg Asp Ile Ala Glu Lys Asp Leu Val Ala
145                 150                 155                 160

Asn Val Thr Lys Glu Val Pro Glu Tyr Glu Gln Gly Lys Asp Thr Glu
                165                 170                 175

Phe Val Val Tyr Val Asn Gly Asp Glu Ala Ser Leu Ala Tyr Val Val
            180                 185                 190

Asn Leu Asn Phe Leu Thr Pro Glu Pro Gly Asn Trp Leu Tyr Ile Ile
        195                 200                 205

Asp Ala Val Asp Gly Lys Ile Leu Asn Lys Phe Asn Gln Leu Asp Ala
210                 215                 220

Ala Lys Pro Gly Asp Val Lys Ser Ile Thr Gly Thr Ser Thr Val Gly
225                 230                 235                 240

Val Gly Arg Gly Val Leu Gly Asp Gln Lys Asn Ile Asn Thr Thr Tyr
                245                 250                 255

Ser Thr Tyr Tyr Tyr Leu Gln Asp Asn Thr Arg Gly Asn Gly Ile Phe
            260                 265                 270

Thr Tyr Asp Ala Lys Tyr Arg Thr Thr Leu Pro Gly Ser Leu Trp Ala
        275                 280                 285

Asp Ala Asp Asn Gln Phe Phe Ala Ser Tyr Asp Ala Pro Ala Val Asp
290                 295                 300

Ala His Tyr Tyr Ala Gly Val Thr Tyr Asp Tyr Tyr Lys Asn Val His
305                 310                 315                 320

Asn Arg Leu Ser Tyr Asp Gly Asn Asn Ala Ala Ile Arg Ser Ser Val
                325                 330                 335

His Tyr Ser Gln Gly Tyr Asn Asn Ala Phe Trp Asn Gly Ser Gln Met
            340                 345                 350

Val Tyr Gly Asp Gly Asp Gln Thr Phe Ile Pro Leu Ser Gly Gly
        355                 360                 365

Ile Asp Val Val Ala His Glu Leu Thr His Ala Val Thr Asp Tyr Thr
370                 375                 380

Ala Gly Leu Ile Tyr Gln Asn Glu Ser Gly Ala Ile Asn Glu Ala Ile
385                 390                 395                 400

Ser Asp Ile Phe Gly Thr Leu Val Glu Phe Tyr Ala Asn Lys Asn Pro
                405                 410                 415

Asp Trp Glu Ile Gly Glu Asp Val Tyr Thr Pro Gly Ile Ser Gly Asp
            420                 425                 430

Ser Leu Arg Ser Met Ser Asp Pro Ala Lys Tyr Gly Asp Pro Asp His
        435                 440                 445

Tyr Ser Lys Arg Tyr Thr Gly Thr Gln Asp Asn Gly Gly Val His Ile
450                 455                 460

Asn Ser Gly Ile Ile Asn Lys Ala Ala Tyr Leu Ile Ser Gln Gly Gly
465                 470                 475                 480

Thr His Tyr Gly Val Ser Val Val Gly Ile Gly Arg Asp Lys Leu Gly
```

```
                        485                 490                 495
Lys Ile Phe Tyr Arg Ala Leu Thr Gln Tyr Leu Thr Pro Thr Ser Asn
                    500                 505                 510

Phe Ser Gln Leu Arg Ala Ala Val Gln Ser Ala Thr Asp Leu Tyr
                515                 520                 525

Gly Ser Thr Ser Gln Glu Val Ala Ser Val Lys Gln Ala Phe Asp Ala
            530                 535                 540

Val Gly Val Lys
545

<210> SEQ ID NO 3
<211> LENGTH: 316
<212> TYPE: PRT
<213> ORGANISM: Geobacillus caldoproteolyticus

<400> SEQUENCE: 3

Ile Thr Gly Thr Ser Thr Val Gly Val Gly Arg Gly Val Leu Gly Asp
1               5                   10                  15

Gln Lys Asn Ile Asn Thr Thr Tyr Ser Thr Tyr Tyr Leu Gln Asp
            20                  25                  30

Asn Thr Arg Gly Asn Gly Ile Phe Thr Tyr Asp Ala Lys Tyr Arg Thr
        35                  40                  45

Thr Leu Pro Gly Ser Leu Trp Ala Asp Ala Asp Asn Gln Phe Phe Ala
    50                  55                  60

Ser Tyr Asp Ala Pro Ala Val Asp Ala His Tyr Tyr Ala Gly Val Thr
65                  70                  75                  80

Tyr Asp Tyr Tyr Lys Asn Val His Asn Arg Leu Ser Tyr Asp Gly Asn
                85                  90                  95

Asn Ala Ala Ile Arg Ser Ser Val His Tyr Ser Gln Gly Tyr Asn Asn
            100                 105                 110

Ala Phe Trp Asn Gly Ser Gln Met Val Tyr Gly Asp Gly Asp Gly Gln
        115                 120                 125

Thr Phe Ile Pro Leu Ser Gly Gly Ile Asp Val Val Ala His Glu Leu
    130                 135                 140

Thr His Ala Val Thr Asp Tyr Thr Ala Gly Leu Ile Tyr Gln Asn Glu
145                 150                 155                 160

Ser Gly Ala Ile Asn Glu Ala Ile Ser Asp Ile Phe Gly Thr Leu Val
                165                 170                 175

Glu Phe Tyr Ala Asn Lys Asn Pro Asp Trp Glu Ile Gly Glu Asp Val
            180                 185                 190

Tyr Thr Pro Gly Ile Ser Gly Asp Ser Leu Arg Ser Met Ser Asp Pro
        195                 200                 205

Ala Lys Tyr Gly Asp Pro Asp His Tyr Ser Lys Arg Tyr Thr Gly Thr
    210                 215                 220

Gln Asp Asn Gly Gly Val His Ile Asn Ser Gly Ile Ile Asn Lys Ala
225                 230                 235                 240

Ala Tyr Leu Ile Ser Gln Gly Gly Thr His Tyr Gly Val Ser Val Val
                245                 250                 255

Gly Ile Gly Arg Asp Lys Leu Gly Lys Ile Phe Tyr Arg Ala Leu Thr
            260                 265                 270

Gln Tyr Leu Thr Pro Thr Ser Asn Phe Ser Gln Leu Arg Ala Ala Ala
        275                 280                 285

Val Gln Ser Ala Thr Asp Leu Tyr Gly Ser Thr Ser Gln Glu Val Ala
    290                 295                 300
```

Ser Val Lys Gln Ala Phe Asp Ala Val Gly Val Lys
305                 310                 315

<210> SEQ ID NO 4
<211> LENGTH: 39
<212> TYPE: DNA
<213> ORGANISM: Artificial
<220> FEATURE:
<223> OTHER INFORMATION: synthetic primer

<400> SEQUENCE: 4
gagagggtaa agaatgaaaa tgaaaatgaa attagcatc         39

<210> SEQ ID NO 5
<211> LENGTH: 46
<212> TYPE: DNA
<213> ORGANISM: Artificial
<220> FEATURE:
<223> OTHER INFORMATION: synthetic primer

<400> SEQUENCE: 5
gttaacctgc aggaattctt atttcacccc taccgcatca aaggcc    46

<210> SEQ ID NO 6
<211> LENGTH: 40
<212> TYPE: DNA
<213> ORGANISM: Artificial
<220> FEATURE:
<223> OTHER INFORMATION: synthetic primer

<400> SEQUENCE: 6
cattttcatt ttcattcttt accctctcct tttgctagac         40

<210> SEQ ID NO 7
<211> LENGTH: 45
<212> TYPE: DNA
<213> ORGANISM: Artificial
<220> FEATURE:
<223> OTHER INFORMATION: synthetic primer

<400> SEQUENCE: 7
ccataagaat tcctgcaggt taacagagga cggatttcct gaagg     45

<210> SEQ ID NO 8
<211> LENGTH: 5335
<212> TYPE: DNA
<213> ORGANISM: Artificial
<220> FEATURE:
<223> OTHER INFORMATION: synthetic expression vector

<400> SEQUENCE: 8
agcttggaga caaggtaaag gataaaacag cacaattcca agaaaaacac gatttagaac    60
ctaaaaagaa cgaatttgaa ctaactcata accgagaggt aaaaaaagaa cgaagtcgag   120
atcagggaat gagtttataa aataaaaaaa gcacctgaaa aggtgtcttt ttttgatggt   180
tttgaacttg ttctttctta tcttgataca tatagaaata acgtcatttt tattttagtt   240
gctgaaaggt gcgttgaagt gttggtatgt atgtgtttta aagtattgaa aacccttaaa   300
attggttgca cagaaaaacc ccatctgtta aagttataag tgactaaaca aataactaaa   360
tagatggggg tttcttttaa tattatgtgt cctaatagta gcatttattc agatgaaaaa   420
tcaagggttt tagtggacaa gacaaaaagt ggaaagtga gaccatggag agaaaagaaa   480
atcgctaatg ttgattactt tgaacttctg catattcttg aatttaaaaa ggctgaaaga   540

```
gtaaaagatt gtgctgaaat attagagtat aaacaaaatc gtgaaacagg cgaaagaaag    600
ttgtatcgag tgtggttttg taaatccagg ctttgtccaa tgtgcaactg gaggagagca    660
atgaaacatg gcattcagtc acaaaaggtt gttgctgaag ttattaaaca aaagccaaca    720
gttcgttggt tgtttctcac attaacagtt aaaaatgttt atgatggcga agaattaaat    780
aagagtttgt cagatatggc tcaaggattt cgccgaatga tgcaatataa aaaaattaat    840
aaaaatcttg ttggttttat gcgtgcaacg gaagtgacaa taataataa agataattct    900 tataatcagc acatgcatgt attggtatgt gtggaaccaa cttattttaa gaatacagaa    960
aactacgtga atcaaaaaca atggattcaa ttttggaaaa aggcaatgaa attagactat   1020
gatccaaatg taaagttca aatgattcga ccgaaaaata aatataaatc ggatatacaa   1080
tcggcaattg acgaaactgc aaaatatcct gtaaaggata cggatttat gaccgatgat   1140 gaagaaaaga atttgaaacg tttgtctgat ttggaggaag gtttacaccg taaaaggtta   1200
atctcctatg gtggttttgtt aaagaaata cataaaaaat taaaccttga tgacacagaa   1260
gaaggcgatt tgattcatac agatgatgac gaaaaagccg atgaagatgg attttctatt   1320
attgcaatgt ggaattggga acggaaaaat tattttatta agagtagtt caacaaacgg   1380 gccagttgt tgaagattag atgctataat tgttattaaa aggattgaag gatgcttagg   1440
aagacgagtt attaatagct gaataagaac ggtgctctcc aaatattctt atttagaaaa   1500
gcaaatctaa aattatctga aaagggaatg agaatagtga atggaccaat aataatgact   1560
agagaagaaa gaatgaagat tgttcatgaa attaaggaac gaatattgga taaatatggg   1620
gatgatgtta aggctattgg tgtttatggc tctcttggtc gtcagactga tgggccctat   1680
tcggatattg agatgatgtg tgtcatgtca acagaggaag cagagttcag ccatgaatgg   1740
acaaccggtg agtggaaggt ggaagtgaat tttgatagcg aagagattct actagattat   1800
gcatctcagg tggaatcaga ttggccgctt acacatggtc aatttttctc tattttgccg   1860
atttatgatt caggtggata cttagagaaa gtgtatcaaa ctgctaaatc ggtagaagcc   1920
caaacgttcc acgatgcgat ttgtgccctt atcgtagaag agctgtttga atatgcaggc   1980
aaatggcgta atattcgtgt gcaaggaccg acaacatttc taccatcctt gactgtacag   2040
gtagcaatgg caggtgccat gttgattggt ctgcatcatc gcatctgtta tacgacgagc   2100
gcttcggtct taactgaagc agttaagcaa tcagatcttc cttcaggtta tgaccatctg   2160
tgccagttcg taatgtctgg tcaactttcc gactctgaga aacttctgga atcgctagag   2220
aatttctgga atgggattca ggagtggaca gaacgcacg gatatatagt ggatgtgtca   2280
aaacgcatac cattttgaac gatgacctct aataattgtt aatcatgttg gttacgtatt   2340
tattaacttc tcctagtatt agtaattatc atggctgtca tggcgcatta acggaataaa   2400
gggtgtgctt aaatcgggcc atttttgcgta ataagaaaaa ggattaatta tgagcgaatt   2460
gaattaataa taaggtaata gatttacatt agaaaatgaa aggggatttt atgcgtgaga   2520
atgttacagt ctatcccggc attgccagtc ggggatatta aaaagagtat aggtttttat   2580
tgcgataaac taggtttcac tttggttcac catgaagatg gattcgcagt tctaatgtgt   2640
aatgaggttc ggattcatct atgggaggca agtgatgaag ctggcgctc tcgtagtaat   2700 gattcaccgg tttgtacagg tgcggagtcg tttattgctg gtactgctag ttgccgcatt   2760
gaagtagagg gaattgatga attatatcaa catattaagc ctttgggcat tttgcacccc   2820
aatacatcat taaagatca gtggtgggat gaacgagact ttgcagtaat tgatcccgac   2880
aacaatttga ttagctttt tcaacaaata aaaagctaaa atctattatt aatctgttca   2940
```

```
gcaatcgggc gcgattgctg aataaaagat acgagagacc tctcttgtat ctttttatt      3000
ttgagtggtt ttgtccgtta cactagaaaa ccgaaagaca ataaaaattt tattcttgct      3060
gagtctggct ttcggtaagc tagacaaaac ggacaaaata aaattggca agggtttaaa       3120
ggtggagatt ttttgagtga tcttctcaaa aaatactacc tgtcccttgc tgattttttaa     3180
acgagcacga gagcaaaacc cccctttgct gaggtggcag agggcaggtt tttttgtttc      3240
ttttttctcg taaaaaaaag aaaggtctta aaggttttat ggttttggtc ggcactgccg      3300
acagcctcgc agagcacaca ctttatgaat ataaagtata gtgtgttata ctttacttgg      3360
aggtggttgc cggaaagagc gaaaatgcct cacatttgtg ccacctaaaa aggagcgatt      3420
tacatatgag ttatgcagtt tgtagaatgc aaaaagtgaa atcaggggga tcctaatcgg      3480
cgcttttctt ttggaagaaa atataggggaa atggtactt gttaaaaatt cggaatattt       3540
atacaatatc atatgtttca cattgaaagg ggaggaaaat cgtgaaacaa caaaaacggc      3600
tttagtctag caaaggaga gggtaaagaa tgaaaatgaa atgaaattta gcatcgtttg        3660
gtcttgcagc aggactagcg gcccaagtat ttttaccta caatgcgctg gcttcaacgg         3720
aacacgttac atggaaccaa caatttcaaa cccctcaatt catctccggt gatctgctga      3780
aagtgaatgg cacatcccca gaagaactcg tctatcaata tgttgaaaaa aacgaaaaca     3840
agtttaaatt tcatgaaaac gctaaggata ctctacaatt gaaagaaaag aaaaatgata      3900
accttggttt tacgtttatg cgcttccaac aaacgtataa agggattcct gtgtttggag      3960
cagtagtaac tgcgcacgtg aaagatggca cgctgacggc gctatcaggg acactgattc      4020
cgaatttgga cacgaaagga tccttaaaaa gcgggaagaa attgagtgag aaacaagcgc      4080
gtgacattgc tgaaaaagat ttagtggcaa atgtaacaaa ggaagtaccg gaatatgaac      4140
agggaaaaga caccgagttt gttgtttatg tcaatgggga cgaggcttct ttagcgtacg      4200
ttgtcaattt aaactttta actcctgaac caggaaactg gctgtatatc attgatgccg       4260
tagacggaaa aattttaaat aaatttaacc aacttgacgc cgcaaaacca ggtgatgtga      4320
agtcgataac aggaacatca actgtcggag tgggaagagg agtacttggt gatcaaaaaa      4380
atattaatac aacctactct acgtactact atttacaaga taatacgcgt ggaaatggga      4440
ttttcacgta tgatgcgaaa taccgtacga cattgccggg aagcttatgg gcagatgcag      4500
ataaccaatt ttttgcgagc tatgatgctc agcggttga tgctcattat tacgctggtg       4560
tgacatatga ctactataaa aatgttcata accgtctcag ttacgacgga ataatgcag       4620
ctattagatc atccgttcat tatagccaag gctataataa cgcattttgg aacggttcgc      4680
aaatggtgta tggcgatggt gatggtcaaa catttattcc actttctggt ggtattgatg      4740
tggtcgcaca tgagttaacg catgcggtaa ccgattatac agccggactc atttatcaaa      4800
acgaatctgg tgcaattaat gaggcaatat ctgatatttt tggaacgtta gtcgaatttt       4860
acgctaacaa aaatccagat tgggaaattg gagaggatgt gtatacacct ggtatttcag      4920
gggattcgct ccgttcgatg tccgatccgg caaagtatgg tgatccagat cactattcaa      4980
agcgctatac aggcacgcaa gataatggcg gggttcatat caatagcgga attatcaaca      5040
aagccgctta tttgattagc caaggcgta cgcattacg tgtgagtgtt gtcggaatcg        5100
gacgcgataa attggggaaa attttctatc gtgcattaac gcaatattta acaccaacgt     5160
ccaactttag ccaacttcgt gctgccgctg ttcaatcagc cactgacttg tacgttcga      5220
caagccagga agtcgcttct gtgaagcagg cctttgatgc ggtaggggtg aaataagaat     5280
```

```
tcctgcaggt taacagagga cggatttcct gaaggaaatc cgttttttta tttta            5335
```

<210> SEQ ID NO 9
<211> LENGTH: 300
<212> TYPE: PRT
<213> ORGANISM: Bacillus amyloliquefaciens

<400> SEQUENCE: 9

| Ala | Ala | Thr | Thr | Gly | Thr | Gly | Thr | Thr | Leu | Lys | Gly | Lys | Thr | Val | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Asn | Ile | Ser | Ser | Glu | Ser | Gly | Lys | Tyr | Val | Leu | Arg | Asp | Leu | Ser |
|-----|-----|-----|-----|-----|-----|-----|-----|-----|-----|-----|-----|-----|-----|-----|-----|
|     |     |     |     | 20  |     |     |     |     | 25  |     |     |     |     | 30  |     |

| Lys | Pro | Thr | Gly | Thr | Gln | Ile | Ile | Thr | Tyr | Asp | Leu | Gln | Asn | Arg | Glu |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Tyr | Asn | Leu | Pro | Gly | Thr | Leu | Val | Ser | Ser | Thr | Thr | Asn | Gln | Phe | Thr |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Thr | Ser | Ser | Gln | Arg | Ala | Ala | Val | Asp | Ala | His | Tyr | Asn | Leu | Gly | Lys |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Val | Tyr | Asp | Tyr | Phe | Tyr | Gln | Lys | Phe | Asn | Arg | Asn | Ser | Tyr | Asp | Asn |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Lys | Gly | Gly | Lys | Ile | Val | Ser | Ser | Val | His | Tyr | Gly | Ser | Arg | Tyr | Asn |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Asn | Ala | Ala | Trp | Ile | Gly | Asp | Gln | Met | Ile | Tyr | Gly | Asp | Gly | Asp | Gly |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Ser | Phe | Phe | Ser | Pro | Leu | Ser | Gly | Ser | Met | Asp | Val | Thr | Ala | His | Glu |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Met | Thr | His | Gly | Val | Thr | Gln | Glu | Thr | Ala | Asn | Leu | Asn | Tyr | Glu | Asn |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Gln | Pro | Gly | Ala | Leu | Asn | Glu | Ser | Phe | Ser | Asp | Val | Phe | Gly | Tyr | Phe |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Asn | Asp | Thr | Glu | Asp | Trp | Asp | Ile | Gly | Glu | Asp | Ile | Thr | Val | Ser | Gln |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Pro | Ala | Leu | Arg | Ser | Leu | Ser | Asn | Pro | Thr | Lys | Tyr | Gly | Gln | Pro | Asp |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Asn | Phe | Lys | Asn | Tyr | Lys | Asn | Leu | Pro | Asn | Thr | Asp | Ala | Gly | Asp | Tyr |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Gly | Gly | Val | His | Thr | Asn | Ser | Gly | Ile | Pro | Asn | Lys | Ala | Ala | Tyr | Asn |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Thr | Ile | Thr | Lys | Ile | Gly | Val | Asn | Lys | Ala | Glu | Gln | Ile | Tyr | Tyr | Arg |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Ala | Leu | Thr | Val | Tyr | Leu | Thr | Pro | Ser | Ser | Thr | Phe | Lys | Asp | Ala | Lys |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Ala | Ala | Leu | Ile | Gln | Ser | Ala | Arg | Asp | Leu | Tyr | Gly | Ser | Gln | Asp | Ala |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Ala | Ser | Val | Glu | Ala | Ala | Trp | Asn | Ala | Val | Gly | Leu |
|-----|-----|-----|-----|-----|-----|-----|-----|-----|-----|-----|-----|
|     | 290 |     |     |     |     | 295 |     |     |     |     | 300 |

<210> SEQ ID NO 10
<211> LENGTH: 4
<212> TYPE: PRT
<213> ORGANISM: Artificial
<220> FEATURE:
<223> OTHER INFORMATION: synthetic reagent
<220> FEATURE:
<221> NAME/KEY: MISC_FEATURE
<222> LOCATION: (1)..(1)
<223> OTHER INFORMATION: aminobenzoyl modification
<220> FEATURE:

-continued

```
<221> NAME/KEY: MISC_FEATURE
<222> LOCATION: (4)..(4)
<223> OTHER INFORMATION: nitrobenzylamide modification

<400> SEQUENCE: 10

Ala Gly Leu Ala
1
```